(12) United States Patent
Miller et al.

(10) Patent No.: US 6,693,153 B2
(45) Date of Patent: Feb. 17, 2004

(54) CATALYST SYSTEM FOR THE POLYMERIZATION OF ALKENES TO POLYOLEFINS

(75) Inventors: Stephen A. Miller, Cambridge, MA (US); John E. Bercaw, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/267,988

(22) Filed: Oct. 8, 2002

(65) Prior Publication Data

US 2003/0139544 A1 Jul. 24, 2003

Related U.S. Application Data

(62) Division of application No. 09/488,431, filed on Jan. 20, 2000, now Pat. No. 6,469,188.
(60) Provisional application No. 60/150,083, filed on Aug. 20, 1999, provisional application No. 60/116,646, filed on Jan. 20, 1999, and provisional application No. 60/116,522, filed on Jan. 20, 1999.

(51) Int. Cl.[7] ............................. C08F 4/44; C07F 17/00; B01J 31/00
(52) U.S. Cl. ..................... 526/127; 502/103; 502/117; 526/161; 526/351; 526/352; 526/943; 534/15; 556/12; 556/13; 556/43; 556/53
(58) Field of Search ............................. 556/12, 13, 43, 556/53; 534/15; 502/103, 117; 526/127, 161, 351, 352, 943

(56) References Cited

U.S. PATENT DOCUMENTS

| | | | | |
|---|---|---|---|---|
| 4,542,199 A | * | 9/1985 | Kaminsky et al. | 526/160 |
| 4,871,705 A | * | 10/1989 | Hoel | 502/117 |
| 5,001,205 A | * | 3/1991 | Hoel | 526/128 |
| 5,036,034 A | * | 7/1991 | Ewen | 502/117 |
| 5,491,207 A | * | 2/1996 | Hoel | 526/129 |
| 5,594,080 A | * | 1/1997 | Waymouth et al. | 526/126 |
| 5,696,213 A | * | 12/1997 | Schiffino et al. | 526/158 |
| 5,756,614 A | * | 5/1998 | Chien et al. | 526/160 |
| 5,770,664 A | * | 6/1998 | Okumura et al. | 526/127 |
| 5,886,123 A | * | 3/1999 | Resconi et al. | 526/348.6 |
| 5,969,070 A | * | 10/1999 | Waymouth et al. | 526/351 |

FOREIGN PATENT DOCUMENTS

| | | | |
|---|---|---|---|
| EP | 427697 | * | 10/1990 |
| EP | 277003 | * | 1/1998 |
| EP | 277004 | * | 1/1998 |
| EP | 1 138 687 A1 | * | 4/2001 |
| JP | 7002935 | * | 1/1995 |
| JP | 07-002935 | * | 1/1995 |
| JP | 09-194552 | * | 7/1997 |
| JP | 9194552 | * | 7/1997 |
| WO | WO 98/54230 | * | 12/1998 |
| WO | WO 99/14219 | * | 3/1999 |
| WO | WO 99/67309 | * | 12/1999 |
| WO | WO 00/49029 | * | 8/2000 |
| WO | WO 00/49056 | * | 8/2000 |
| WO | WO 01/27124 A1 | * | 4/2001 |

* cited by examiner

*Primary Examiner*—Porfirio Nazario-Gonzalez
(74) *Attorney, Agent, or Firm*—Bingham McCutchen LLP; David W. Maher

(57) ABSTRACT

The invention provides metallocene catalyst systems for the controlled polymerization of alkenes to a wide variety of polyolefins and olefin copolymers. Catalyst systems are provided that specifically produce isotactic, syndiotactic and steroblock polyolefins. The type of polymer produced can be controlled by varying the catalyst system, specifically by varying the ligand substituents. Such catalyst systems are particularly useful for the polymerization of polypropylene to give elastomeric polypropylenes. The invention also provides novel elastomeric polypropylene polymers characterized by dyad (m) tacticities of about 55% to about 65%, pentad (mmmm) tacticities of about 25% to about 35%, molecular weights ($M_w$) in the range of about 50,000 to about 2,000,000, and have mmrm+rrmr peak is less than about 5%.

56 Claims, No Drawings

CATALYST SYSTEM FOR THE POLYMERIZATION OF ALKENES TO POLYOLEFINS

RELATED APPLICATION DATA

This patent application is a divisional of and claims priority of U.S. application Ser. No. 09/488,431 filed Jan. 20, 2000, now U.S. Pat. No. 6,469,188 B1, which claims the benefit of provisional applications Serial No. 60/116,522 filed Jan. 20, 1999, Serial No. 60/116,646 filed Jan. 20, 1999 and Serial No. 60/150,083 filed Aug. 20, 1999, the entire disclosures of which are herein incorporated by reference.

GOVERNMENT SUPPORT

The government may have certain rights in this invention pursuant to Grant No. DE-FG03-88ER13431 from the Department of Energy.

FIELD OF THE INVENTION

This invention relates to catalysts, catalyst systems and methods of production of olefin polymers, including isotactic, syndiotactic and stereoblock polymer, and the polymers produced thereby.

BACKGROUND

The mechanical properties of a given polymer can generally be classified as rigid, flexible, or elastic. While metallocene catalysts are capable of producing polymers that fall into each of these classifications, the most intense efforts have been directed at surpassing existing systems in their aptitude for making rigid isotactic polypropylene and rigid or flexible polyethylene [1] More recently, growing efforts to devise metallocene catalysts capable of producing elastomeric polymers have revealed several different viable strategies: ethylene/α-olefin copolymers [2]; high molecular weight atactic polypropylene [3]; binary isotactic/atactic compatibilized polypropylene [4]; isotactic-atactic polypropylene [5]; stereoblock isotactic-atactic polypropylene [6]; and isotactic polypropylene with controllable stereoerror sequences. [7] Although the structure/property relationship of each of these regimes is not fully understood, the elastomeric properties undoubtedly rely on the existence of physical crosslinks in the presence of an amorphous phase. In the case of high molecular weight materials, the crosslinks can be simple chain entanglements. In the other examples, segments from several different polymer chains participate in crystalline regions, which physically connect the chains and provide crosslinks in an otherwise amorphous phase.

One of the best understood systems is that initially developed by Coates and Waymouth. [6, 8] Their unbridged metallocene (2-phenylindenyl)$_2$ZrCl$_2$, in the presence of methylaluminoxane (MAO), isomerizes between chiral and achiral coordination geometries during the formation of a given polypropylene chain. Since the chiral isomer is isospecific and the achiral isomer is aspecific, stereoblock isotactic-atactic polypropylene is obtained.

Elastomeric and other polyolefins with controlled stereostructures are useful for a wide variety of applications. Novel polyolefins, especially those with elastomeric properties, can be useful for a wide variety of applications. Accordingly, there is a need for catalyst systems capable of polymerizing alkenes to novel polyolefins.

There is also a need to develop catalysts sufficiently stable to be used on an industrial scale. Owing to the chelate effect, bridged metallocene catalysts tend to be more stable at elevated polymerization temperatures, and often behave more predictably when adsorbed on a support, a common industrial tactic.

Accordingly, there is a need for stable, readily synthesized catalyst systems capable of controlled polymerization of alkenes to give polyolefins.

SUMMARY

The invention provides bridged metallocene catalyst systems that are useful for the controlled polymerization of alkenes to polyolefins. Also provided are catalyst systems useful for polymerizing a variety of alkene monomers into stereocontrolled polymers including isotactic polymers, syndiotactic polymers and stereoblock polymers containing both hemiisotactic and isotactic regions. Catalysts of the invention can be chosen to provide a specific size range of produced polymers. Catalysts also can be chosen so as to produce a polymer with a desired microstructure.

This invention describes a new catalyst system for polymerizing $C_2$ to $C_{10}$ alk-1-enes to produce polyolefin polymers. The catalyst system includes two components: (a) an organometallic compound of the general formula (II),

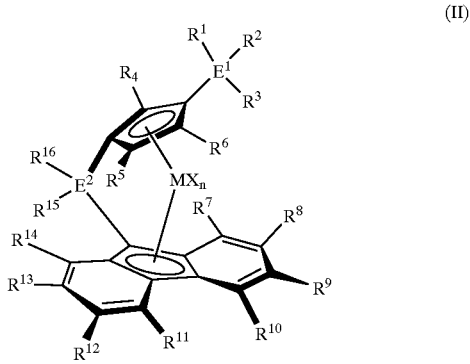

(II)

in which M is a metal of the III, IV, or V subgroup of the periodic system or a metal from the lanthamide or actinide groups; X is fluorine, chlorine, bromine, iodine, hydrogen, $C_1$ to $C_{10}$ alkyl, $C_6$ to $C_{20}$ aryl, alkylaryl, arylalkyl, fluoroalkyl, or fluoroaryl having 1 to 10 20 carbons in the alkyl moiety and 6 to 20 carbon atoms in the aryl moiety, or —OR$^{17}$ where R$^{17}$ is a $C_1$ to $C_{10}$ alkyl or $C_6$ to $C_{20}$ aryl; n is the formal oxidation state of M minus 2; E$^1$ is hydrogen, carbon, silicon, or germanium; E$^2$ is carbon, silicon, or germanium; R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, and R$^{16}$ are, independently, hydrogen, $C_1$ to $C_{10}$ alkyl, 3 to 10 membered cycloalkyl, which in turn may have from 1 to 10 $C_1$ to $C_{10}$ alkyls as substituents, $C_6$ to $C_{16}$ aryl or arylalkyl in which two adjacent substituents may together stand for cyclic groups having 4 to 16 carbon atoms which in turn may be substituted, or Si(R$^{18}$)$_3$ where R$^{18}$ is a $C_1$ to $C_{10}$ alkyl, $C_6$ to $C_{16}$ aryl or $C_3$ to $C_{10}$ cycloalkyl; and where E$^1$ is hydrogen, R$^1$, R$^2$ and R$^3$ are absent; or an organometallic compound of the general formula (III),

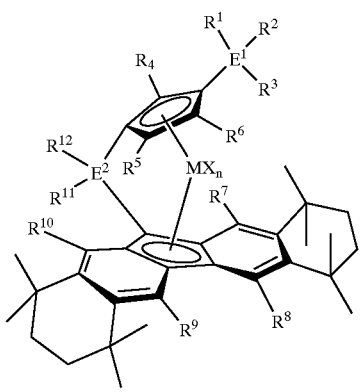

(III)

in which M is a metal of the III, IV, or V subgroup of the periodic system or a metal from the lanthamide or actinide groups; X is fluorine, chlorine, bromine, iodine, hydrogen, $C_1$ to $C_{10}$ alkyl, $C_6$ to $C_{20}$ aryl, alkylaryl, arylalkyl, fluoroalkyl, or fluoroaryl having 1 to 10 carbons in the alkyl moiety and 6 to 20 carbon atoms in the aryl moiety, or $—OR^{13}$ where $R^{13}$ is a $C_1$ to $C_{10}$ alkyl or $C_6$ to $C_{20}$ aryl; n is the formal oxidation state of M minus 2; $E^1$ is hydrogen, carbon, silicon, or germanium; $E^2$ is carbon, silicon, or germanium; $R^1$, $R^2$, $R^3$, $R^4$, $R^5$, $R^6$, $R^7$, $R^8$, $R^9$, $R^{10}$, $R^{11}$, and $R^{12}$ are, independently, hydrogen, $C_1$ to $C_{10}$ alkyl, 3 to 10 membered cycloalkyl, which in turn may have from 1 to 10 $C_1$ to $C_{10}$ alkyls as substituents, $C_6$ to $C_{16}$ aryl or arylalkyl in which two adjacent substituents may together stand for cyclic groups having 4 to 16 carbon atoms which in turn may be substituted, or $Si(R^{14})_3$ where $R^{14}$ is a $C_1$ to $C_{10}$ alkyl, $C_6$ to $C_{16}$ aryl or $C_3$ to $C_{10}$ cycloalkyl; and where $E^1$ is hydrogen, $R^1$, $R^2$ and $R^3$ are absent; and (b) an activator.

Catalyst System for Isotactic Polyolefins

Metallocene catalysts can be chosen according to the invention that produce isotactic polyolefins. The preferred catalyst for polymerizing $C_2$ to $C_{10}$ alk-1-enes to produce isotactic polyolefins is compound II or compound III wherein no elements of symmetry exist; that is, compound II or compound III are of $C_1$ symmetry. It is generally preferred that the $R^1$, $R^2$, $R^3$, and $E^1$ group is a sterically large group, for example an adamantyl group. The preferred metals are titanium, zirconium, hafnium, scandium, and yttrium. The preferred X are chlorine, bromine, hydrogen, methyl, phenyl, and benzyl. The preferred $E^2$ is carbon or silicon. The preferred R substituents are as follows: For II, $R^1$, $R^2$, $R^3$, and $E^1$ constitute the 2-methyl-2-adamantyl group; $R^4$, $R^5$, $R^6$, $R^7$, $R^8$, $R^9$, $R^{10}$, $R^{11}$, $R^{12}$, $R^{13}$, and $R^{14}$ are hydrogen; $R^{15}$ and $R^{16}$ are methyl, phenyl, or part of a cycloalkyl group, including cyclohexyl or adamantyl. For III, $R^1$, $R^2$, $R^3$, and $E^1$ constitute the 2-methyl-2-adamantyl group; $R^4$, $R^5$, $R^6$, $R^7$, $R^8$, $R^9$, and $R^{10}$ are hydrogen; $R^{11}$ and $R^{12}$ are methyl, phenyl, or part of a cycloalkyl group, including cyclohexyl or adamantyl.

Catalyst System for Syndiotactic Polyolefins

Catalyst systems also can be prepared that preferentially catalyze the formation of syndiotactic polyolefins from alkene precursors. The preferred catalyst for polymerizing $C_2$ to $C_{10}$ alk-1-enes to produce syndiotactic polyolefins is compound III wherein a mirror plane of symmetry exists; that is, compound III is of $C_s$ symmetry. The preferred metals are titanium, zirconium, hafiium, scandium, and yttrium. The preferred X are chlorine, bromine, hydrogen, methyl, phenyl, and benzyl. The preferred $E^1$ is carbon or silicon. The preferred R substituents are as follows: $E^1$ is hydrogen, $R^1$, $R^2$ and $R^3$ are absent; $R^4$, $R^5$, $R^6$, $R^7$, $R^8$, $R^9$ and $R^{10}$ are hydrogen; $R^{11}$ and $R^{12}$ are methyl, phenyl, or part of a cycloalkyl group, including cyclohexyl or adamantyl.

Catalyst System for Elastomeric Polyolefins

The preferred catalyst for polymerizing $C_2$ to $C_{10}$ alk-1-enes to produce stereoblock isotactic-hemiisotactic polyolefins is compound II wherein there are no symmetry elements; that is, compound II is of $C_1$ symmetry. The preferred metals are titanium, zirconium, hafnium, scandium, and yttrium. The preferred X are chlorine, bromine, hydrogen, methyl, phenyl, and benzyl. The preferred $E^1$ and $E^2$ are carbon and silicon. The preferred R substituents are as follows: $R^1$ is hydrogen; $R^2$, and $R^3$ are, independently, hydrogen, methyl, ethyl, isopropyl, tert-butyl, phenyl, trimethylsilyl, or part of a cycloalkyl group, including cyclohexyl, adamantyl, or 3,3,5,5-tetramethylcyclohexyl; $R^4$, $R^5$, $R^6$, $R^7$, $R^8$, $R^9$, $R^{10}$, $R^{11}$, $R^{12}$, $R^{13}$, and $R^{14}$ are hydrogen or methyl; and $R^{15}$ and $R^{16}$ are hydrogen, methyl, or phenyl.

Polyolefin Polymerization

The metallocenes of the present invention, in the presence of appropriate activators, are useful for the polymerization of alkenes, including ethylene and alpha-olefins, for example propylene, 1-butene, 1-pentene, 4-methyl-1-pentene, 1-hexene and combinations thereof. The polymerization of olefins is carried out by contacting the olefin with the catalyst systems comprising the transition metal component and in the presence of an appropriate cocatalyst, for example an alumoxane, or a Lewis acid for example $B(C_6F_5)_3$, or a protic acid containing a non-coordinating anion, for example $[PhNMe_2H]^+B(C_6F_5)_4^-$. Conditions suitable for the polymerization of olefins to polyolefins are known in the art. Suitable temperatures, pressures, and optional solvents can be determined by one of skill in the art for use in the present invention.

The metallocene catalyst systems of the present invention are useful for the polymerization of alkenes to polyolefins. In particular, catalysts can be selected to produce isotactic or syndiotactic polypropylene. Examples of catalysts suitable for the production of a particular type of catalyst are given above and in the following Examples. In one embodiment, the alkenes to be polymerized are alpha olefins.

The metallocene catalyst systems of the present invention are particularly useful for the polymerization of propylene to produce polypropylenes with novel elastomeric properties. By elastomeric, we mean a material which tends to regain its shape upon extension, or one which exhibits a positive power of recovery at 100%, 200% and 300% elongation. The properties of elastomers are characterized by several variables. The initial modulus is the resistance to elongation at the onset of stretching. This quantity is simply the slope at the beginning of the stress-strain curve. Upon overstretching, the polymer sample eventually ruptures. The rupture point yields two important measurements, the tensile strength ($T_b$) and the ultimate elongation ($E_b$). These values are the stress and percent elongation at the break, respectively. The tensile set (TS) is the elongation remaining in a polymer sample after it is stretched to 300% elongation and allowed to recover. An additional measure of the reversibility of stretching is the percent recovery (PR), which is given by the equation: 100(final length−initial length)/(initial length).

It is believed that the elastomeric properties of the polypropylenes of this invention are due to an alternating block structure comprising of isotactic and hemiisotactic stereosequences. Without being bound by theory, it is believed that isotactic block stereosequences provide crystalline blocks which can act as physical crosslinks in the polymer network.

The structure of the polymer can be described in terms of the isotactic pentad content [mmmm] which is the percentage of isotactic stereosequences of 5 contiguous stereocenters, as determined by $^{13}C$ NMR spectroscopy (Zambelli, A. et al. 1975. Macromolecules 8, 687-689). The isotactic pentad content of statistically atactic polypropylene is approximately 6.25%, while that of highly isotactic polypropylene can approach 100%. Polymers also can be characterized for their isotactic percent (m).

While it is possible to produce polypropylenes with a range of isotactic pentad contents, the elastomeric properties of the polymer will depend on the distribution of isotactic (crystalline) and atactic (amorphous) stereosequences. Thermoplastic elastomers consist of amorphous-crystalline block polymers, and thus the blockiness of the polymer determines whether it will be elastomeric.

The structure, and therefore the properties of the obtained polypropylenes also depend on the nature of the ligand bound to the transition metal.

It will be appreciated from the illustrative examples that this catalyst system provides an extraordinary broad range of polymer properties from the polymerization process of this invention.

Polyolefins can be obtained by suitable manipulation of the metallocene catalyst, the reaction conditions, or the cocatalyst to give polymers which range in properties from gum elastomers to thermoplastic elastomers to flexible thermoplastics, and indeed, to relatively rigid thermoplastics.

The polymers of the present invention in one embodiment are a novel class of thermoplastic elastomers made up of propylene homopolymers of weight average molecular weights ranging from 20,000 to above about 2 million. Preferably, the average molecular weights of the polypropylenes are very high, as molecular weights on the average of 1,000,000 are readily obtainable and even higher $M_w$ are indicated. The molecular weight distributions of the polymers are quite low, with typical polydispersities, $M_w/M_n$, ranging from about 1.8 to about 4.4, and more preferably can be controlled to be in the range of about 1.8 to about 2.4. However, by control of reaction conditions, higher molecular weight distributions also can be obtained, e.g., polydispersities of 5–20 are easily produced. The elastomeric polypropylenes of the present invention have isotactic pentad contents ranging from an [mmmm] content of about 25% to an [mmmm] of about 50%. The polypropylenes of the present invention range from amorphous atactic polypropylenes with no melting point, to elastomeric polypropylenes of high crystallinity with melting points up to about 160° C.

Accordingly, because of the wide range of structures and crystallinities, the polypropylenes of the present invention exhibit a range of properties from gum elastomers, to thermoplastic elastomers, to flexible thermoplastics. The range of elastomeric properties for the polypropylenes is quite broad. Properties of particular polymers of the invention are listed in the Tables.

The polypropylenes of the present invention can be melt spun into fibers, or can be cast into transparent, tough, self-supporting films with good elastic recoveries. Thin films of elastomeric polypropylenes with isotactic pentad contents [mmmm]=30% are slightly opaque, but exhibit stress-whitening upon extension, which may be indicative of stress-induced crystallization. The elastomeric polypropylenes can also be cast into molded articles.

The elastomeric polypropylenes of the present invention can be blended with isotactic polypropylenes, including isotactic polypropylenes of the invention. The melting points and heats of fusion of the blends increase steadily with increasing mole fraction of isotactic polypropylene in the blend.

The utility of the polymers of the present invention are evident and quite broad, including films, adhesives, resilient and elastomeric objects. As they are completely compatible with isotactic polypropylene, they are ideal candidate additives to improve the toughness and impact strength of isotactic polypropylenes.

Isotactic Polyolefins

This invention describes a new material synthesized from $C_2$ to $C_{10}$ alk-1-enes by a catalyst system. The polymer formed is a thermoplastic [1] and has the general microstructure and tacticity depicted by formula (IV):

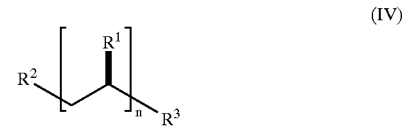

(IV)

in which R1 is $C_1$ to $C_8$ alkyl, 3 to 10 membered cycloalkyl, $C_6$ to $C_{20}$ aryl, alkylaryl, arylalkyl, fluoroalkyl, or fluoroaryl having 1 to 10 carbons in the alkyl moiety and 6 to 20 carbon atoms in the aryl moiety, $Si(R^4)_3$ where $R^4$ is a $C_1$ to $C_{10}$ alkyl, or —$OR^5$ where $R^5$ is hydrogen, $C_1$ to $C_{10}$ alkyl or $C_6$ to $C_{20}$ aryl; $R^2$ and $R^3$ are independently hydrogen, $C_1$ to $C_{10}$ alkyl, $C_2$ to $C_{10}$ alkenyl, or $OR^5$; n is greater than 0.

The preferred isotactic polymer structure is polyolefin IV wherein $R^1$ is methyl, $R^2$ is hydrogen, ethenyl, isopropyl, or isopropenyl, and $R^3$ is hydrogen or methyl. The preferred n is greater than 0. The preferred polymer tacticity is thus isotactic. The preferred thermo-mechanical properties of the polymer are those of a thermoplastic.

This new polymer may be prepared via monomer polymerization processes that occur homogeneously in solution, supported in a solution, in the gas phase, at high pressure, or in bulk monomer, including the condensed phase of lower molecular weight alk-1-enes. The preferred processes are bulk monomer and gas phase polymerization methods. Catalyst systems may be organometallic compounds containing a metal of the III, IV, or V subgroup of the periodic system, or a metal from the lanthamide or actinide groups, activated by systems which may be alkylaluminums, haloalkylaluminums, alkylaluminoxanes or ionic activators. The preferred organometallic precatalysts are (methyl)$_2$C(3-(2-methyl-2-adamantyl)cyclopentadienyl) (fluorenyl) zirconium dichloride (71, "$R_2C(Cp^1)(Flu^1)$zirconium dichloride") and (methyl)$_2$C(3-(2-methyl-2-adamantyl) cyclopentadienyl) (octamethyloctahydrodibenzofluorenyl) zirconium dichloride (72, "$R_2C(Cp^2)(Oct^1)$zirconium dichloride"). The preferred activators are methylaluminoxane and activators which contain boron.

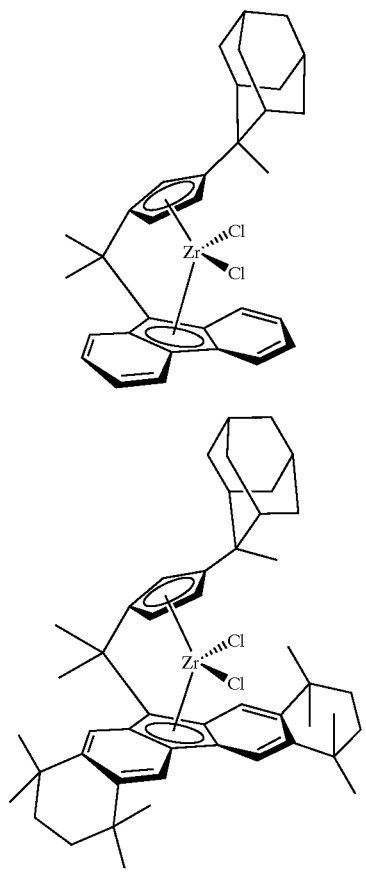

Most preferably, the produced polyolefin will be a high melting thermoplastic. Polymerization of two or more monomers may be employed to produce copolymers or terpolymers. Combinations of two or more metallocene catalyst precursors may be used to prepare a blend of polymers. The polymers, copolymers, and terpolymers prepared according to this invention may be blended with existing, commercial polyolefins.

Isotactic polymers produced with the catalysts of the invention have catalytic dyad (mm) contents of at least about 98% and can have mm content of >99%. Catalysts of the invention are particularly suited to the production of isotactic polypropylene.

Syndiotactic Polyolefins

This invention also describes a new material synthesized from $C_2$ to $C_{10}$ alk-1-enes by a catalyst system. The polymer formed is a thermoplastic[1,2] and has the general microstructure and tacticity depicted by formula (I)

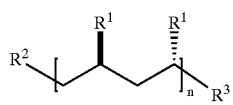
(V)

in which $R^1$ is $C_1$ to $C_8$ alkyl, 3 to 10 membered cycloalkyl, $C_6$ to $C_{20}$ aryl, alkylaryl, arylalkyl, fluoroalkyl, or fluoroaryl having 1 to 10 carbons in the alkyl moiety and 6 to 20 carbon atoms in the aryl moiety, $Si(R^4)_3$ where $R^4$ is a $C_1$ to $C_{10}$ alkyl, or —$OR^5$ where $R^5$ is hydrogen, $C_1$ to $C_{10}$ alkyl or $C_6$ to $C_{20}$ aryl; $R^2$ and $R^3$ are independently hydrogen, $C_1$ to $C_{10}$ alkyl, $C_2$ to $C_{10}$ alkenyl, or $oR^5$; n is greater than 0.

The preferred polymer structure is polyolefin V wherein $R^1$ is methyl, $R^2$ is hydrogen, ethenyl, isopropyl, or isopropenyl, and $R^3$ is hydrogen or methyl. The preferred n is greater than 0. The preferred polymer tacticity is thus syndiotactic. The preferred thermo-mechanical properties of the polymer are those of a thermoplastic.

Method of Preparing Syndiotactic Polyolefins

This new polymer may be polymerized via monomer polymerization processes that occur homogeneously in solution, supported in a solution, in the gas phase, at high pressure, or in bulk monomer, including the condensed phase of lower molecular weight alk-1-enes. The preferred processes are bulk monomer and gas phase polymerization methods. Catalyst systems may be organometallic compounds containing a metal of the III, IV, or V subgroup of the periodic system, or a metal from the lanthamide or actinide groups, activated by systems which may be alkylaluminums, haloalkylaluminums, alkylaluminoxanes or ionic activators. The preferred organometallic precatalysts are $(methyl)_2C$ (cyclopentadienyl) (octamethyloctahydrodibenzofluorenyl) zirconium dichloride (91) and $(phenyl)_2C$(cyclopentadienyl) (octamethyloctahydrodibenzofluorenyl)zirconium dichloride (92). The preferred activators are methylaluminoxane and activators which contain boron.

Most preferably, the produced polyolefin will be a high melting thermoplastic. Polymerization of two or more monomers may be employed to produce copolymers or terpolymers. Combinations of two or more metallocene catalyst precursors may be used to prepare a blend of polymers. The polymers, copolymers, and terpolymers prepared according to this invention may be blended with existing, commercial polyolefins.

Elastomeric Polyolefins

This invention describes a new material synthesized from $C_2$ to $C_{10}$ alk-1-enes by a catalyst system. The polymer formed is a thermoplastic elastomer[1] and has the general microstructure and tacticity depicted by formula (Z)

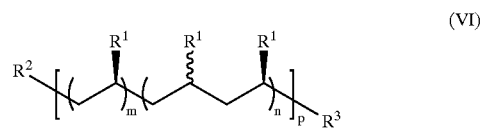
(VI)

in which $R^1$ is $C_1$ to $C_8$ alkyl, 3 to 10 membered cycloalkyl, $C_6$ to $C_{20}$ aryl, alkylaryl, arylalkyl, fluoroalkyl, or fluoroaryl having 1 to 10 carbons in the alkyl moiety and 6 to 20 carbon atoms in the aryl moiety, $Si(R^4)_3$ where $R^4$ is a $C_1$ to $C_{10}$ alkyl, or —$OR^5$ where $R^5$ is hydrogen, $C_1$ to $C_{10}$ alkyl or $C_6$ to $C_{20}$ aryl; $R^2$ and $R^3$ are independently hydrogen, $C_1$ to $C_{10}$ alkyl, $C_2$ to $C_{10}$ alkenyl, or $OR^5$; m, n, and p are each greater than 0.

The preferred elastomeric polymer structure is polyolefin VI wherein $R^1$ is methyl, $R^2$ is hydrogen, ethenyl, isopropyl, or isopropenyl, and $R^3$ is hydrogen or methyl. The preferred m is greater than 5 but less than 50% of the degree of polymerization, which is given by $(P)\cdot(m_{average}+2n_{average})$. The preferred n is greater than 5 but less than 25% of the degree of polymerization. The preferred p is greater than 0. The preferred polymer tacticity is thus stereoblock isotactic-hemiisotactic. The preferred thermo-mechanical properties of the polymer are those of a thermoplastic elastomer.

This new polymer may be polymerized via monomer polymerization processes that occur homogeneously in solution, supported in a solution, in the gas phase, at high pressure, or in bulk monomer, including the condensed phase of lower molecular weight alk-1-enes. The preferred processes are bulk monomer and gas phase polymerization methods. Catalyst systems may be organometallic compounds containing a metal of the III, IV, or V subgroup of the periodic system, or a metal from the lanthamide or actinide groups, activated by systems which may be alkylaluminums, haloalkylaluminums, alkylaluminoxanes or ionic activators. The preferred organometallic precatalysts are (methyl)$_2$C(3-(2-adamantyl)cyclopentadienyl) (fluorenyl)zirconium dichloride (91) and (phenyl)$_2$C(3-(2-adamantyl)cyclopentadienyl) (fluorenyl)zirconium dichloride (92). The preferred activators are methylaluminoxane and activators which contain boron.

Most preferably, the produced polyolefin will be a thermoplastic elastomer containing alternating isotactic and hemiisotactic stereoblocks. Polymerization of two or more monomers may be employed to produce copolymers or terpolymers. Combinations of two or more metaliocene catalyst precursors may be used to prepare a blend of polymers. The polymers, copolymers, and terpolymers prepared according to this invention may be blended with existing, commercial polyolefins.

Activators

Appropriate activators for use with the metallocene catalysts of the invention include alkylaluminum compounds, methylaluminoxane, or modified methylaluminoxanes of the type described in the following references: U.S. Pat. No. 4,542,199 to Kaminsky, et al; Ewen, J. Am. Chem. Soc., 106 (1984), p. 6355; Ewen, et al., J. Am. Chem. Soc. 109 (1987) p. 6544; Ewen, et al, J. Am. Chem. Soc. 110 (1988), p. 6255.; Kaminsky, et al., Angew. Chem., Int. Ed. Eng. 24 (1985), p. 507. Other cocatalysts which may be used include Lewis or protic acids, which generate cationic metallocenes with compatible non-coordinating anions for example B(C$_6$F$_5$)$_3$ or [PhNMe$_2$H]$^+$B(C$_6$F$_5$)$_4^-$ in the presence or absence of alkylaluminum compounds. Catalyst systems employing a cationic Group 4 metallocene and compatible non-coordinating anions are described in European Patent Applications 277,003 and 277,004 filed on 27.01.88 by Turner, et al.; European Patent Application 427,697-A2 filed on 09.10.90 by Ewen, et al.; Marks, et al., J. Am. Chem. Soc., 113 (1991), p. 3623; Chien et al., J. Am. Chem. Soc., 113 (1991), p. 8570; Bochman et al., Angew. Chem. Intl. Ed. Engl. 7 (1990), p. 780; and Teuben et al., Organometallics, 11 (1992), P. 362, and references therein.

Utility

As thermoplastics, these new materials may be processed via methods including injection molding, extrusion, or blow molding and may have applications that take advantage of its mechanical behavior and mechanical properties, including its tensile strength, rigidity and impact strength. Additional properties of this material may include recyclability, chemical resistivity, thermal stability, electrical conductivity, optical transparency, and processability.

DETAILED DESCRIPTION

Definitions

The term "alkyl" as used herein refers to a branched or unbranched saturated hydrocarbon group of 1 to 24 carbon atoms, for example methyl, ethyl, n-propyl, isopropyl, n-butyl, isobutyl, t-butyl, octyl, decyl, tetradecyl, hexadecyl, eicosyl, tetracosyl and the like, as well as cycloalkyl groups for example cyclopentyl, cyclohexyl and the like. The term "lower alkyl" intends an alkyl group of 1 to 6 carbon atoms, preferably 1 to 4 carbon atoms. Alkyl substituents includes optionally substituted.

The term "cycloalkyl" as used herein refers to a cyclic hydrocarbon of 4 to 10 carbon atoms forming a ring, including bicyclic systems.

The term "substituted cycloalkyl" as used herein refers to a cycloalkyl ring having substituents on said ring of alkyl, alkoxy, "Substituted cycloalkyl" includes substitution with from 1 to 10 carbons at each ring position, with a total number of carbon substitutions in the range of 1 to 30.

A "cyclic group" is a ring composed of 4 to 10 atoms selected from carbon, silicon, oxygen, sulfur, selenium, and germanium.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing one to six, more preferably one to four, carbon atoms.

The term "aryl" as used herein refers to an aromatic species containing 1 to 5 aromatic rings, either fused or linked, and either unsubstituted or substituted with 1 or more substituents typically selected from the group consisting of —(CH$_2$)$_x$—NH$_2$, —(CH$_2$)$_x$—COOH, —NO$_2$, halogen and lower alkyl, where x is an integer in the range of 0 to 6 inclusive as outlined above. Preferred aryl substituents contain 1 to 3 fused aromatic rings, and particularly preferred aryl substituents contain 1 aromatic ring or 2 fused aromatic rings. The term "aralkyl" intends a moiety containing both alkyl and aryl species, typically containing less than about 24 carbon atoms, and more typically less than about 12 carbon atoms in the alkyl segment of the moiety, and typically containing 1 to 5 aromatic rings. The term "aralkyl" will usually be used to refer to aryl-substituted alkyl groups. The term "aralkylene" will be used in a similar manner to refer to moieties containing both alkylene and aryl species, typically containing less than about 24 carbon atoms in the alkylene portion and 1 to 5 aromatic rings in the aryl portion, and typically aryl-substituted alkylene. Exemplary aralkyl groups have the structure —(CH$_2$)$_j$—Ar wherein j is an integer in the range of 1 to 24, more typically 1 to 6, and Ar is a monocyclic aryl moiety.

"Halo" or "halogen" refers to fluoro, chloro, bromo or iodo, and usually relates to halo substitution for a hydrogen atom in an organic compound. Of the halos, chloro and fluoro are generally preferred.

"Hydrocarbyl" refers to unsubstituted and substituted hydrocarbyl radicals containing 1 to about 20 carbon atoms, including branched or unbranched, saturated or unsaturated species, for example alkyl groups, alkenyl groups, aryl groups, and the like. The term "lower hydrocarbyl" intends a hydrocarbyl group of one to six carbon atoms, preferably one to four carbon atoms.

"Optional" or "optionally" means that the subsequently described event or circumstance may or may not occur, and that the description includes instances where said event or circumstance occurs and instances where it does not. For example, the phrase "optionally substituted alkyl" means that an alkyl moiety may or may not be substituted and that the description includes both unsubstituted alkylene and alkylene where there is substitution.

Substitution of an alkyl, aryl or other hydrocarbon means that a hydrogen of the hydrocarbon is substituted with another atom or group of atoms. Such atoms include halogens. Groups of atoms can by alkyl substituents, aryl substituents, aralkyl, alkoxy and the like substituents.

Methods of Preparing Catalysts

Metallocenes Containing the Fluorene Ligand

Substituted fulvene [Fulvene[1]] can be prepared by known methods. The anion [Flu[1]]$^-$ is prepared by treatment of

[Flu¹]H with alkali metal-alkyls or Grignard reagents in a solvent to give the corresponding substituted fluorenyl anion.

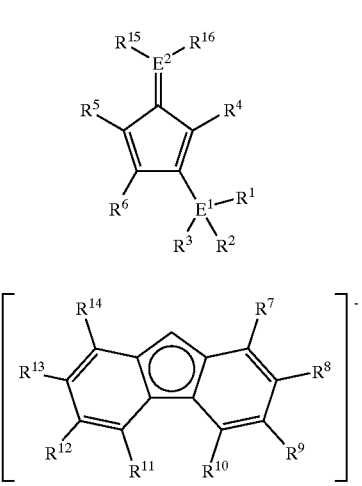

In a solvent, $R^{15}R^{16}E^2(Flu^1H)(Cp^1H)$ is formed by combining [Fulvene1] and [Flu¹]⁻, followed by quenching with a proton source, for example water.

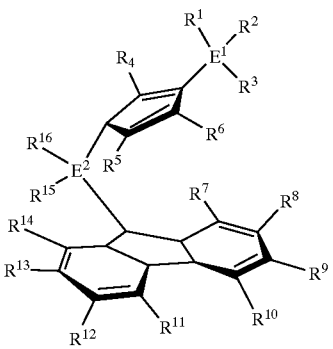

$R^{15}R^{16}E^2(Flu^1H)(Cp^1H)$

The dianion of $R^{15}R^{16}E^2(Flu^1H)(Cp^1H)$ is formed by treatment with alkali metal-alkyls or Grignard reagents in a solvent: $[R^{15}R^{16}E^2(Flu^1)(Cp^1)]^{-2}$. Reaction of this dianion with $MX_{n+2}$ in a solvent produces compound (II), which is isolated according to known methods.

Metallocenes Containing the Octamethyloctahydrodibenzofluorene Ligand 1,1,4,4,7,7,10,10-octamethyl-1,2,3,4,7,8,9,10-octahydro dibenzo[b, h] fluorene (OctH) is prepared by the reaction of two equivalents of 2,5-dichloro-2,5-dimethylhexane with one equivalent of fluorene in a solvent in the presence of a Friedel-Crafts initiator.

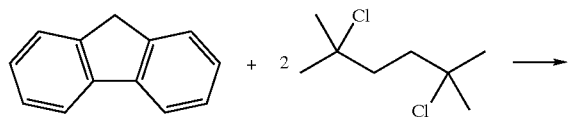

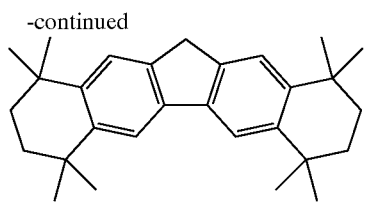

OctH

Substituted fulvene [Fulvene 2] can be prepared by known methods. The anion [Oct¹]⁻ is prepared by treatment of [Oct¹]H with alkali metal-alkyls or Grignard reagents in a solvent to give the corresponding substituted octamethyloctahydrodibenzofluorenyl anion.

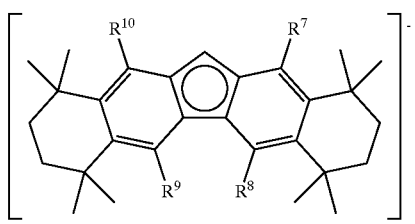

In a solvent, $R^{11}R^{12}E^2(Oct^1H)(Cp^2H)$ is formed by combining [Fulvene²] and [Oct¹]⁻, followed by quenching with a proton source, for example water.

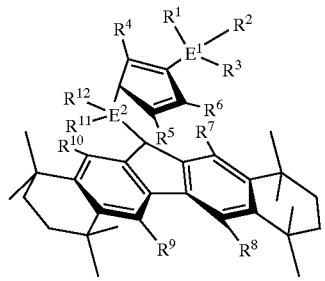

$R^{11}R^{12}E^2(Oct^1H)(Cp^2H)$

The dianion of $R^{11}R^{12}E^2$ $(Oct^1H)(Cp^2H)$ is formed by treatment with alkali metal-alkyls or Grignard reagents in a solvent: $[R^{11}R^{12}E^2(Oct^1)(Cp^2)]^{-2}$. Reaction of this dianion with $MX_{n+2}$ in a solvent produces compound (III), which is isolated according to known methods.

EXAMPLES

1. Polymerization Catalysts

Unless otherwise noted, all reactions and procedures are carried out under an inert atmosphere of argon or nitrogen using standard glove box, Schlenk and high vacuum line techniques. Solvents are dried according to standard procedures.

Examples 1–12
Examples 1–12 describe the synthesis of catalyst systems designed to produce elastomeric polymers, and particularly describe the synthesis of elastomeric polypropylenes.
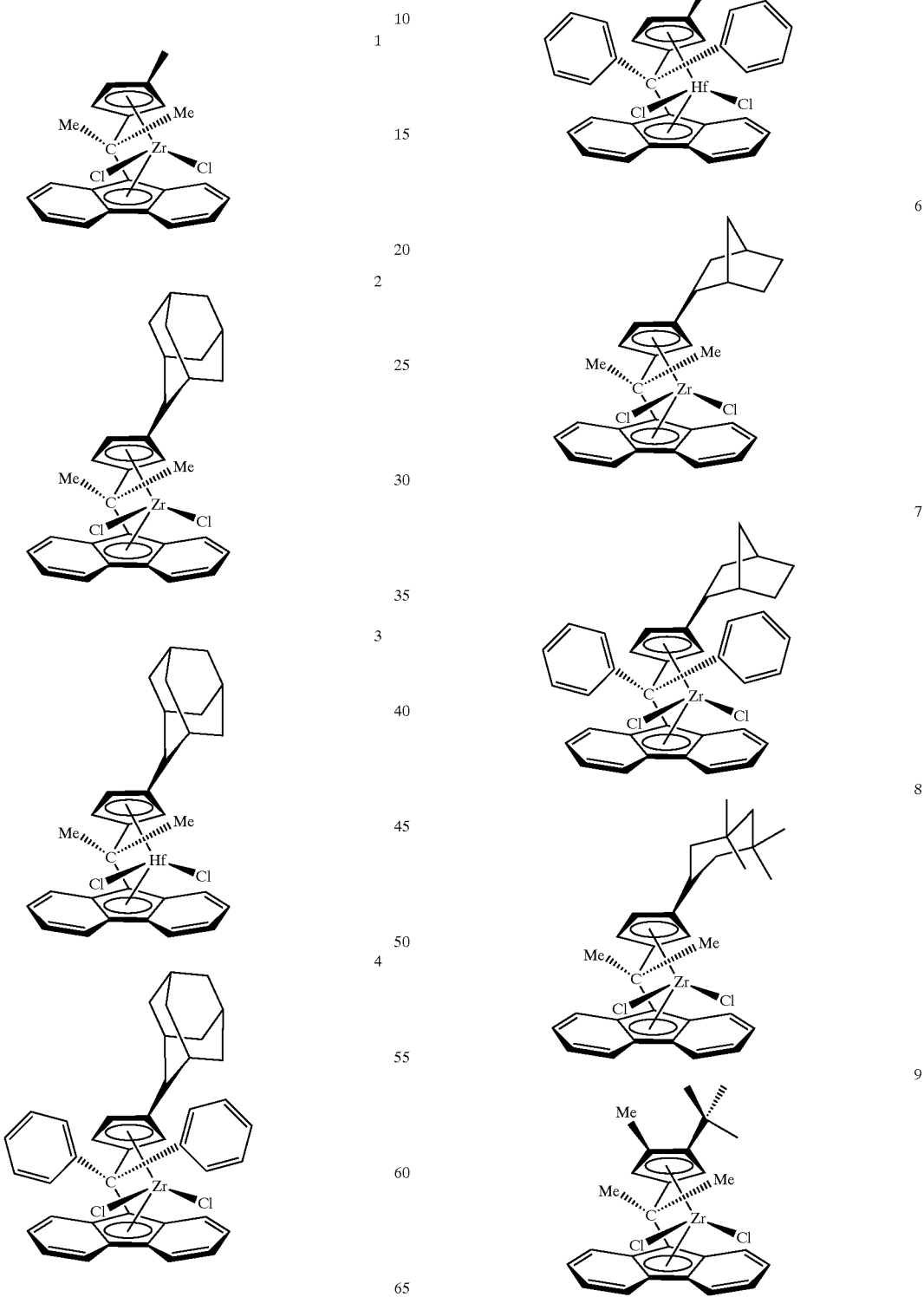

Example 1
Preparation of 1.

The synthesis of 1 was performed as described in the literature.[9, 10]

Example 2
Preparation of 2.

6,6'-(tricyclo[3.3.1.1]decane)fulvene (adamantylfulvene). (Synthesis modified from reference 20) Pyrrolidine (10.0 mL, 0.116 mol) was syringed into a solution of 2-adamantanone (25.00 g, 0.1664 mol) and cyclopentadiene (30.0 mL, 0.364 mol) in 250 mL of methanol. The reaction was stirred for 92 hours before the yellow precipitate was collected by suction filtration, rinsed with a small volume of methanol and dried in vacuo. 25.71 grams (77.9%) of adamantylfulvene were isolated. MS (GC-MS) m/z 198.3 (M$^+$). $^1$H NMR (CDCl$_3$): δ 1.93–2.08, 3.29 (m, 14H, adamantyl-H), 6.52, 6.60 (m, 4H, fulvene-H). $^{13}$C NMR (CDCl$_3$): δ 28.30, 37.05, 37.35, 40.25 (adamantyl-C), 119.47, 130.47 (fulvene-CH$_1$), 135.81, 167.38 (fulvene-CH$_0$). Elemental analysis calculated for C$_{15}$H$_{18}$: C, 90.85; H, 9.15. Found: C, 90.20, 90.22; H, 8.39, 8.50.

2-adamantylcyclopentadiene. 6.00 grams (30.3 mmol) of adamantylfulvene were dissolved in 30 mL of tetrahydrofuran and this solution added over 30 minutes to a stirred slurry of LiAlH$_4$ (1.40 g, 0.0369 mol) at 0° C. After 5 hours of stirring at room temperature, the reaction was cooled to 0° C. and quenched by slow addition of 20 mL of saturated NH$_4$Cl solution. Then 300 mL H$_2$O, 25 mL concentrated HCl, and 50 mL diethyl ether were added, the organic layer isolated, and the aqueous layer extracted with additional diethyl ether (3×50 mL). The combined organic layers were dried over MgSO$_4$, filtered, and rotavapped to give the product, 2-adamantylcyclopentadiene, in quantitative yield as a light yellow oil. MS (GC-MS) m/z 200.3 (M$^+$).

3-(2-adamantyl)-6,6-dimethylfulvene. To 2-adamantylcyclopentadiene (6.06 g, 30.3 mmol) was added 50 mL methanol, 50 mL ethanol, 20 mL tetrahydrofuran, 36 mL acetone (0.49 mol) and 0.5 mL pyrrolidine (0.006 mol). After stirring for 48 hours, 5 mL of acetic acid were injected, followed by 200 mL H$_2$O and 200 mL diethyl ether. The organic layer was isolated and the aqueous layer extracted with diethyl ether (3×40 mL). The combined organic layers were extracted with H$_2$O (3×25 mL) and with 10% aqueous NaOH (3×25 mL), dried over MgSO$_4$, filtered and rotavapped. The obtained yellow solid was further purified by overnight Soxhlet extraction by 150 mL methanol. The precipitate in the filtrate was isolated by filtration at 0° C., and in vacuo drying: 4.54 g (62.5%) of 3-(2-adamantyl)-6,6-dimethylfulvene, as a yellow powder. Elemental analysis calculated for C$_{18}$H$_{24}$: C, 89.94; H, 10.06. Found: C, 82.23, 82.23; H, 8.78, 8.82.

Me$_2$C(3-(2-adamantyl)C$_5$H$_3$)(C$_{13}$H$_8$)H$_2$. 10.5 mL of an n-butyllithium solution (1.6 M in hexanes, 0.0168 mol) were syringed into a solution of fluorene (2.77 g, 0.0166 mol) in 60 mL tetrahydrofuran. After stirring for 5 hours, a solution of 3-(2-adamantyl)-6,6-dimethylfulvene (4.00 g, 0.0166 mol) in 40 mL tetrahydrofuran was injected over 2 minutes. After stirring for 20 hours, 60 mL of a saturated NH$_4$Cl solution were added, the organic layer isolated, and the aqueous layer extracted with diethyl ether (2×25 mL). The combined organic layers were dried over MgSO$_4$, filtered and rotavapped to give the product in quantitative yield as a yellow oil.

Me$_2$C(3-(2-adamantyl)C$_5$H$_3$)(C$_{13}$H$_8$)Li$_2$. The dianion was prepared by treating a solution of Me$_2$C(3-(2-adamantyl)C$_5$H$_3$)(C$_{13}$H$_8$)H$_2$ (6.77 g, 16.6 mmol) in 75 mL diethyl ether with 22.0 mL of n-butyllithium solution (1.6 M in hexanes, 0.0352 mol) at 0° C. After stirring for 21 hours, the solvent was removed by vacuum transfer and 50 mL of petroleum ether were condensed in. The dilithio salt was isolated by filtration and in vacuo drying in quantitative yield as an orange powder.

Me$_2$C(3-(2-adamantyl)C$_5$H$_3$)(C$_{13}$H$_8$)ZrCl$_2$ (2). 2.00 grams of Me$_2$C(3-(2-adamantyl)C$_5$H$_3$)(C$_{13}$H$_8$)Li$_2$ (0.00478 mol) and 1.114 g ZrCl$_4$ (0.00478 mol) were combined in a swivel frit apparatus. 40 mL of petroleum ether were condensed in at −78° C. This was allowed to warm slowly to room temperature before solvent removal after 14 hours of stirring. 40 mL of methylene chloride were condensed in and removed in order to quench unreacted ligand. Then the orange solid was extracted in the swivel frit with 50 mL of refluxing diethyl ether. Two crops were obtained for a total of 1.502 grams (55.5%) of 2 as an orange powder following collection at 0° C. and in vacuo drying. MS (LC-MS) m/z 566.5 (M$^+$). $^1$H NMR (C$_6$D$_6$): δ 1.36–2.04 (m, 14H, adamantyl-H), 1.84, 1.86 (s, 6H, C(CH$_3$)$_2$), 3.32 (s, 1H, 2-H-adamantyl), 5.44, 5.48, 6.18 (m, 3H, Cp-H), 6.95, 7.03, 7.29, 7.34 (t, $^3$J$_{HH}$=7.7, 7.7, 8.0, 8.0 Hz, 4H, Flu-H), 7.41, 7.49, 7.84, 7.84 (d, $^3$J$_{HH}$=8.8, 9.1, 7.7, 7.7 Hz, 4H, Flu-H). $^{13}$C NMR (CD$_2$Cl$_2$): δ 28.58, 28.65 (C-(CH$_3$)$_2$), 27.90, 27.93, 31.98, 32.41, 32.62, 32.66, 37.84, 38.50, 38.66, 43.83 (adamantyl-C), 102.56, 103.02, 116.65 (Cp-CH$_1$), 123.41, 123.67, 124.61, 124.67, 124.76, 124.83, 128.81, 128.81 (Flu-CH$_1$), 139.93 (9-Flu-C),CH$_0$ not determined. Elemental analysis calculated for C$_{31}$H$_{32}$Zr$_1$Cl$_2$: C, 65.70; H, 5.69. Found: C, 63.46, 61.93; H, 5.57, 5.42.

Example 3
Preparation of 3.

Me$_2$C(3-(2-adamantyl)C$_5$H$_3$)(C$_{13}$H$_8$)HfCl$_2$ (3). 2.00 grams of Me$_2$C(3-(2-adamantyl)C$_5$H$_3$)(C$_{13}$H$_8$)Li$_2$ (4.78 mmol) and 1.531 g HfCl$_4$ (4.78 mol) were combined in a 100 mL flask equipped with a 180° needle valve. 50 mL of petroleum ether were condensed in at −78° C. This was allowed to warm slowly to room temperature before solvent removal after 47 hours of stirring. 20 mL of methylene chloride were condensed in and removed in order to quench unreacted ligand. Then the yellow solid was extracted in cellulose extraction thimble with 150 mL of refluxing methylene chloride for 48 hours. Solvent was removed from the filtrate and 30 mL diethyl ether were condensed in. The yellow solid was collected on the frit and dried in vacuo: 1.771 g (56.7%). MS (LC-MS) m/z 654.7 (M$^+$). $^1$H NMR (C$_6$D$_6$): δ 1.11–2.04 (m, 14H, adamantyl-H), 1.85, 1.88 (s, 6H, C(CH$_3$)$_2$), 3.37 (s, 1H, 2-H-adamantyl), 5.40, 5.43, 6.12 (m, 3H, Cp-H), 6.94, 7.01, 7.27, 7.33 (t, $^3$J$_{HH}$=7.0, 7.7, 7.0, 7.3 Hz, 4H, Flu-H), 7.46, 7.55, 7.84, 7.84 (d,3J$_{HH}$=8.8, 8.8, 8.4, 8.4 Hz, 4H, Flu-H). $^{13}$C NMR (CD$_2$Cl$_2$): δ 28.82, 28.88 (C-(CH$_3$)$_2$), 27.90, 27.90, 32.08, 32.40, 32.65, 32.70, 37.86, 38.53, 38.68, 43.77 (adamantyl-C), 99.90, 100.22, 115.73 (Cp-CH$_1$), 123.16, 123.42, 124.27, 124.42, 124.54, 124.66, 128.61, 128.64 (Flu-CH$_1$), 138.42 (9-Flu-C),CH$_0$ not determined. Elemental analysis calculated for C$_3$,H-$_{32}$Hf$_1$Cl$_2$: C, 56.93; H, 4.93. Found: C, 54.80; H, 4.97.

Example 4
Preparation of 4.

adamantylfulvene. (Synthesis modified from reference 20) 2-adamantanone (40.22 g, 267.7 mmol), methanol (200 mL), cyclopentadiene (51.0 mL, 618.9 mmol), and pyrrolidine (20.0 mL, 239.6 mmol) were added to a 1 liter round bottom flask. After stirring for 70 hours, the yellow precipitate was collected by suction filtration and washed with 50 mL methanol. After in vacuo drying, 45.59 grams adamantylfulvene were obtained (85.9%). MS (GC-MS) m/z 198.3 (M$^+$).

2-adamantylcyclopentadiene. A 500 mL argon-purged round bottom flask was charged with LiAlH$_4$ (8.20 g, 216 mmol) and 100 mL tetrahydrofuran. Adamantylfulvene (30.00 g, 151.3 mmol) was added via solid addition funnel, followed by another 100 mL tetrahydrofuran over 2 minutes at 0° C. After stirring for 22 hours at room temperature, the reaction was cooled to 0° C. and 100 mL water were added dropwise over 60 minutes. Then, 100 mL concentrated aqueous HCl in 300 mL water and 50 mL diethyl ether were added. The organic layer was isolated and the aqueous layer extracted with diethyl ether (3×50 mL). The combined organic layers were dried over MgSO$_4$, filtered, and rotavapped to give 30.30 g of product in quantitative yield. MS (GC-MS) m/z 200.3 (M$^+$).

3-(2-adamantyl)-6,6-diphenylfulvene. A 250 mL round bottom flask was charged with 2-adamantylcyclopentadiene (10.24 g, 51.13 mmol), benzophenone (9.32 g, 51.13 mmol) and 100 mL absolute ethanol. Once the solids had dissolved, sodium methoxide (5.00 g, 92.6 mmol) was added and the reaction was stirred for five days. The orange precipitate was collected by suction filtration and washed with 50 mL ethanol. The air dried product was stirred in 100 methanol overnight and the solid was collected by suction filtration and washed with 50 mL methanol. Drying in vacuo for several hours provided 13.32 grams of desired product (71.5%). MS (GC-MS) m/z 364.5 (M$^+$). Elemental analysis calculated for $C_{28}H_{28}$: C, 92.26; H, 7.74. Found: C, 87.05; H, 6.92.

Ph$_2$C(3-(2-adamantyl)C$_5$H$_3$)(C$_{13}$H$_8$)H$_2$. In the glove box, a 250 mL round bottom flask was charged with 3-(2-adamantyl)-6,6-diphenylfulvene (6.000 g, 16.46 mmol) and fluorenyllithium diethyl ether adduct (4.054 g, 16.46 mmol). This was equipped with a 180° needle valve and 100 mL of diethyl ether were condensed into the reaction vessel. After stirring at room temperature for 7 days, 60 mL of aqueous NH$_4$Cl and 50 mL water were slowly added. After 2 hours, the solid that formed was collected by filtration and washed with 40 mL diethyl ether. The crude, wet product was dissolved in 250 mL tetrahydrofuran, dried over MgSO$_4$, filtered, rotavapped, and dried in vacuo to give 2.834 grams of a waxy solid as the product (32.4%). MS (GC-MS) m/z 530.6 (M$^+$).

Ph$_2$C(3-(2-adamantyl)C$_5$H$_3$)(C$_{13}$H$_8$)ZrCl$_2$ (4). 2.834 grams of Ph$_2$C(3-(2-adamantyl)C$_5$H$_3$)(C$_{13}$H$_8$)H$_2$ (5.340 mmol) were combined with LiCH$_2$(trimethylsilane) (1.006 g, 10.68 mmol) in a 250 mL round bottom flask. 50 mL of tetrahydrofuran were condensed in and this was stirred at room temperature for 17 hours, when the solvent was removed. In the glove box, zirconium tetrachloride (1.245 g, 5.343 mmol) was added. 60 mL of petroleum ether were condensed in and the reaction stirred at room temperature for 52 hours. Solvent was removed and 20 mL of dichloromethane were condensed in, stirred, and removed. Then, 50 mL of diethyl ether were condensed in, stirred, and removed. The solid was extracted overnight in a cellulose extraction thimble with 150 mL methylene chloride. The obtained solution was filtered through a frit. Solvent was removed, 15 mL of diethyl ether were condensed in, and the orange solid was broken up, collected at 0° C., and dried in vacuo to give 0.778 grams of product 3 (21.1%). MS (LC-MS) m/z 690.9 (M$^+$). Elemental analysis calculated for $C_{41}H_{36}Zr_1Cl_2$: C, 71.28; H, 5.25. Found: C, 68.78; H, 5.21.

Example 5

Alternate Preparation of 4.

adamantylfulvene. (Synthesis modified from reference 20) 2-adamantanone (45.00 g, 299.6 mmol), methanol (200 mL), cyclopentadiene (60.0 mL, 728 mmol), and pyrrolidine (20.0 mL, 240 mmol) were added to a 1 liter round bottom flask. After stirring for 77 hours, the yellow precipitate was collected by suction filtration and washed with 50 mL methanol. After in vacuo drying, 49.56 grams adamantylfulvene were obtained (83.4%). MS (GC-MS) m/z 198.3 (M$^+$).

2-adamantylcyclopentadiene. A 500 mL argon-purged round bottom flask was charged with LiAlH$_4$ (9.00 g, 237 mmol) and 400 mL diethyl ether. Adamantylfulvene (31.05 g, 156.6 mmol) was added as solid over 2 minutes at 0° C. After stirring for 15 hours at room temperature, the reaction was cooled to 0° C. and 60 mL water were added dropwise over 2 hours, along with 300 mL diethyl ether. The alumina residue was removed by gravity filtration and rinsed with an additional 100 mL diethyl ether. The organic layer was rotavapped to give 30.18 g of product (96.2%) as a light yellow oil.

3-(2-adamantyl)-6,6-diphenylfulvene. A 500 mL round bottom flask containing 2-adamantylcyclopentadiene (30.18 g, 150.7 mmol) was added benzophenone (27.50 g, 150.9 mmol) and 300 mL absolute ethanol. Once the solids had dissolved, sodium methoxide (15.00 g, 278 mmol) was added and the reaction was stirred for six days. The orange precipitate was collected by suction filtration and the air dried product was then stirred in 100 methanol for two days before the solid was collected by suction filtration and washed with 100 mL methanol. Drying in vacuo for two days provided 25.72 grams of desired product (46.8%). And second crop was obtained: 6.08 grams (57.9% for both crops). MS (GC-MS) m/z 364.5 (M$^+$). $^1$H NMR (CDCl$_3$): δ 1.52–2.23 (m, 14H, adamantyl-H), 2.80 (s, 1H, 2-H-adamantyl), 7.30–7.40 (m, 12H, phenyl-H), 6.05 (m, 1H, fulvene-H), 6.29, 6.59 (d, $^3J_{HH}$=3.4, 3.7 Hz, 2H, fulvene-H). $^{13}$C NMR (CDCl$_3$): δ 28.14, 28.14, 31.21, 31.21, 32.72, 32.72, 38.06, 38.92, 38.92 (adamantyl-C), 45.20 (2-C-adamantyl), 118.16, 125.01, 133.10 (fulvene-CH$_1$), 127.68, 127.68, 127.77, 127.77, 128.31, 128.31, 132.02, 132.02, 132.08, 132.08 (phenyl-CH$_1$), 141.70, 141.70 (ipso-C), 144.39, 148.69, 152.27 (fulvene-CH$_0$). Elemental analysis calculated for $C_{28}H_{28}$: C, 92.26; H, 7.74. Found: C, 83.42; H, 6.59.

Ph$_2$C(3-(2-adamantyl)C$_5$H$_3$)(C$_{13}$H$_8$)H$_2$. In the glove box, a 250 mL round bottom flask was charged with 3-(2-adamantyl)-6,6-diphenylfulvene (20.00 g, 54.87 mmol) and fluorenyllithium diethyl ether adduct (13.51 g, 54.86 mmol). This was equipped with a 180° needle valve and 150 mL of diethyl ether were condensed into the reaction vessel. After stirring at room temperature for 2 days and at reflux for 7 days, 60 mL H$_2$O were slowly added. After 3 hours, the solid that formed was collected by filtration. The air dried product was combined with 100 mL diethyl ether and stirred for 1 hour before collection by suction filtration, rinsing with 25 mL diethyl ether, and in vacuo drying: 14.30 (49.1%). MS (GC-MS) m/z 530.6 (M$^+$). Elemental analysis calculated for $C_{41}H_{38}$: C, 92.78; H, 7.22. Found: C, 85.14, 84.89; H, 6.04, 6.08.

Ph$_2$C(3-(2-adamantyl)C$_5$H$_3$)(C$_{13}$H$_8$)Li$_2$. A large swivel frit was charged with Ph$_2$C(3-(2-adamantyl)C$_5$H$_3$)(C$_{13}$H$_8$)H$_2$ (14.00 g, 26.38 mmol) and evacuated before 150 mL of diethyl ether were condensed in. 35.0 mL of n-butyllithium in hexanes (1.6 M, 56.0 mmol) were syringed in at room temperature over 5 minutes. The reaction was stirred at room temperature for 22 hours and at 40° C. for 5 hours. The orange precipitate was collected and dried in vacuo: 11.44 g (79.9%).

Ph$_2$C(3-(2-adamantyl)C$_5$H$_3$)(C$_{13}$H$_8$)ZrCl$_2$ (4). In the glove box, 4.657 grams of Ph$_2$C(3-(2-adamantyl)C$_5$H$_3$)

($C_{13}H_8$)$Li_2$ (8.582 mmol) were combined with $ZrCl_4$ (2.000 g, 8.583 mmol) in a 100 mL round bottom flask. This was equipped with a 180° needle valve and 60 mL petroleum ether were condensed in by vacuum transfer at −78° C. The vessel was allowed to warm slowly, and after 46 hours of stirring, solvent was removed. The solid was extracted for two days in a cellulose extraction thimble with 150 mL methylene chloride. The obtained solution was filtered through a frit and condensed to 15 mL. After sitting for 1 hour, the formed precipitate was collected on the frit and dried in vacuo: 2.443 g of product 3 were obtained (41.2%). MS (LC-MS) m/z 690.7 ($M^+$). $^1$H NMR ($C_6D_6$): δ 1.46–2.10 (m, 14H, adamantyl-H), 3.36 (s, 1H, 2-H-adamantyl), 5.73, 5.74 (s, 2H, Cp-H), 6.28 (t, $^3J_{HH}$=2.9 Hz, 1H, Cp-H), 6.93, 6.97, 7.02, 7.04, 7.12, 7.14 (t, 3$J_{HH}$=7.3, 7.3, 7.4, 7.4, 7.3, 6.6 Hz, 6H, phenyl-H, 7.59, 7.60, 7.82, 7.95 (d, $^3J_{HH}$=8.1, 8.1, 8.1, 8.4 Hz, 4H, phenyl-H), 6.49, 6.55, 7.90, 7.90 (d, $^3J_{HH}$=8.8, 8.8, 8.4, 8.4 Hz, 4H, Flu-H), 6.71, 6.77, 7.28, 7.33 (t, $^3J_{HH}$=7.0, 7.0, 7.4, 7.4 Hz, 4H, Flu-H). $^{13}$C NMR ($CD_2Cl_2$): δ 27.90, 28.03, 32.30, 32.48, 32.51, 32.72, 37.88, 38.48, 38.64 (adamantyl-C), 43.88 (2-C-adamantyl), 104.23, 104.57, 116.06 (Cp-$CH_1$), 121.30, 121.43, 122.98, 123.28 (Flu-$CH_0$), 123.82, 124.02, 124.53, 124.68, 124.14, 125.28, 126.65, 126.65, 127.20, 127.26, 128.06, 128.06, 129.04, 129.04, 129.13, 129.13, 129.26, 129.39 (phenyl- and Flu-$CH_1$), 139.39 (9-Flu-C), 145.01, 145.11 (ipso-C), other CHO not determined. Elemental analysis calculated for $C_{41}H_{36}Zr_1Cl_2$: C, 71.28; H, 5.25. Found: C, 63.48, 63.71; H, 4.46, 4.57.

Example 6

Preparation of 5.

$Ph_2C$(3-(2-adamantyl)$C_5H_3$)($C_{13}H_8$)$HfCl_2$ (5). In the glove box, 3.388 grams of $Ph_2C$(3-(2-adamantyl)$C_5H_3$)($C_{13}H_8$)$Li_2$ (6.244 mmol, prepared as given in the alternate preparation of 3) were combined with $HfCl_4$ (2.000 g, 6.244 mmol) in a 100 mL round bottom flask. This was equipped with a 180° needle valve and 60 mL petroleum ether were condensed in by vacuum transfer at −78° C. The vessel was allowed to warm slowly, and after 30 hours of stirring, solvent was removed. The solid was extracted overnight in a cellulose extraction thimble with 150 mL methylene chloride. The obtained solution was filtered through a frit and condensed to 30 mL. After sitting for 1 hour, the formed precipitate was collected on the frit and dried in vacuo: 1.547 g of product 5 were obtained (31.8%). A second crop was obtained from toluene: 1.237 g (57.3% for both crops). MS (LC-MS) m/z 778.8 ($M^+$). $^1$H NMR ($C_6D_6$): δ 1.45–2.09 (m, 14H, adamantyl-H), 3.41 (s, 1H, 2-H-adamantyl), 5.68, 5.69 (s, 2H, Cp-H), 6.21 (t, $^3J_{HH}$=3.0 Hz, 1H, Cp-H), 6.93, 6.98, 7.02, 7.04, 7.12, 7.14 (t, $^3J_{HH}$=7.3, 7.3, 7.7, 7.7, 8.0, 8.0 Hz, 6H, phenyl-H), 7.60, 7.60, 7.83, 7.96 (d, $^3J_{HH}$=7.4, 7.4, 8.1, 7.7 Hz, 4H, phenyl-H), 6.54, 6.60, 7.89, 7.89 (d, $^3J_{HH}$=8.8, 9.2, 8.4, 8.4 Hz, 4H, Flu-H), 6.71, 6.77, 7.26, 7.31 (t, $^3J_{HH}$=7.7, 7.7, 7.3, 7.0 Hz, 4H, Flu-H). $^{13}$C NMR ($CD_2Cl_2$): δ 27.91, 28.01, 32.42, 32.47, 32.59, 32.72, 37.93, 38.53, 38.67 (adamantyl-C), 43.83 (2-C-adamantyl), 101.61, 101.92, 115.20 (Cp-$CH_1$), 120.19, 120.27, 121.51, 121.87 (Flu-$CH_0$), 123.62, 123.83, 124.45, 124.57, 124.79, 124.92, 126.68, 126.68, 127.18, 127.24, 127.84, 127.85, 128.99, 128.99, 129.12, 129.12, 129.29, 129.41 (phenyl- and Flu-$CH_1$), 137.91 (9-Flu-C), 145.28, 145.38 (ipso-C), other CHo not determined. Elemental analysis calculated for $C_{41}H_{36}Hf_1Cl_2$: C, 63.29; H, 4.66. Found: C, 66.36, 66.16; H, 4.66, 4.69.

Example 7

Preparation of 6 norbornylfulvene. Norcamphor (10.00 g, 90.8 mmol) and sodium methoxide (12.0 g, 222 mmol) and 100 mL methanol were added to a 250 mL flask. The solids were dissolved before addition of cyclopentadiene (12.0 g, 182 mmol). After stirring for 68 hours, 200 mL water and 100 mL diethyl ether were added to the deep red solution. The organic layer was isolated and the aqueous layer was extracted with diethyl ether (3×50 mL). The combined organic layers were dried over $MgSO_4$, filtered and rotavapped to yield the crude product in quantitative yield.

norbornylcyclopentadiene. A solution of norbornylfulvene (14.37 g, 90.8 mmol) dissolved in 100 mL tetrahydrofuran was cooled to 0° C. before $LiAlH_4$ (5.00 g, 132 mmol) was added over 2 minutes. After stirring at room temperature for 17 hours, the reaction was cooled to 0° C. and 100 mL water were added dropwise over 1 hour. Then, 200 mL water/50 mL concentrated aqueous HCl and 100 mL diethyl ether were added. The organic layer was isolated and the aqueous layer was extracted with diethyl ether (3×50 mL). The organic layers were dried over $MgSO_4$, filtered, and rotavapped to provide the crude product as a light yellow oil in quantitative yield.

3-(2-norbornyl)-6,6-dimethylfulvene. Sodium methoxide (4.00 g, 74.0 mmol) was added to a solution of norbornylcyclopentadiene (8.00 g, 49.9 mmol) in 50 mL methanol. Acetone (15.8 g, 270 mmol) was added and the reaction stirred for 48 hours when 200 mL water and 100 mL diethyl ether were added. The organic layer was isolated and the aqueous layer was extracted with diethyl ether (4×50 mL). The organic layers were dried over $MgSO_4$, filtered, and rotavapped to provide the crude product as a yellow oil, which was purified by in vacuo drying and passing through a short column of alumina: 8.18 g (81.8%). MS (GC-MS) m/z 200.3 ($M^+$).

$Me_2C$(3-(2-norbornyl)$C_5H_3$)($C_{13}H_8$)$H_2$. A 250 mL flask was charged with fluorene (3.32 g, 20.0 mmol), evacuated, and backfilled with argon before 60 mL tetrahydrofuran and 13.0 mL n-butyllithium in hexanes (1.6 M, 20.8 mmol) were syringed in. The orange solution was stirred for 30 minutes before 3-(2-norbornyl)-6,6-dimethylfulvene (4.00 g, 20.0 mmol) were syringed in. Following an additional 20 hours, the stirred reaction was quenched by addition of 60 mL aqueous $NH_4Cl$. The organic layer was isolated and the aqueous layer extracted with diethyl ether (2×25 mL). The combined organic layers were dried over $MgSO_4$, filtered, rotavapped, and dried in vacuo to give 7.32 grams of product as a light yellow oil in quantitative yield.

$Me_2C$(3-(2-norbornyl)$C_5H_3$)($C_{13}H_8$)$Li_2$. A swivel frit was charged with $Me_2C$(3-(2-norbornyl)$C_5H_3$)($C_{13}H_8$)$H_2$ (7.32 g, 20.0 mmol) and evacuated before 50 mL of diethyl ether were condensed in. To the solution was added 26.0 mL of n-butyllithium in hexanes (1.6 M, 41.6 mmol) at 0° C. over 1 minute. The reaction was stirred at room temperature for 18 hours before the solvent was removed and 50 mL petroleum ether were added by vacuum transfer. After stirring, the solvent was decanted from the red oil and the oil dried in vacuo to provide the product in quantitative yield as a red-yellow powder.

$Me_2C$(3-(2-norbornyl)$C_5H_3$)($C_{13}H_8$)$ZrCl_2$ (6). In the glove box, 2.44 grams of $Me_2C$(3-(2-norbornyl)$C_5H_3$)($C_{13}H_8$)$Li_2$ (6.44 mmol) were combined with $ZrCl_4$ (1.50 g, 6.44 mmol) in a 100 mL round bottom flask. This was equipped with a 180° needle valve and 40 petroleum ether were condensed in by vacuum transfer at −78° C. The vessel was allowed to warm slowly, and after 24 hours of stirring, solvent was removed. Then 30 mL of dichloromethane were added and removed, followed by addition and removal of 30 mL diethyl ether. The solid was extracted overnight in a cellulose extraction thimble with 150 mL of diethyl ether. The filtrate volume was reduced to 30 mL and the precipitated product was collected on a swivel frit and dried in vacuo: 1.26 grams of 5 (37.2%) in a 54:46 diastereomeric ratio. MS (LC-MS) m/z 526.6 (M$^+$). Major diastereomer (54%): $^1$H NMR (C$_6$D$_6$): δ 1.01–1.35 (m, 8H, norbornyl-H), 1.89–2.07 (m, 2H, norbornyl-H), 1.82, 1.83 (s, 6H, C(CH$_3$)$_2$), 3.20 (m, 1H, 2-H-norbornyl), 5.42, 5.45, 6.09 (t, $^3$J$_{HH}$=3.3, 3.3, 2.9 Hz, 3H, Cp-H), 7.00, 7.03, 7.35, 7.35 (t, $^3$J$_{HH}$=7.7, 7.7, 7.3, 7.3 Hz, 4H, Flu-H), 7.45, 7.47, 7.84, 7.86 (d, $^3$J$_{HH}$=8.1, 8.8, 8.4, 8.4 Hz, 4H, Flu-H). $^{13}$C NMR (CD$_2$Cl$_2$): δ 23.52, 29.71, 34.05, 37.25, 40.13, 41.00, 43.61, (norbornyl-C), 28.58, 28.66 (CH3), 40.51 (CH$_3$CCH$_3$), 65.70, 79.12, 114.31, 122.59, 122.88, 123.15, 140.29 (Cp- and Flu-CH$_0$), 102.73, 103.79, 116.17 (Cp-CH$_1$), 123.49, 123.58, 124.64, 124.74, 124.80, 124.84, 128.76, 128.84 (Flu-CH$_1$). Minor diastereomer (46%): $^1$H NMR (C$_6$D$_6$): δ 1.01–1.35 (m, 8H, norbornyl-H), 1.89–2.07 (m, 2H, norbornyl-H), 1.79, 1.83 (s, 6H, C(CH$_3$)$_2$), 3.13 (m, 1H, 2-H-norbornyl), 5.23, 5.54, 6.04 (t, $^3$J$_{HH}$=3.0, 2.9, 2.9 Hz, 3H, Cp-H), 6.98, 7.03, 7.30, 7.30 (t, J$_{HH}$=7.7, 7.7, 7.7, 7.7 Hz, 4H, Flu-H), 7.43, 7.45, 7.83, 7.84 (d, $^3$J$_{HH}$=8.4,8.1,8.4, 8.4 Hz,4H, FLu-H). $^{13}$C NMR (CD$_2$Cl$_2$): δ 23.68, 29.80, 34.17, 36.97, 39.39, 41.53, 43.29, (norbornyl-C), 28.58, 28.58 (CH3), 40.55 (CH$_3$CCH$_3$), 65.65, 79.02, 113.27, 122.55, 122.88, 123.40, 138.57 (Cp- and Flu-CH$_0$), 102.31, 103.69, 117.44 (Cp-CHi), 123.37,123.71, 124.64, 124.74, 124.80,124.84, 128.84, 128.92 (Flu-CH$_1$). Elemental analysis calculated for C$_{28}$H$_{28}$Zr$_1$Cl$_2$: C, 63.86; H, 5.36. Found: C, 61.78, 61.58; H, 5.03, 5.23.

Example 8

Preparation of 7.

3-(2-norbornyl)-6,6-diphenylfulvene. A 500 mL round bottom flask was charged with a solution of norbornylcyclopentadiene (7.39 g, 46.1 mmol) and benzophenone (8.41 g, 46.2 mmol) in 100 mL absolute ethanol. NaOMe (5.50 g, 102 mmol) was added and the orange solution was stirred for 61 days before 100 mL H$_2$O and 100 mL diethyl ether were added. The organic layer was isolated and the aqueous layer was extracted with diethyl ether (2×50 mL). The combined organic layers were dried over MgSO$_4$, filtered, and rotavapped to provide 14.88 grams of red oily material. This was subjected to Kugelrohr distillation under high vacuum at 80–100° C., leaving behind 9.30 grams of red oil. This was Kugelrohred at 100–160° C. to afford 7.05 grams of product as a viscous red oil (47.1%).

Ph$_2$C(3-(2-norbornyl)C$_5$H$_3$)(C$_{13}$H$_8$)H$_2$. In the glove box, a 100 mL round bottom flask was charged with 3-(2-norbornyl)-6,6-diphenylfulvene (7.05 g, 21.7 mmol) and fluorenyllithium diethyl ether adduct (5.35 g, 21.7 mmol). This was equipped with a 180° needle valve and 60 mL of diethyl ether were condensed into the reaction vessel. After stirring with intermittent heating by a warm water bath for 11 days, 20 mL of H$_2$O were slowly added. The precipitate that eventually formed was collected by suction filtration and dried in vacuo: 6.136 grams (57.6%). MS (GC-MS) m/z 490.6 (M$^+$). Elemental analysis calculated for C$_{38}$H$_{34}$: C, 93.02; H, 6.98. Found: C, 78.93, 79.39; H, 5.27, 5.25.

Ph$_2$C(3-(2-norbornyl)C$_5$H$_3$)(C$_{13}$H$_8$)Li$_2$. A swivel frit was charged with Ph$_2$C(3-(2-norbornyl)C$_5$H$_3$)(C$_{13}$H$_8$)H$_2$ (6.136 g, 12.50 mmol) and evacuated before 60 mL of diethyl ether were condensed in. To the white slurry was added 17.0 mL of n-butyllithium in hexanes (1.6 M, 27.2 mmol) at room temperature over 3 minutes, giving a homogeneous solution, which began precipitation after 20 minutes. The reaction was stirred at room temperature for 15 hours and the yellow precipitate was collected and dried in vacuo to yield the product in quantitative yield.

Ph$_2$C(3-(2-norbornyl)C$_5$H$_3$)(C$_{13}$H$_8$)ZrCl$_2$ (7). In the glove box, 3.24 grams of Ph$_2$C(3-(2-norbornyl)C$_5$H$_3$)(C$_{13}$H$_8$)Li$_2$ (6.44 mmol) were combined with ZrCl$_4$ (1.50 g, 6.44 mmol) in a 100 mL round bottom flask. This was equipped with a 180° needle valve and 60 petroleum ether were condensed in by vacuum transfer at −78° C. The vessel was allowed to warm slowly, and after 24 hours of stirring, solvent was removed. The solid was extracted overnight in a cellulose extraction thimble with 150 mL methylene chloride. The solvent was removed and the solid redissolved in 75 mL toluene and 25 mL methylene chloride. The obtained solution was filtered through a frit, all solvent was removed, and 40 mL toluene were condensed in. The orange solid was broken up, stirred, collected on the frit and dried in vacuo to afford the product 5 in a 64:36 diastereomeric ratio: 1.81 grams (43.2%). MS (LC-MS) ml/z 650.5 (M$^+$). Major diastereomer (64%): $^1$H NMR (C$_6$D$_6$): δ 0.99–1.40 (m, 8H, norbornyl-H), 1.83–2.09 (m, 2H, norbornyl-H), 3.09 (m, 1H, 2-H-norbornyl), 5.53, 5.71, 6.19 (t, $^3$J$_{HH}$=3.0, 2.9, 2.6 Hz, 3H, Cp-H), 6.91–7.13 (m, 6H, phenyl-H), 7.56, 7.56, 7.75, 7.75 (d, $^3$J$_{HH}$=8.1, 8.1, 7.7, 7.7 Hz, 4H, phenyl-H), 6.49, 6.53, 7.89, 7.89 (d, $^3$J$_{HH}$=8.8, 8.8, 8.1, 8.1 Hz, 4H, Flu-H), 6.78, 6.81, 7.31, 7.33 (t, $^3$J$_{HH}$=7.7, 7.7, 8.4, 8.4 Hz, 4H, Flu-H). $^{13}$C NMR (CD$_2$Cl$_2$): δ 23.91, 29.78, 34.42, 37.34, 40.19, 41.64, 43.41 (norbornyl-C), 58.33 (PhCPh), 78.20, 109.96, 121.26, 121.61, 123.10, 123.30, 138.11, 145.00, 145.00(Cp-, phenyl-, and Flu-CH$_0$), 104.38, 105.22, 115.76 (Cp-CH$_1$), 123.97, 123.97, 124.61, 124.69, 125.30, 125.30, 126.68, 126.73, 127.26, 127.31, 128.03, 128.11, 128.23, 129.05, 129.08, 129.17, 129.29, 129.36 (phenyl- and Flu-CH$_1$). Minor diastereomer: $^1$H NMR (C$_6$D$_6$): δ 0.99–1.40 (m, 8H, norbornyl-H), 1.83–2.09 (m, 2H, norbornyl-H), 3.19 (m, 1H, 2-H-norbornyl), 5.66, 5.80, 6.11 (t, $^3$J H=2.9, 2.9, 2.6 Hz, 3H, Cp-H), 6.91–7.13 (m, 6H, phenyl-H), 7.58, 7.60, 7.79, 7.79 (d, $^3$J$_{HH}$=8.1, 8.1, 8.0, 8.0 Hz, 4H, phenyl-H), 6.45, 6.58, 7.91, 7.91 (d, $^3$J$_{HH}$=8.8, 8.8, 8.1, 8.1 Hz, 4H, Flu-H), 6.76, 6.78, 7.29, 7.33 (t, $^3$J$_{HH}$=7.7, 7.7, 8.4, 8.4 Hz, 4H, Flu-H). $^{13}$C NMR (CD$_2$Cl$_2$): δ 23.88, 29.66, 34.14, 37.02, 39.45, 40.93, 44.04 (norbornyl-C), 58.33 (PhCPh), 78.43, 108.97, 121.37, 121.50, 123.00, 123.30, 139.95, 144.92, 145.20 (Cp-, phenyl-, and Flu-CH$_0$), 103.63, 105.16, 116.84 (Cp-CH$_1$), 123.67, 124.07, 124.61, 124.74, 125.13, 125.39, 126.57, 126.64, 127.26, 127.31, 128.09, 128.11, 128.18, 129.08, 129.17, 129.29, 129.36, 129.45 (phenyl- and Flu-CH$_1$). Elemental analysis calculated for C$_{38}$H$_{32}$Zr$_1$Cl$_2$: C, 70.13; H, 4.96. Found: C, 71.10, 70.50; H, 4.71, 4.64.

Example 9

Preparation of 8.

3,3,5,5-tetramethylcyclohexylfulvene. Hexane washed sodium spheres (2.40 g, 104 mmol) were slowly added to 100 mL absolute ethanol. The sodium had fully reacted before cyclopentadiene (6.0 mL, 72.6 mmol) and 3,3,5,5-tetramethylcyclohexanone (10.0 mL, 57.1 mmol) were added. After 30 hours, the reaction was poured into 200 mL water and 100 mL diethyl ether were added. The organic layer was isolated and the aqueous layer was extracted with diethyl ether (3×50 mL). The combined organic layers were extracted with water (3×50 mL), dried over MgSO$_4$, filtered, and rotavapped to produce the product in quantitative yield as a yellow oil. MS (GC-MS) m/z 202.3 (M$^+$). $^1$H NMR (CDCl$_3$): δ 0.97 (s, 12H, CH$_3$), 1.04 (s, 2H, CH$_2$), 2.39 (s, 4H, CH$_2$), 6.52, 6.52 (m, 4H, fulvene-H).

1-(cyclopentadienyl)-3,3,5,5-tetramethylcyclohexane. A 500 mL flask was charged with LiAlH$_4$ (2.50 g, 65.9 mmol) and 200 mL tetrahydrofuran. An addition funnel containing 3,3,5,5-tetramethylcyclohexylfulvene (11.89 g, 58.8 mmol) dissolved in 50 mL tetrahydrofuran was attached. The vessel was cooled to 0° C. before dropwise addition over 25 minutes. After 17 hours of stirring at room temperature, the vessel was cooled to 0° C. and 20 mL of water were added dropwise. Then, aqueous NH$_4$Cl (100 mL) and water (200 mL) were added before the organic layer was isolated. 15 mL of concentrated aqueous HCl were added to the aqueous layer and it was extracted with diethyl ether (3×50 mL). The combined organic layers were dried over MgSO$_4$, filtered, and rotavapped to provide 11.87 grams of product (98.8%) as a light orange oil. MS (GC-MS) m/z 204.3 (M$^+$). 3-(3, 3,5,5-tetramethylcyclohexyl)-6,6-dimethylfulvene. A 500 mL flask was charged with 1-(cyclopentadienyl)-3,3,5,5-tetramethylcyclohexane (11.87 g, 58.1 mmol), 100 mL methanol, acetone (30 mL, 430 mmol), and pyrrolidine (1.0 mL, 12 mmol). After stirring for 52 hours, 5 mL of acetic acid were added, along with 200 mL water and 100 mL diethyl ether. The organic layer was isolated and the aqueous layer was extracted with diethyl ether (3×50 mL). The combined organic layers were extracted with H$_2$O (3×30 mL) and 10% aqueous NaOH (3×30 mL). The organic layer was dried over MgSO$_4$, filtered, rotavapped, dried in vacuo, and pushed through a short column of alumina to provide the product in quantitative yield as a yellow oil. MS (GC-MS) m/z 244.4 (M$^+$).

Me$_2$C(3-(3,3,5,5-tetramethylcyclohexyl)C$_5$H$_3$)(C$_{13}$H$_8$)H$_2$. A 250 mL flask was charged with fluorene (3.69 g, 22.2 mmol), evacuated, and backfilled with argon before 60 mL tetrahydrofuran and 14.0 mL n-butyllithium in hexanes (1.6 M, 22.4 mmol) were syringed in. The orange solution was stirred for 2 hours before 3-(3,3,5,5-tetramethylcyclohexyl)-6,6-dimethylfulvene (5.42 g, 22.2 mmol) were syringed in. Following an additional 6 hours, the stirred reaction was quenched by addition of 60 mL aqueous NH$_4$Cl. The organic layer was isolated and the aqueous layer extracted with diethyl ether (2×30 mL). The combined organic layers were dried over MgSO$_4$, filtered, and rotavapped to give 8.75 grams of product as a light yellow oil (96.1%).

Me$_2$C(3-(3,3,5,5-tetramethylcyclohexyl)C$_5$H$_3$)(C$_{13}$H$_8$)Li$_2$. A round bottom flask containing 8.75 grams (21.3 mmol) of Me$_2$C(3-(3,3,5,5-tetramethylcyclohexyl)C$_5$H$_3$)(C$_{13}$H$_8$)H$_2$ was attached to a swivel frit and evacuated before 75 mL of diethyl ether were condensed in. At 0° C., 28.0 mL of n-butyllithium in hexanes (1.6 M, 44.8 mmol) were syringed in over 2 minutes. After, stirring for 15 hours at room temperature, solvent was removed and 75 mL of petroleum ether were condensed in. Solvent was decanted from the viscous oil and the remaining material was dried in vacuo: 8.29 g (92.0%) of product as a bright orange powder.

Me$_2$C(3-(3,3,5,5-tetramethylcyclohexyl)C$_5$H$_3$)(C$_{13}$H8) ZrCl2 (8). In the glove box, 1.81 grams of Me$_2$C(3-(3,3,5, 5-tetramethylcyclohexyl)C$_5$H$_3$)(C$_{13}$H$_8$)Li$_2$ (4.29 mmol) were combined with ZrCl$_4$ (1.00 g, 4.29 mmol) in a 100 mL round bottom flask. This was attached to a swivel frit and 50 petroleum ether were condensed in by vacuum transfer at −78° C. The vessel was allowed to warm slowly, and after 15 hours of stirring, solvent was removed. 40 mL of methylene chloride were condensed in; the solution was warmed and stirred before solvent removal. Then, 30 mL of diethyl ether were condensed in and the slurry was warmed and stirred. The obtained orange solid was extracted several times on the frit with refluxing diethyl ether before the filtrate was condensed to 20 mL. The precipitate was collected on the frit and dried in vacuo to afford the product 7: 0.16 grams (6.6%). Second and third crops were obtained: 0.13 g and 0.23 g (21.2% for all three crops). MS (LC-MS) m/z 570.6 (M$^+$). $^1$H NMR (CD$_2$Cl$_2$): δ 0.83, 0.83, 0.90, 0.99 (s, 12H, cyclohexyl(CH$_3$)), 0.88–1.27 (m, 6H, cyclohexyl-H), 2.33, 2.35 (s, 6H, C(CH$_3$)$_2$), 2.69 (t, $^3J_{HH}$=12.4 Hz, 1H, 1-H-cyclohexyl), 5.46, 5.69, 5.99 (t, 3J$_{HH}$=2.6, 3.3, 2.6 Hz, 3H, Cp-H), 7.24, 7.26, 7.51, 7.53 (t, $^3J_{HH}$=7.7, 7.7, 7.7, 7.5 Hz, 4H, Flu-H), 7.82, 7.86, 8.12, 8.12 (d, $^3J_{HH}$=8.8, 9.2, 8.4, 8.4 Hz, 4H, Flu-H). $^{13}$C NMR (CD$_2$Cl$_2$): δ 26.77, 27.23, 28.47, 28.52, 28.62, 28.67 (CH3), 31.44 (1-cyclohexyl-C), 32.05, 39.71, 40.50, 43.45, 49.00, 52.01 (cyclohexyl and MeCMe CHo and CH2), 102.69, 102.74, 115.19 (Cp-CH$_1$), 123.56, 123.58, 123.58, 124.62, 124.73, 124.73, 124.78, 124.80 (benzo-CH$_1$), 141.29 (9-Flu-C), CH$_0$, not determined. Elemental analysis calculated for C$_{31}$H$_{36}$Zr$_1$Cl$_2$: C, 65.24; H, 6.36. Found: C, 60.96, 61.75; H, 5.53, 5.60.

Example 10

Preparation of 9.

3,6,6-trimethylfulvene. A 1 liter flask was charged with 400 mL methanol, methylcyclopentadiene (120.0 mL, 1.21 mol), acetone (200 mL, 2.72 mol), and pyrrolidine (40.0 mL, 0.464 mol). After stirring the orange solution for 71 hours, 50 mL of acetic acid were added, followed by 1200 mL H$_2$O and 200 mL diethyl ether. The organic layer was isolated and the aqueous layer was extracted with diethyl ether (5×100 mL). The combined organic layers were extracted with H$_2$O (3×30 mL) and 10% aqueous NaOH (3×30 mL). The organic layer was dried over MgSO$_4$, filtered and rotavapped to give 158.8 grams of a red-orange oil that was subjected to Kugelrohr distillation under high vacuum. The first 15 grams of material that distilled at room temperature was discarded and the product was obtained from the second fraction that distilled at 50° C.: 136.58 grams (94.0%).

Me$_2$C(3-methyl-C$_5$H$_3$)(C$_{13}$H$_8$)H$_2$. A 500 mL round bottom flask was charged with fluorene (55.32 g, 332.8 mmol). This was equipped with a 180° needle valve, evacuated, and backfilled with argon before and 240 mL of diethyl ether were added via syringe. 210.0 mL of n-butyllithium in hexanes (1.6 M, 336.0 mmol) were syringed in at room temperature over 20 minutes. After shaking and stirring the obtained yellow slurry for 1 hour, 3,6,6-trimethylfulvene (40.00 g, 332.8 mmol) was syringed in over 25 minutes, providing a clear, red solution. After stirring for 17 hours, the vessel was cooled to 0° C. and 60 mL aqueous NH$_4$Cl solution were added. The slurry was filtered and the aqueous layer removed. The obtained solid was extracted from a cellulose extraction thimble with 500 mL diethyl ether/hexanes for two days. The first crop was obtained by filtration of the cooled filtrate: 28.45 g following in vacuo drying (29.9%). The second and third crops were obtained by filtration of the chilled (−78° C.) filtrate and massed 11.86 and 1.08 grams, respectively (43.4% for all three crops). MS (GC-MS) m/z 286.3 (M$^+$). Elemental analysis calculated for C$_{22}$H$_{22}$: C, 92.26; H, 7.74. Found: C, 90.99, 90.92; H, 7.21, 7.21. 2,6,6-trimethyl-4-(C(methyl)$_2$(9-fluorenyl))-fulvene. 11.86 grams of Me$_2$C(3-methyl-C$_5$H$_3$)(C$_{13}$H$_8$)H$_2$ (41.41 mmol) were combined with 200 mL acetone (2720 mmol) and 15.0 mL pyrrolidine (180 mmol). After stirring for 30 minutes, a homogeneous solution is obtained and stirring is ceased. The product slowly crystallized, and after 30 days the yellow crystals were collected by filtration. These were combined with 100 mL methanol, brought to a boil for 4 hours, and stirred overnight as the vessel cooled. Collection by suction filtration, rinsing with 25 mL methanol, and in vacuo drying afforded 8.15 grams of the desired product (60.3%). MS (GC-MS) m/z 326.5 (M$^+$). $^1$H NMR (CDCl$_3$):

δ 1.02, 1.02 (s, 6H, C(CH$_3$)$_2$Flu), 2.16, 2.25, 2.53 (s, 9H, 2,6,6-CH$_3$-fulvene), 4.13 (s, 1H, 9-H-Flu), 5.96, 6.54 (s, 2H, 3,5-H-fulvene), 7.15, 7.31 (t, $^3J_{HH}$=7.4, 7.4 Hz, 4H, Flu-H), 7.28, 7.70 (s, $^3J_{HH}$=7.3, 7.7 Hz, 4H, Flu-H). $^{13}$C NMR (CDCl$_3$): δ 19.04, 22.46, 24.53, 24.53, 25.18 (CH3), 39.38 (CH$_0$), 55.66 (9-Flu-CH$_1$), 114.78, 130.54 (fulvene-CH$_1$), 119.30, 119.30, 126.07, 126.07, 126.52, 126.52, 126.92, 126.93 (Flu-CH$_1$), 132.75, 133.98, 140.86, 151.75 (fulyene-CH$_0$), 142.04, 142.04, 145.54, 145.54 (Flu-CH$_0$). Elemental analysis calculated for C$_{25}$H$_{26}$: C, 91.97; H, 8.03. Found: C, 90.83, 91.12; H, 7.33, 7.26.

Me$_2$C(3-t-butyl-4-methyl-C$_5$H$_2$)(C$_{13}$H$_8$)H$_2$. A 250 mL round bottom flask was charged with 5.087 grams of 2,6,6-trimethyl-4-(C(methyl)$_2$(9-fluorenyl))-fulvene (15.58 mmol). This was evacuated before 100 mL diethyl ether were condensed in. 75.0 mL of methyllithium in diethyl ether (1.4 M, 105 mmol) were added by syringe, giving an orange homogeneous solution after 1 hour. After one month of stirring, a small amount of orange precipitate was found. The amount slowly increased, and after 47 days total, the orange slurry was cooled to 0° C. and slowly quenched with 60 mL H$_2$O. The organic layer was isolated and the aqueous layer was extracted with diethyl ether (2×25 mL). The combined organic layers were dried over MgSO$_4$, filtered and rotavapped to provide the product in quantitative yield (5.34 g) as a light yellow oil, which slowly began to crystallize.

Me$_2$C(3-t-butyl-4-methyl-C$_5$H$_2$)(C$_{13}$H8)Li$_2$. A round bottom flask containing 5.34 grams (15.6 mmol) of Me$_2$C (3-t-butyl-4-methyl-C$_5$H$_2$)(C$_{13}$H$_8$)H$_2$ was attached to a swivel frit and evacuated before 75 mL of diethyl ether were condensed in. At 0° C., 22.0 mL of n-butyllithium in bexanes (1.6 M, 32.5 mmol) were syringed in over 1 minute. After stirring for 15 hours at room temperature, the orange precipitate was collected and dried in vacuo: 5.37 g (97.3%).

Me$_2$C(3-t-butyl-4-methyl-C$_5$H$_2$)(C$_{13}$H$_8$)ZrCl$_2$ (9). In the glove box, 2.28 grams of Me$_2$C(3-t-butyl-4-methyl-C$_5$H$_2$) (C$_{13}$H$_8$)Li$_2$ (6.44 mmol) were combined with ZrCl$_4$ (1.50 g, 6.44 mmol) in a 100 mL round bottom flask. This was equipped with a 180° needle valve and 50 petroleum ether were condensed in by vacuum transfer at −78° C. The vessel was allowed to warm slowly, and after 23 hours of stirring, solvent was removed. 30 mL of methylene chloride were condensed in; the solution was warmed and stirred before solvent removal; 30 mL of diethyl ether were condensed in; the slurry was warmed and stirred before solvent removal. The obtained solid was extracted overnight in a cellulose extraction thimble with 150 mL methylene chloride. The obtained solution was filtered through a frit, all solvent was removed, and 50 mL diethyl ether were condensed in. The pink solid was broken up, stirred, collected on the frit and dried in vacuo to afford the product 9: 1.60 grams (49.5%). MS (LC-MS) m/z 502.3 (M$^+$). $^1$H NMR (C$_6$D$_6$): δ 1.25 (s, 9H, C(CH$_3$)$_3$) 1.82, 1.85 (s, 6H, C(CH$_3$)$_2$), 2.09 (s, 3H, Cp-CH$_3$), 5.20, 5.50 (d,3J$_{HH}$=3.6, 3.6 Hz, 3H, Cp-H), 6.98, 6.98, 7.31, 7.31 (t,3J$_{HH}$=7.0, 7.0, 7.3, 7.3 Hz, 4H, Flu-h), 7.41, 7.47, 7.82, 7.85 (d, 3J$_{HH}$=8.4, 8.4, 8.0, 8.4 Hz, 4H, Flu-H). $^{13}$C NMR (CD$_2$Cl$_2$): δ 16.08, 28.24, 28.75 (CH3) 29.17 (C(CH$_3$)$_3$), 33.52, 39.85 (CH$_0$), 78.40, 110.49, 121.76, 123.65, 123.79, 128.00, 140.84 (Cp and Flu CH$_0$), 102.93, 108.11 (Cp-CH$_1$), 123.42, 123.64, 124.45, 124.55, 124.68, 124.96, 128.33, 128.80 (Flu-CHi). Elemental analysis calculated for C$_{26}$H$_{28}$Zr$_1$Cl$_2$: C, 62.13; H, 5.61. Found: C, 60.88, 60.89; H, 4.90, 4.94.

Examples 11

Synthesis of 91

6,6-diphenylfulvene. A 1 liter round bottom flask was charged with sodium methoxide (41.00 grams, 0.759 mol), ethanol (500 mL), benzophenone (125.00 grams, 0.686 mol) and cyclopentadiene (100.0 mL, 1.213 mol). This was stirred for 7 days before the orange precipitate was collected by suction filtration and washed with 50 mL ethanol. The collected solid was boiled in 200 mL methanol and allowed to cool. The precipitate was collected by suction filtration and washed with 75 mL methanol. The orange solid was dried under high vacuum for 48 hours, giving 136.18 grams 6,6-diphenylfulvene (86.2%).

2,5-dichloro-2,5-dimethylhexane. A 2 liter round bottom flask was charged with 2,5-dimethyl-2,5-hexanediol (200.0 grams, 1.368 mol). Concentrated aqueous HCl (1.00 liter, 12.2 mol HCl) was poured in. The thick paste was stirred and shaken intermittently for 15 hours. The solid was collected by suction filtration and rinsed with 500 mL water. The solid was dissolved in 1100 mL diethyl ether and the residual water layer removed. The organic layer was dried over MgSO$_4$ and pushed through a column of alumina, followed by rinsing the column with 200 mL diethyl ether. Solvent was removed by rotary distillation to give 235.70 grams of 2,5-dichloro-2,5-dimethylhexane as white crystals (94.1%). octamethyloctahydrodibenzofluorene. An argon-purged 2 liter vessel was charged with fluorene (45.30 grams, 0.2725 mol), 2,5-dichloro-2,5-dimethylhexane (100.00 grams, 0.5461 mol) and nitromethane (800 mL). The solids were dissolved by gentle heating. A solution of AlCl$_3$ (44.65 grams, 0.335 mol) in 60 mL nitromethane was syringed in over 6 minutes. During the addition, much HCl is evolved through an oil bubbler and precipitate is rapidly formed. After stirring for 18 hours, the steel blue reaction is filtered and the solid collected on filter paper. 300 mL water is slowly added to the filtrate and the formed precipitate is collected by suction filtration. The combined precipitates were added slowly to 400 mL water. 200 mL hexanes were added to this and the slurry stirred over night to quench the aluminum chloride. The water layer was removed and the solvent removed from the remaining slurry by rotary evaporation. The solid was extracted over a period of 3 days with 300 mL diethyl ether from a cellulose extraction thimble. Diethyl ether was removed by rotary evaporation and the remaining solid boiled in 100 mL hexanes, cooled, filtered and washed with 50 mL hexanes. In vacuo drying afforded 87.75 grams of octamethyloctahydrodibenzofluorene as a white powder (83.3%).

(methyl)$_2$C(9-octamethyloctahydrodibenzofluorenyl) (cyclopentadienyl)H$_2$. Octamethyloctahydrodibenzofluorene (9.625 g, 24.89 mmol) was massed into a 250 mL round bottom schlenk flask. This was evacuated, backfilled with argon, and charged with 100 mL tetrahydrofuran via syringe. A solution of n-butyllithium in hexanes (16.0 mL, 1.6 M, 25.6 mmol) was syringed in over 10 minutes, giving initially a red solution, which later formed some red precipitate. After 100 minutes, 6,6-dimethylfulvene (3.0 mL, 2.64 g, 24.9 mmol) was syringed in, yielding a homogenous solution. After 22 hours, 60 mL of aqueous NH$_4$Cl were slowly syringed in and the organic layer was isolated. The aqueous layer was extracted with diethyl ether (2×25 mL) and the combined organic layers were dried over MgSO$_4$, filtered, and rotavapped to give the product as a yellow crystalline solid, 12.27 g in theoretical yield.

(methyl)$_2$C(9-octamethyloctahydrodibenzofluorenyl) (cyclopentadienyl)Li$_2$. A 250 mL round bottom flask was charged with (methyl)$_2$C(9- octamethyloctahydrodibenzofluorenyl)(cyclopentadienyl) H$_2$ (12.27 grams, 24.89 mmol) and attached to a swivel frit before 75 mL of diethyl ether were condensed in. A solution of n-butyllithium in hexanes (32.0 mL, 1.6 M, 51.2 mmol) was syringed in over 3 minutes at 0° C. After stirring for 17 hours at room temperature, solvent was removed and 75 mL benzene were condensed in. The solution was frozen and lyophilized to give 11.80 grams of the dilithio salt as an orange powder (93.9%).

(methyl)$_2$C(9-octamethyloctahydrodibenzofluoreny!) (cyclopentadienyl)ZrCl2 (91). In the glove box, a swivel frit apparatus was charged with (methyl)$_2$C(9-octamethyloctahydrodibenzofluorenyl)(cyclopentadienyl) Li$_2$ (3.246 g, 6.436 mmol) and zirconium tetrachloride (1.500 g, 6.437 mmol). 50 mL of petroleum ether were condensed in and the reaction stirred at room temperature for 51 hours before solvent removal. 20 mL dichloromethane were condensed in, stirred, and removed. Then, 30 mL diethyl ether were condensed in, stirred, and removed. In the glove box, the solid was transferred to a cellulose extraction thimble and this was extracted overnight with 100 mL diethyl ether. The obtained slurry was transferred back to the swivel frit and the volume reduced to 30 mL. The orange precipitate (91) was collected on the frit and dried in vacuo: 1.649 g (39.2%).

Example 12

Synthesis of 92

(phenyl)$_2$C(9-octamethyloctahydrodibenzofluorenyl) (cyclopentadienyl)H$_2$. A 300 mL round bottom flask was charged with OctH (12.00 grams, 0.03104 mol) and equipped with a 180° needle valve. This was evacuated and backfilled with argon before 120 mL diethyl ether were added via syringe. This was cooled to 0° C. and 21.0 mL of n-butyllithium in hexanes (1.6 M, 0.0336 mol) were syringed in over 3 minutes. The cold bath was removed and the yellow slurry was stirred for 21 hours, when solvent was removed by vacuum transfer. In the dry box, 6,6-diphenylfulvene (7.148 grams, 0.03104 mol) was added. 150 mL of diethyl ether were added by vacuum transfer at −78° C. The cold bath was subsequently removed and the reaction stirred for 5 days, producing much tan precipitate. 60 mL of aqueous NH$_4$Cl were syringed in slowly at 0° C. 100 mL water were added and the organic layer was isolated. The water layer was extracted with diethyl ether (4×100 mL). The combined organic layers were dried over MgSO$_4$ and filtered. Rotary evaporation of the solvent gave crude product in quantitative yield (19.15 grams). Large, colorless crystals are obtained by recrystallization from boiling ethanol.

(phenyl)$_2$C(9-octamethyloctahydrodibenzofluorenyl) (cyclopentadienyl) ZrCl$_2$ (92). A 250 mL round bottom flask was charged with (phenyl)$_2$C(9-octamethyloctahydrodibenzofluorenyl)(cyclopentadienyl) H$_2$ (10.00 grams, 0.01621 mol), equipped with a 180° needle valve and evacuated. In the dry box, LiCH$_2$Si(CH$_3$)$_3$ (3.053 grams, 0.03242 mol) was added. 75 mL of diethyl ether and then 25 mL of tetrahydrofuran were condensed in at −78°. The cold bath was subsequently removed. After 41 hours, solvent was removed from the stirred, red solution. In the dry box, ZrCl$_4$ (3.78 grams, 0.0162 mol) were added. 75 mL of petroleum ether were condensed in at −78° C. and the cold bath removed. After stirring for 47 hours, solvent was removed from the orange slurry. Then, 50 mL CH$_2$Cl$_2$ were put on/off to quench any unreacted organolithium compounds. Then, 50 mL diethyl ether were put on/off, affording an orange powder which was extracted from a cellulose extraction thimble with 200 mL diethyl ether for 2 days. The volume of the filtrate was condensed to 100 mL and the orange precipitate collected on a frit and dried in vacuo: 5.028 grams of product (2) is obtained in the first crop. Further extraction of the thimble yields another 0.491 grams of product (43.8% total).

EXAMPLES 13–16

Examples of Metallocene Synthesis for Isotactic Polymerization

Example 13

Synthesis of 71 adamantylfulvene. 2-adamantanone (40.22 µg, 267.7 mmol), methanol (200 mL), cyclopentadiene (51.0 mL, 618.9 mmol), and pyrrolidine (20.0 mL, 239.6 mmol) were added to a 1 liter round bottom flask. After stirring for 70 hours, the yellow precipitate was collected by suction filtration and washed with 50 mL methanol. After in vacuo drying, 45.59 grams adamantylfulvene were obtained (85.9%).

2-methyl-2-adamantylcyclopentadiene. A 500 mL round bottom flask was charged with adamantylfulvene (18.00 g, 90.77 mmol) and equipped with a 180° needle valve. This was evacuated, backfilled with argon and charged with 120 mL diethyl ether via syringe. At 0° C., methyllithium/lithium bromide solution (1.5 M in diethyl ether, 225 mmol) were syringed in over 10 minutes. Then, 10 mL dimethoxyethane were syringed in and the reaction was stirred at room temperature for eight days. The vessel was cooled to 0° C. and 60 mL of aqueous NH$_4$Cl were syringed in slowly. The organic layer was isolated and the aqueous layer was extracted with diethyl ether (3×25 mL). The combined organic layers were dried over MgSO$_4$, filtered, and rotavapped to provide the product as a light yellow oil in quantitative yield (19.45 g).

3-(2-methyl-2-adamantyl)-6,6-dimethylfulvene. A flask containing 19.45 grams (90.74 mmol) of 2-methyl-2-adamantylcyclopentadiene was charged with 30 mL acetone, 100 mL methanol, and 10 mL pyrrolidine (120 mmol). The solution formed a yellow precipitate over 96 hours which was collected by suction filtration and rinsed with 50 mL methanol. The material was dried in vacuo to provide 20.36 grams of product as a yellow powder (88.2%).

fluorenyllithium diethyl ether. A 500 mL round bottom flask was charged with fluorene (47.00 grams, 282.8 mmol) and attached to a large swivel frit. This was evacuated before 200 mL diethyl ether were condensed in and 180.0 mL of n-butyllithium solution (1.6 M in hexanes, 288 mmol) were syringed in over 20 minutes at room temperature. After 18 hours, the yellow precipitate was collected and dried in vacuo to provide 50.64 grams of the product as a yellow powder (72.7%).

(methyl)$_2$C(3-(2-methyl-2-adamantyl)cyclopentadienyl) (fluorenyl)H$_2$. In the glove box, a 250 mL round bottom flask was charged with fluorenyllithium-diethyl ether (7.744 g, 31.45 mmol) and 3-(2-methyl-2-adamantyl)-6,6-dimethylfulvene (8.000 g, 31.45 mmol) and equipped with a 180° needle valve. 75 mL of diethyl ether were condensed in and the reaction was stirred at room temperature for 4 days. 60 mL of aqueous NH$_4$Cl were slowly added and the organic layer was isolated. The aqueous layer was extracted with diethyl ether (2×25 mL) and the combined organic layers were dried over MgSO$_4$, filtered, and rotavapped to provide the product as a light yellow oil in quantitative yield (13.23 g).

(methyl)$_2$C(3-(2-methyl-2-adamantyl)cyclopentadienyl) (fluorenyl)Li$_2$. A swivel frit containing (methyl)$_2$C(3-(2- methyl-2-adamantyl)cyclopentadienyl) (fluorenyl)$H_2$ (13.23 g, 32.45 mmol) was evacuated and charged with 50 mL of diethyl ether. At 0° C., 42.0 mL of n-butyllithium solution (1.6 M in hexanes, 67.2 mmol) were syringed in over 4 minutes. After stirring at room temperature for 23 hours, all solvent was removed and 75 mL of petroleum ether were condensed in. The red solid was broken up, collected on the frit, and dried in vacuo to provide the product in quantitative yield (13.60 g).

(methyl)$_2$C(3-(2-methyl-2-adamantyl)cyclopentadienyl)(fluorenyl)zirconium dichloride (71). A 100 mL round bottom flask was charged with (methyl)$_2$C(3-(2-methyl-2-adamantyl)cyclopentadienyl)(fluorenyl)Li$_2$ (4.640 g, 10.73 mmol) and zirconium tetrachloride (2.500 g, 10.73 mmol) and equipped with a 180° needle valve. 40 mL of petroleum ether were condensed in and the reaction was stirred at room temperature for 70 hours. Solvent was removed and the obtained solid was extracted overnight in a soxhlet extractor (cellulose extraction thimble) with 150 mL methylene chloride. The filtrate was condensed to 40 mL and the precipitate was collected and dried in vacuo. 3.246 (52.1%) of 1 was obtained as an orange powder.

Example 14

Synthesis of 72

2,5-dichloro-2,5-dimethylhexane. A 2 liter round bottom flask was charged with 2,5-dimethyl-2,5-hexanediol (200.0 grams, 1.368 mol). Concentrated aqueous HCl (1.00 liter, 12.2 mol HCl) was poured in. The thick paste was stirred and shaken intermittently for 15 hours. The solid was collected by suction filtration and rinsed with 500 mL water. The solid was dissolved in 1100 mL diethyl ether and the residual water layer removed. The organic layer was dried over MgSO$_4$ and pushed through a column of alumina, followed by rinsing the column with 200 mL diethyl ether. Solvent was removed by rotary distillation to give 235.70 grams of 2,5-dichloro-2,5-dimethylhexane as white crystals (94.1%).

octamethyloctahydrodibenzofluorene. An argon-purged 2 liter vessel was charged with fluorene (45.30 grams, 0.2725 mol), 2,5-dichloro-2,5-dimethylhexane (100.00 grams, 0.5461 mol) and nitromethane (800 mL). The solids were dissolved by gentle heating. A solution of AlCl$_3$ (44.65 grams, 0.335 mol) in 60 mL nitromethane was syringed in over 6 minutes. During the addition, much HCl is evolved through an oil bubbler and precipitate is rapidly formed. After stirring for 18 hours, the steel blue reaction is filtered and the solid collected on filter paper. 300 mL water is slowly added to the filtrate and the formed precipitate is collected by suction filtration. The combined precipitates were added slowly to 400 mL water. 200 mL hexanes were added to this and the slurry stirred over night to quench the aluminum chloride. The water layer was removed and the solvent removed from the remaining slurry by rotary evaporation. The solid was extracted over a period of 3 days with 300 mL diethyl ether from a cellulose extraction thimble. Diethyl ether was removed by rotary evaporation and the remaining solid boiled in 100 mL hexanes, cooled, filtered and washed with 50 mL hexanes. In vacuo drying afforded 87.75 grams of octamethyloctahydrodibenzofluorene as a white powder (83.3%).

(methyl)$_2$C(3-(2-methyl-2-adamantyl)cyclopentadienyl)(octamethyloctahydrodibenzofluorenyl)$H_2$. A 250 mL round bottom flask was charged with octamethyloctahydrodibenzofluorene (6.079 g, 15.72 mmol) and equipped with a 180° needle valve. This was evacuated before 75 mL of diethyl ether were condensed in. 10.5 mL of n-butyllithium solution (1.6 M in hexanes, 16.8 mmol) were syringed into the white slurry at room temperature over 10 minutes. After 20 hours of stirring at room temperature, solvent was removed from the yellow slurry. To this was added 3-(2-methyl-2-adamantyl)-6,6-dimethylfulvene (4.000 g, 15.72 mmol) and 75 mL of diethyl ether were condensed in. This reaction was stirred for 13 days before 60 mL of water were slowly added and the organic layer was isolated. The aqueous layer was extracted with diethyl ether (2×25 mL) and the combined organic layers were dried over MgSO$_4$, filtered, and rotavapped to provide the product as a light yellow oil in quantitative yield (10.08 g).

(methyl)$_2$C(3-(2-methyl-2-adamantyl)cyclopentadienyl)(octamethyloctahydrodibenzofluorenyl)Li$_2$. A swivel frit containing (methyl)$_2$C(3-(2-methyl-2-adamantyl)cyclopentadienyl) (octamethyloctahydrodibenzofluorenyl)$H_2$ (10.08 g, 15.72 mmol) was evacuated and charged with 75 mL of diethyl ether. At room temperature, 21.0 mL of n-butyllithium solution (1.6 M in hexanes, 33.6 mmol) were syringed in over 8 minutes. After stirring at room temperature for 15 hours, all solvent was removed and 50 mL petroleum ether were condensed in. An orange precipitate formed slowly and was collected and dried in vacuo to provide 3.525 grams of the product as an orange powder (34.2%)

(methyl)$_2$C(3-(2-methyl-2-adamantyl)cyclopentadienyl)(octamethyloctahydrodibenzofluorenyl)zirconium dichloride (72). A swivel frit apparatus was charged with (methyl)$_2$C(3-(2-methyl-2-adamantyl)cyclopentadienyl)(octamethyloctahydrodibenzofluorenyl)Li$_2$ (3.525 g, 5.40 mmol) and zirconium tetrachloride (1.258 g, 5.40 mmol). 60 mL petroleum ether were condensed in and the reaction stirred at room temperature for 20 hours. The reaction was filtered and all solvent was removed before the material was lyophilized from 30 mL of benzene. 30 mL of hexamethyldisiloxane were condensed in and the slurry stirred for several hours before the red product 2 was collected on the frit and dried in vacuo: 0.614 grams (14.2%).

Examples 15–16

Synthesis of Catalysts for Syndiotactic Polymerization.

The following examples describe the syntheses of catalysts designed for the polymerization of alpha olefins, and propylene in particular, with a syndiotactic mictrostructure.

Example 15

Synthesis of 51

3-(2-adamantyl)-6,6-dimethylfulvene. Pyrrolidine (10.0 mL, 0.116 mol) was syringed into a solution of 2-adamantanone (25.00 g, 0.1664 mol) and cyclopentadiene (30.0 mL, 0.364 mol) in 250 mL of methanol. The reaction was stirred for 92 hours before the yellow precipitate was collected by suction filtration, rinsed with a small volume of methanol and dried in vacuo. 25.71 grams (77.9%) of adamantyl fulvene were isolated. 6.00 grams (0.0303 mol) of this product were dissolved in 30 mL of tetrahydrofuran and this solution added over 30 minutes to at stirred slurry of LiAlH$_4$ (1.40 g, 0.0369 mol) at 0° C. After 5 hours of stirring at room temperature, the reaction was cooled to 0° C. and quenched by slow addition of 20 mL of saturated NH$_4$Cl solution. Then 300 mL H$_2$O, 25 mL concentrated HCl, and 50 mL diethyl ether were added, the organic layer isolated, and the aqueous layer extracted with addition diethyl ether (3×50 mL). The combined organic layers were dried over MgSO$_4$, filtered, and rotavapped to give the product, (2-adamantyl)cyclopentadiene, in quantitative yield as a light yellow oil. To this material was added 50 mL methanol, 50 mL ethanol, 20 mL tetrahydrofuran, 36 mL acetone (0.49 mol) and 0.5 mL pyrrolidine (0.006 mol).

After stirring for 48 hours, 5 mL of acetic acid were injected, followed by 200 mL H$_2$O and 200 mL diethyl ether. The organic layer was isolated and the aqueous layer extracted with diethyl ether (3×40 mL). The combined organic layers were extracted with H$_2$O (3×25 mL) and with 10% aqueous NaOH (3×25 mL), dried over MgSO$_4$, filtered and rotavapped. The obtained yellow solid was further purified by overnight soxlet extraction by 150 mL methanol. The precipitate in the filtrate was isolated by filtration at 0° C., and in vacuo drying: 4.54 g (62.5%) of 3-(2-adamantyl)-6,6-dimethylfulvene, as a yellow powder.

(methyl)$_2$C(3-(2-adamantyl)cyclopentadienyl)(fluorenyl)ZrCl$_2$ (51). 10.5 mL of an n-butyllithium solution (1.6 M in hexanes, 0.0168 mol) was syringed into a solution of sublimed fluorene (2.77 g, 0.0166 mol) in 60 mL tetrahydrofuran. After stirring for 5 hours, a solution of 3-(2-adamantyl)-6,6-dimethylfulvene (4.00 g, 0.0166 mol) in 40 mL tetrahydrofuran was injected over 2 minutes. After stirring for 20 hours, 60 mL of a saturated NH$_4$Cl solution were added, the organic layer isolated, and the aqueous layer extracted with diethyl ether (2×25 mL). The combined organic layers were dried over MgSO$_4$, filtered and rotavapped to give the product (methyl)$_2$C(3-(2-adamantyl)cyclopentadienyl)(fluorenyl)H$_2$ in quantitative yield as a yellow oil. The dianion was prepared by treating a solution of this oil in 75 mL diethyl ether with 22.0 mL of n-butyllithium solution (1.6 M in hexanes, 0.0352 mol) at 0° C. After stirring for 21 hours, the solvent was removed by vacuum transfer and 50 mL of petroleum ether were condensed in. The dilithio salt, (methyl)$_2$C(3-(2-adamantyl)cyclopentadienyl) (fluorenyl)Li$_2$, was isolated by filtration and in vacuo drying in quantitative yield as an orange powder. 2.00 grams of the dilithio salt (0.00478 mol) and 1.114 g sublimed ZrCl$_4$ (0.00478 mol) were combined in a swivel frit apparatus. 40 mL of petroleum ether were condensed in at −78° C. This was allowed to warm slowly to room temperature before solvent removal after 14 hours if stirring. 40 mL of methylene chloride were condensed in and removed in order to quench unreacted ligand. Then the orange solid was extracted in the swivel frit with 50 mL of refluxing diethyl ether. Two crops were obtained for a total of 1.502 grams (55.5%) of 51 as an orange powder following collection at 0° C. and in vacuo drying.

Example 16

Synthesis of 52 adamantylfulvene. 2-adamantanone (40.22 g, 267.7 mmol), methanol (200 mL), cyclopentadiene (51.0 mL, 618.9 mmol), and pyrrolidine (20.0 mL, 239.6 mmol) were added to a 1 liter round bottom flask. After stirring for 70 hours, the yellow precipitate was collected by suction filtration and washed with 50 mL methanol. After in vacuo drying, 45.59 grams adamantylfulvene were obtained (85.9%).

2-adamantylcyclopentadiene. A 500 mL argon-purged round bottom flask was charged with LiAlH$_4$ (8.20 g, 216 mmol) and 100 mL tetrahydrofuran. Adamantylfulvene (30.00 g, 151.3 mmol) was added via solid addition funnel, followed by another 100 mL tetrahydrofuran over 2 minutes at 0° C. After stirring for 22 hours at room temperature, the reaction was cooled to 0° C. and 100 mL water were added dropwise over 60 minutes. Then, 100 mL concentrated aqueous HCl in 300 mL water and 50 mL diethyl ether were added. The organic later was isolated and the aqueous layer extracted with diethyl ether (3×50 mL). The combined organic layers were dried over MgSO$_4$, filtered, and rotavapped to give 30.30 g of product in quantitative yield.

3-(2-adamantyl)-6,6-diphenylfulvene. A 250 mL round bottom flask was charged with 2-adamantylcyclopentadiene (10.24 g, 51.13 mmol), benzophenone (9.32 g, 51.13 mmol) and 100 mL absolute ethanol. Once the solids had dissolved, sodium methoxide (5.00 g, 92.6 mmol) was added and the reaction was stirred for five days. The orange precipitate was collected by suction filtration and washed with 50 mL ethanol. The air dried product was stirred in 100 methanol overnight and the solid was collected by suction filtration and washed with 50 mL methanol. Drying in vacuo for several hours provided 13.32 grams of desired product (71.5%).

(phenyl)$_2$C(3-(2-adamantyl)cyclopentadienyl)(fluorenyl)H$_2$. In the glove box, a 250 mL round bottom flask was charged with 3-(2-adamantyl)-6,6-diphenylfulvene (6.000 g, 16.46 mmol) and fluorenyllithium diethyl ether adduct (4.054 g, 16.46 mmol). This was equipped with a 180° needle valve and 100 mL of diethyl ether were condensed in to the reaction vessel. After stirring at room temperature for 7 days, 60 mL of aqueous NH$_4$Cl and 50 mL water were slowly added. After 2 hours, the solid that formed was collected by filtration and washed with 40 mL diethyl ether. The crude, wet product was dissolved in 250 mL tetrahydrofuran, dried over MgSO$_4$, filtered, rotavapped, and dried in vacuo to give 2.834 grams of a waxy solid as the product (32.4%).

(phenyl)$_2$C(3-(2-adamantyl)cyclopentadienyl)(fluorenyl)ZrCl$_2$ (52). 2.834 grams of (phenyl)$_2$C(3-(2-adamantyl)cyclopentadienyl)(fluorenyl)H$_2$ (5.340 mmol) was combined with LiCH$_2$(trimethylsilane) (1.006 g, 10.68 mmol) in a 250 mL round bottom flask. 50 mL of tetrahydrofuran were condensed in and this was stirred at room temperature for 17 hours, when the solvent was removed. In the glove box, zirconium tetrachloride (1.245 g, 5.343 mmol) was added. 60 mL of petroleum ether were condensed in and the reaction stirred at room temperature for 52 hours. Solvent was removed and 20 mL of dichloromethane were condensed in, stirred, and removed. Then, 50 mL of diethyl ether were condensed in, stirred, and removed. The solid was extracted overnight in a cellulose extraction thimble with 150 mL methylene chloride. The obtained solution was filtered through a frit. Solvent was removed, 15 mL of diethyl ether were condensed in, and the orange solid was broken up, collected at 0° C., and dried in vacuo to give 0.778 grams of product 52 (21.1%).

II. Polymerization

Propylene Polymerization Procedures. CAUTION: All polymerization procedures should be performed behind a blast shield. All polymerization reactions were prepared in nitrogen filled gloveboxes. Methylaluminoxane (MAO) was purchased as a toluene solution from Albemarle Corporation and used as the dry powder obtained by in vacuo removal of all volatiles. Toluene was dried over sodium and distilled. Propylene from Scott Specialty Gases (>99.5%) was used following drying through a Matheson 6110 drying system equipped with an OXYSORB™ column. Polymerizations were conducted in Lab Crest glass reaction vessels (12 oz. for propylene volumes greater than 60 mL, or 3 oz. for propylene volumes less than 60 mL) and were stirred with a magnetic stir bar. Monomer was condensed into the vessel over several minutes at 0° C. The vessel was then equilibrated at either 0° C. or at 20° C. with an ice or water bath for 10 minutes. A given reaction commenced upon injection of a toluene solution of the metallocene into the vessel with a 2.5 mL Hamilton syringe rated to 200 psi. Temperature maintenance was monitored by an affixed pressure gauge. Polymerization reactions were vented and quenched with a small volume of methanol/concentrated HCl (12: 1) and the polymers were separated from hydrolyzed aluminoxanes by precipitation from methanol. Toluene and methanol were removed from the obtained polymers by in vacuo drying.

Examples 17–25

Isotactic Polymerizations

These examples illustrate the polymerization of propylene under suitable conditions and with suitable catalysts for the production of isotactic polypropylene.

Example 17

A 100 mL Lab Crest glass pressure reactor was charged with MAO (0.100 g, $1.72 \times 10^{-3}$ mol [Al]). Propylene (30 mL) was condensed in at 0° C. A solution of (methyl)$_2$C(3-(2-methyl-2-adamantyl)cyclopentadienyl)(fluorenyl) zirconium dichloride (71), (0.001 g, $1.7 \times 10^{-6}$ mol) in toluene (2.0 mL) was injected and the reaction stirred in a 0° C. ice/water bath for 10 minutes. The reaction was vented and quenched with dilute HCl/methanol. 0.410 grams of solid polypropylene were obtained. The polymer has a melting temperature of 157.6° C.

Example 18

A 100 mL Lab Crest glass pressure reactor was charged with MAO (0.100 g, $1.72 \times 10^{-3}$ mol [Al]). Propylene (30 mL) was condensed in at 0° C. A solution of (methyl)$_2$C(3-(2-methyl-2-adamantyl)cyclopentadienyl)(fluorenyl) zirconium dichloride (71), (0.001 g, $1.7 \times 10^{-6}$ mol) in toluene (2.0 mL) was injected and the reaction stirred in a 20° C. water bath for 10 minutes. The reaction was vented and quenched with dilute HCl/methanol. 0.825 grams of solid polypropylene were obtained. The polymer has a melting temperature of 154.0° C.

Example 19

A 100 mL Lab Crest glass pressure reactor was charged with MAO (0.200 g, $3.44 \times 10^{-3}$ mol [Al]). Propylene (60 mL) was condensed in at 0° C. A solution of (methyl)$_2$C(3-(2-methyl-2-adamantyl)cyclopentadienyl)(fluorenyl) zirconium dichloride (71), (0.002 g, $3.4 \times 10^{-6}$ mol) in toluene (2.0 mL) was injected and the reaction stirred in a 0° C. ice/water bath for 60 minutes. The reaction was vented and quenched with dilute HCl/methanol. 3.879 grams of solid polypropylene were obtained. The polymer has a melting temperature of 159.7° C.

Example 20

A 100 mL Lab Crest glass pressure reactor was charged with MAO (0.200 g, $3.44 \times 10^{-3}$ mol [Al]). Propylene (55 mL) was condensed in at 0° C. A solution of (methyl)$_2$C(3-(2-methyl-2-adamantyl)cyclopentadienyl)(fluorenyl) zirconium dichloride (71), (0.002 g, $3.4 \times 10^{-6}$ mol) in toluene (2.0 mL) was injected and the reaction stirred in a 0° C. ice/water bath for 10 minutes. The reaction was vented and quenched with dilute HCl/methanol. 1.375 grams of solid polypropylene were obtained. The polymer has a melting temperature of 159.1° C.

Example 21

A 100 mL Lab Crest glass pressure reactor was charged with MAO (0.200 g, $3.44 \times 10^{-3}$ mol [Al]). Propylene (55 mL) was condensed in at 0° C. A solution of (methyl)$_2$C(3-(2-methyl-2-adamantyl)cyclopentadienyl)(fluorenyl) zirconium dichloride (71), (0.002 g, $3.4 \times 10^{-6}$ mol) in toluene (2.0 mL) was injected and the reaction stirred in a 20° C. water bath for 10 minutes. The reaction was vented and quenched with dilute HCl/methanol. 2.133 grams of solid polypropylene were obtained. The polymer has a melting temperature of 156.3° C.

Example 22

A 100 mL Lab Crest glass pressure reactor was charged with MAO (0.200 g, $3.44 \times 10^{-3}$ mol [Al]) and 28.0 mL toluene. Propylene (3 mL) was condensed in. A solution of (methyl)$_2$C(3-(2-methyl-2-adamantyl)cyclopentadienyl)(fluorenyl) zirconium dichloride (71), (0.002 g, $3.4 \times 10^{-6}$ mol) in toluene (2.0 mL) was injected and the reaction stirred in a 0° C. ice/water bath for 180 minutes. The reaction was vented and quenched with dilute HCl/methanol. 0.869 grams of solid polypropylene were obtained. The polymer has a melting temperature of 157.6° C.

Example 23

A 100 mL Lab Crest glass pressure reactor was charged with MAO (0.200 g, $3.44 \times 10^{-3}$ mol [Al]) and 28.0 mL toluene. Propylene (3 mL) was condensed in. A solution of (methyl)$_2$C(3-(2-methyl-2-adamantyl)cyclopentadienyl)(fluorenyl) zirconium dichloride (71), (0.002 g, $3.4 \times 10^{-6}$ mol) in toluene (2.0 mL) was injected and the reaction stirred in a 20° C. water bath for 90 minutes. The reaction was vented and quenched with dilute HCl/methanol. 0.503 grams of solid polypropylene were obtained. The polymer has a melting temperature of 147.7° C.

Example 24

A 100 mL Lab Crest glass pressure reactor was charged with MAO (0.145 g, $2.50 \times 10^{-3}$ mol [Al]). Propylene (30 mL) was condensed in at 0° C. A solution of (methyl)$_2$C(3-(2-methyl-2-adamantyl)cyclopentadienyl)(octamethyloctahydrodibenzofluorenyl) zirconium dichloride (72), (0.002 g, $2.5 \times 10^{-6}$ mol) in toluene (2.0 mL) was injected and the reaction stirred in a 0° C. ice/water bath for 20 minutes. The reaction was vented and quenched with dilute HCl/methanol. 0.293 grams of solid polypropylene were obtained. The polymer has a melting temperature of 167.0° C.

Example 25

A 100 mL Lab Crest glass pressure reactor was charged with MAO (0.145 g, $2.50 \times 10^{-3}$ mol [Al]). Propylene (30 mL) was condensed in at 0° C. A solution of (methyl)$_2$C(3-(2-methyl-2-adamantyl)cyclopentadienyl)(octamethyloctahydrodibenzofluorenyl) zirconium dichloride (72), (0.002 g, $2.5 \times 10^{-6}$ mol) in toluene (2.0 mL) was injected and the reaction stirred in a 20° C. water bath for 20 minutes. The reaction was vented and quenched with dilute HCl/methanol. 0.704 grams of solid polypropylene were obtained. The polymer has a melting temperature of 162.7° C.

Examples 26–30

Syndiotactic Polymerizations

Examples of propylene polymerization with the $R_2C(Cp^1)(Oct^1)$zirconium dichloride/methylaluminoxane catalyst system.

Example 26

A 100 mL Lab Crest glass pressure reactor was charged with MAO (0.444 g, $7.65 \times 10^{-3}$ mol [Al]). Propylene (25 mL) was condensed in at 0° C. A solution of (methyl)$_2$C (Cp)(Oct)ZrCl$_2$ (91, 0.010 g, 1.5×10$^{-5}$ mol) in toluene (2.0 mL) was injected and the reaction stirred in a 0° C. ice/water bath for 8 minutes. The reaction was vented and quenched with dilute HCl/methanol. 8.68 grams of solid polypropylene were obtained. The polymer has a melting temperature of 153° C.

Example 27

A 100 mL Lab Crest glass pressure reactor was charged with MAO (0.089 g, 1.53×10$^{-3}$ mol [Al]). Propylene (30 mL) was condensed in at 0° C. A solution of (methyl)$_2$C(Cp)(Oct)ZrCl$_2$ (91, 0.0005 g, 7.7×10$^{-7}$ mol) in toluene (1.0 mL) was injected and the reaction stirred in a 0° C. ice/water bath for 10 minutes. The reaction was vented and quenched with dilute HCl/methanol. 0.264 grams of solid polypropylene were obtained.

Example 28

A 100 mL Lab Crest glass pressure reactor was charged with MAO (0.089 g, 1.53×10$^{-3}$ mol [Al]). Propylene (30 mL) was condensed in at 0° C. A solution of (methyl)$_2$C(Cp)(Oct)ZrCl$_2$ (91, 0.0005 g, 7.7×$_{10}$-7 mol) in toluene (1.0 mL) was injected and the reaction stirred in a 20° C. water bath for 10 minutes. The reaction was vented and quenched with dilute HCl/methanol. 0.261 grams of solid polypropylene were obtained.

Example 29

A 100 mL Lab Crest glass pressure reactor was charged with MAO (0.075 g, 1.3×10$^{-3}$ mol [Al]). Propylene (30 mL) was condensed in at 0° C. A solution of (phenyl)$_2$C(Cp)(Oct)ZrCl$_2$ (92, 0.0005 g, 6×10$^{-7}$ mol) in toluene (1.0 mL) was injected and the reaction stirred in a 0° C. ice/water bath for 10 minutes. The reaction was vented and quenched with dilute HCl/methanol. 0.475 grams of solid polypropylene were obtained. The polymer has a melting temperature of 153° C.

Example 30

A 100 mL Lab Crest glass pressure reactor was charged with MAO (0.075 g, 1.3×10$^{-3}$ mol [Al]). Propylene (30 mL) was condensed in at 0° C. A solution of (phenyl)$_2$C(Cp)(Oct)ZrCl$_2$ (92, 0.0005 g, 6×10$^{-7}$ mol) in toluene (1.0 mL) was injected and the reaction stirred in a 20° C. water bath for 10 minutes. The reaction was vented and quenched with dilute HCl/methanol. 1.160 grams of solid polypropylene were obtained. The polymer has a melting temperature of 152° C.

Examples 31–44
Polymerization of Elastomeric Polyolefins

Examples 31–44 demonstrate the polymerization of polypropylene by a number of catalysts of the invention.

Example 31

A 100 mL Lab Crest pressure reactor was charged with MAO (0.256 g, 4.41×10$^{-3}$ mol [Al]). Propylene (25 mL) was condensed in at 0° C. A solution of (methyl)$_2$C(3-(2-adamantyl)cyclopentadienyl)(fluorenyl)ZrCl$_2$ (111, 0.005 g, 9×10$^{-6}$ mol) in toluene (1.0 mL) was injected and the reaction stirred in a 0° C. ice/water bath for 30 minutes. The reaction was vented and quenched with methanol. 5.97 grams of elastomeric polypropylene were obtained.

Example 32

A 200 mL Lab Crest pressure reactor was charged with MAO (0.205 g, 3.53×10$^{-3}$ mol [Al]). Propylene (100 mL) was condensed in at 0° C. A solution of (methyl)$_2$C(3-(2-adamantyl)cyclopentadienyl)(fluorenyl)ZrCl$_2$ (111, 0.001 g, 1.8×10$^{-6}$ mol) in toluene (2.0 mL) was injected and the reaction stirred in a 0° C. ice/water bath for 120 minutes. The reaction was vented and quenched with methanol. 15.03 grams of elastomeric polypropylene were obtained.

Example 33

A 200 mL Lab Crest pressure reactor was charged with MAO (0.205 g, 3.53×10$^{-3}$ mol [Al]). Propylene (100 mL) was condensed in at 0° C. A solution of (methyl)$_2$C(3-(2-adamantyl)cyclopentadienyl)(fluorenyl)ZrCl$_2$ (111, 0.001 g, 1.8×10$^{-6}$ mol) in toluene (2.0 mL) was injected and the reaction stirred in a 20° C. water bath for 90 minutes. The reaction was vented and quenched with methanol. 20.98 grams of elastomeric polypropylene were obtained.

Example 34

A 100 mL Lab Crest pressure reactor was charged with MAO (0.444 g, 7.65×10$^{-3}$ mol [Al]). Propylene (30 mL) was condensed in at 0° C. A solution of (methyl)$_2$C(3-(2-adamantyl)cyclopentadienyl)HfCl$_2$ (112, 0.005 g, 7.6×10$^{-6}$ mol) in toluene (2.0 mL) was injected and the reaction stirred in a 0° C. ice/water bath for 60 minutes. The reaction was vented and quenched with methanol. 0.151 grams of elastomeric polypropylene were obtained.

Example 35

A 100 mL Lab Crest pressure reactor was charged with MAO (0.444 g, 7.65×10$^{-3}$ mol [Al]). Propylene (30 mL) was condensed in at 0° C. A solution of (methyl)$_2$C(3-(2-adamantyl)cyclopentadienyl)HfCl$_2$ (112, 0.005 g, 7.6×10$^{-6}$ mol) in toluene (2.0 mL) was injected and the reaction stirred in a 20° C. water bath for 60 minutes. The reaction was vented and quenched with methanol. 2.34 grams of elastomeric polypropylene were obtained.

Example 36

A 100 mL Lab Crest pressure reactor was charged with MAO (0.508 g, 8.76×10$^{-3}$ mol [Al]). Propylene (25 mL) was condensed in at 0° C. A solution of (methyl)$_2$C(3-(3,3,5,5-tetramethylcyclohexyl)cyclopentadienyl)(fluorenyl)ZrCl$_2$ (113, 0.010 g, 1.8×10$^{-5}$ mol) in toluene (2.0 mL) was injected and the reaction stirred in a 0° C. ice/water bath for 25 minutes. The reaction was vented and quenched with methanol. 11.11 grams of firm, yet rubbery polypropylene were obtained.

Example 37

A 100 mL Lab Crest pressure reactor was charged with MAO (0.282 g, 4.86×10$^{-3}$ mol [Al]). Propylene (25 mL) was condensed in at 0° C. A solution of (methyl)$_2$C(3-cyclohexylcyclopentadienyl)(fluorenyl)ZrCl2 (114, 0.005 g, 1×10$^{-5}$ mol) in toluene (1.0 mL) was injected and the reaction stirred in a 0° C. ice/water bath for 5 minutes. The reaction was vented and quenched with methanol. 6.23 grams of rubbery polypropylene were obtained.

Example 38

A 100 mL Lab Crest pressure reactor was charged with MAO (0.577 g, 9.95×10$^{-3}$ mol [Al]). Propylene (20 mL) was condensed in at 0° C. A solution of (methyl)$_2$C(3-neopentylcyclopentadienyl)(fluorenyl)ZrCl2 (115, 0.010 g, 2.0×10$^{-5}$ mol) in toluene (2.0 mL) was injected and the reaction stirred in a 0° C. ice/water bath for 5 minutes. The reaction was vented and quenched with methanol. 6.21 grams of rubbery polypropylene were obtained.

Example 39

A 100 mL Lab Crest pressure reactor was charged with MAO (0.100 g, $1.72 \times 10^{-3}$ mol [Al]). Propylene (25 mL) was condensed in at 0° C. A solution of (methyl)$_2$C(3-neopentylcyclopentadienyl)(fluorenyl)ZrCl$_2$ (115, 0.001 g, $2 \times 10^{-6}$ mol) in toluene (1.0 mL) was injected and the reaction stirred in a 0° C. ice/water bath for 10 minutes. The reaction was vented and quenched with methanol. 4.01 grams of rubbery polypropylene were obtained.

Example 40

A 100 mL Lab Crest pressure reactor was charged with MAO (0.508 g, $8.76 \times 10^{-3}$ mol [Al]). Propylene (25 mL) was condensed in at 0° C. A solution of (methyl)$_2$C(3-(4-tert-butylcyclohexyl)cyclopentadienyl)(fluorenyl)ZrCl$_2$ (116, 0.010 g, $1.8 \times 10^{-5}$ mol) in toluene (1.0 mL) was injected and the reaction stirred in a 0° C. ice/water bath for 5 minutes. The reaction was vented and quenched with methanol. 7.57 grams of rubbery polypropylene were obtained.

Example 41

A 100 mL Lab Crest pressure reactor was charged with MAO (0.561 g, $9.67 \times 10^{-3}$ mol [Al]). Propylene (25 mL) was condensed in at 0° C. A solution of (methyl)$_2$C(3-(3,3-dimethyl-2-butyl)cyclopentadienyl)(fluorenyl)ZrCl$_2$ (117, 0.010 g, $2.0 \times 10^{-5}$ mol) in toluene (2.0 mL) was injected and the reaction stirred in a 0° C. ice/water bath for 6 minutes. The reaction was vented and quenched with methanol. 7.86 grams of somewhat rigid, rubbery polypropylene were obtained.

Example 42

A 400 mL Lab Crest pressure reactor was charged with MAO (1.260 g, 21.7 mmol [Al]). Propylene (350 mL) was condensed in at 0° C. A solution of (phenyl)$_2$C(3-(2-adamantyl)cyclopentadienyl)(fluorenyl)ZrCl$_2$ (118, 0.015 g, $2.2 \times 10^{-5}$ mol) in toluene (2.0 mL) was injected and the reaction stirred in a 0° C. ice/water bath for 90 minutes. The reaction was vented and quenched with methanol. 23.22 grams of elastomeric polypropylene were obtained. Properties of this polymer, SM-IV-100, are listed below.

Example 43

A 400 mL Lab Crest pressure reactor was charged with MAO (1.260 g, 21.7 mmol [Al]). Propylene (350 mL) was condensed in at 0° C. A solution of (phenyl)$_2$C(3-(2-adamantyl)cyclopentadienyl)(fluorenyl)ZrCl$_2$ (118, 0.015 g, $2.2 \times 10^{-5}$ mol) in toluene (2.0 mL) was injected and the reaction stirred in a 20° C. water bath for 30 minutes. The reaction was vented and quenched with methanol. 27.76 grams of elastomeric polypropylene were obtained. Properties of this polymer, SM-IV-101, are listed in Table XYZ.

Example 44

TABLE 1

Polymerization data with 1–9/MAO in liquid propylene.

| Entry | Metallocene (mg) | MAO (equiv.) | $T_p$ (° C.) | Tol. (mL) | $C_3H_6$ (mL) | Time (min.) | Yield (g) | Activity gP/gmeth | $T_m^a$ (° C.) | m (%) | mmmm (%) | $M_w$ | $M_w/M_n$ |
|---|---|---|---|---|---|---|---|---|---|---|---|---|---|
| 1 | 1 (1.0) | 1000 | 0 | 2.0 | 30 | 15 | 1.43 | 5710 | n.o. | 50.4 | 21.6 | 80,000 | 1.81 |
| 2 | 1 (1.0) | 1000 | 20 | 2.0 | 30 | 10 | 4.95 | 29700 | n.o. | 49.6 | 18.3 | | |
| 3 | 2 (0.5) | 2000 | 0 | 1.0 | 30 | 30 | 1.50 | 6020 | n.o. | 62.3 | 28.4 | 134,000 | 3.15 |
| 4 | 2 (0.5) | 2000 | 20 | 1.0 | 30 | 10 | 1.08 | 12900 | 88 | 62.7 | 31.4 | 81,900 | 4.38 |
| 5 | 2 (2.0) | 1000 | 0 | 2.0 | 55 | 60 | 9.96 | 5000 | n.o. | 61.0 | 28.0 | | |
| 6 | 3 (5.0) | 1000 | 0 | 2.0 | 30 | 60 | 0.15 | 30 | n.o | 64.4 | 32.0 | | |
| 7 | 3 (5.0) | 1000 | 20 | 2.0 | 30 | 60 | 2.34 | 470 | n.o. | 66.4 | 34.0 | | |
| 8 | 4 (15) | 1000 | 0 | 2.0 | 350 | 90 | 23.22 | 1030 | 115 | 57.8 | 27.2 | 638,000 | 2.33 |
| 9 | 4 (15) | 1000 | 20 | 2.0 | 350 | 30 | 27.76 | 3700 | 125 | 55.7 | 25.3 | 435,000 | 2.14 |
| 10 | 4 (2.0) | 1000 | 0 | 2.0 | 180 | 180 | 11.27 | 1900 | 147 | 57.9 | 25.9 | 1,081,000 | 2.33 |
| 11 | 4 (6.0) | 1000 | 0 | 2.0 | 200 | 70 | 26.02 | 3700 | 146 | 58.7 | 26.6 | 1,006,000 | 2.42 |
| 12 | 4 (2.0) | 1000 | 0 | 2.0 | 200 | 360 | 13.85 | 1200 | 125 | 58.8 | 27.7 | 802,000 | 2.43 |
| 13 | 5 (5.0) | 1000 | 0 | 2.0 | 55 | 60 | 0.19 | 38 | 134 | 58.8 | 26.6 | | |
| 14 | 5 (5.0) | 1000 | 20 | 2.0 | 55 | 60 | 1.92 | 384 | n.o. | 58.8 | 28.1 | | |
| 15 | 5 (15) | 1000 | 20 | 2.0 | 55 | 60 | 8.03 | 540 | 135 | 57.6 | 24.0 | 806,000 | 1.93 |
| 16 | 6 (1.0) | 1000 | 0 | 2.0 | 30 | 15 | 1.31 | 5220 | 122 | 57.6 | 27.5 | 105,000 | 1.93 |
| 17 | 6 (1.0) | 1000 | 20 | 2.0 | 30 | 10 | 3.74 | 22500 | n.o. | 58.4 | 28.0 | | |
| 18 | 7 (2.0) | 1000 | 0 | 2.0 | 55 | 60 | 8.38 | 4190 | 148 | 43.8 | 14.7 | 572,000 | 2.55 |
| 19 | 7 (2.0) | 1000 | 20 | 2.0 | 55 | 30 | 12.50 | 12500 | 147 | 50.6 | 18.5 | 390,000 | 2.32 |
| 20 | 8 (2.0) | 1000 | 0 | 2.0 | 30 | 30 | 1.57 | 1570 | 98 | 75.3 | 49.3 | 77,400 | 2.01 |
| 21 | 8 (2.0) | 1000 | 20 | 2.0 | 30 | 15 | 3.54 | 7070 | 91 | 75.0 | 47.9 | | |
| 22 | 9 (1.0) | 1000 | 0 | 2.0 | 30 | 3 | 1.23 | 24600 | n.o. | 57.5 | 26.9 | 653,000 | 1.87 |
| 23 | 9 (0.5) | 1000 | 20 | 1.0 | 30 | 3 | 1.12 | 44700 | n.o. | 61.0 | 30.0 | 397,000 | 2.31 |
| 24 | 9 (1.0) | 1000 | 20 | 2.0 | 55 | 15 | 10.22 | 41000 | 149 | 63.0 | 31.8 | 535,000 | 2.21 |

$^a$n.o. = melting temperature not observed.

III. Polymer Properties

Polymer Characterization. Polymer melting temperatures were determined by differential scanning calorimetry (Perkin-Elmer DSC 7). Typically four or five scans (from 50 to 200° C. at 10° C./minute) were required to find similar melting temperatures among the last two or three scans. Certain melting temperatures (Entries in Table 2: 8–12, 15, 18, 19 and 24) were determined by BP-Amoco with scan rate of 20° C./minute. Polymer molecular weights were determined by BP-Amoco and by Exxon.

Mechanical properties were determined using standard protocols and the test specimens were compression molded according to ASTM D1708. For mechanical testing, the crosshead separation rate was 50.8 cm./min. Exxon used the following protocol:

Plaques suitable for physical property testing were compression molded on a Carver hydraulic press. 6.5 g of polymer was molded between brass plates (0.05" thick) lined with Teflon coated aluminum foil. A 0.033" thick chase with a square opening 4"×4" was used to control sample thickness. After one minute of preheat at 120, under minimal pressure, the hydraulic load was gradually increased to ~10,000–15,000 lbs. at which it was held for three minutes. Subsequently the sample and molding plates were cooled for three minutes under ~10,000 to 15,000 lbs. load between the water cooled platens of the press. Plaques were allowed to equilibrate at room temperature for a minimum of one week prior to physical property testing. Dogbones for tensile testing were cut from compression molded plaques using a mallet handle die. Specimen dimensions were those specified in ASTM D 1708. Tensile properties were measured on an Instron model 4502 equipped with a 22.48 lb. load cell and pneumatic jaws fitted with serrated grip faces. Five specimens of each sample were tested. Deformation was performed at a constant crosshead speed of 5.0 in./min. with a data sampling rate of 25 points/second. Jaw separation prior to testing was 0.876", from which strains were calculated assuming affine deformation. Initial modulus, stress and strain at yield (where evident), stress at 100%, 200%, 300%, 400%, 500% and 1,000% strain, and stress and strain at break were calculated. A minimum of five specimens from each plaque were tested, the results being reported as the average value. All stresses quoted are "engineering" values, i.e., they are calculated based upon the original cross-sectional area of the specimen, taking no account of reduced cross-section as a function of increasing strain. Strain values in excess of 500% are questionable; most samples pulled out of the grips to some extent at higher strains. Thus, the strain calculated from crosshead separation is larger than the strain experienced in the gauge region of the sample. This phenomenon was particularly apparent in samples that exhibited high degrees of strain hardening. Elastic recovery experiments were performed on the Instron 4502 tensile tester using samples with the same specimen dimensions as those used in tensile experiments. Three specimens of each sample were tested. Prior to testing a pair of fiducial ink marks were placed on the gauge region of the sample 0.5" apart (with an Ultra Fine Point Sharpie marker pen). The sample was extended to a nominal 200% elongation (crosshead displacement 1.752") at a crosshead speed of 20 in./min. Once it reached this extension, the crosshead travel was automatically reversed and the crosshead returned to its original position at 20 in./min. The sample was immediately removed from the grips and the separation of the ink marks was measured with calipers. Recovery from the fiducial marks is calculated according to: Recovery from 200% strain (%)=100 (E−0.5)/(0.5), where E=Fiducial mark separation after 24 hours. Results: All samples drew affinely. No samples exhibited a yield peak. All samples strain whitened to some extent. This was particularly noticeable in the sample from Entry 15, in which the whitening was irreversible.

Example 45

TABLE 2

Thermal and mechanical properties of elastomeric polypropylenes.

| | Entry | | | | |
|---|---|---|---|---|---|
| | 5 | 8 | 9 | 10 | 11 |
| Thermal Properties | | | | | |
| melt flow rate (g/600 s, 230° C.) | | 0.1 | 0.41 | | |
| $T_g$ (° C.) | | −3 | −3 | | |
| $T_m$ (° C.) | n.o. | 115 | 125 | 147 | 146 |
| $H_m$ (J/g) | | 9.3 | 6.8 | 5.4 | 4.5 |
| $T_c$ (° C.) | | 66 | 62 | 88 | 86 |
| $H_c$ (J/g) | | 4.6 | 2.7 | 8.7 | 3.1 |
| Mechanical Properties | | | | | |
| initial modulus (psi) | 1007 ± 44 | 679 | 712 | | |
| stress at 100% strain (psi) | 226 ± 2 | | | | |
| stress at 200% strain (psi) | 249 ± 3 | | | | |
| stress at 300% strain (psi) | 180 ± 2 | | | | |
| stress at 400% strain (psi) | 325 ± 3 | | | | |
| stress at 500% strain (psi) | 379 ± 2 | | | | |
| stress at 1000% strain (psi) | 895 ± 10 | | | | |
| stress at break (psi) | 1233 ± 27 | 1215 | 1230 | | |
| strain at break (%) | 1245 ± 30 | 756 | 813 | | |
| % recovery, trial 1 | 11.3 | | | | |
| % recovery, trial 2 | 7.60 | | | | |
| % recovery, trial 3 | 9.10 | | | | |
| % recovery, average[a] | 9.33 | | | | |
| tensile stress relaxation (%)[b] | | 27 | 28 | | |
| tensile hysteresis:[c] | | | | | |
| cumulative set (%)[d] | | 6.5 | 7.3 | | |
| retained force (%)[e] | | 51 | 49 | | |
| [m] (%) | 61.0 | 57.8 | 55.7 | 57.9 | 58.7 |
| $M_n$ | 43,000[f] | 273,000 | 204,000 | 463,000 | 416,000 |

[a]Recovery from 200% strain (%) = (final length − initial length)/(initial length) where initial length = 0.5000 inch.
[b]50% elongation stress decay, 5 minutes.
[c]3 cycles, 100% elongation, 30 second hold at extension, 60 second hold at recovery.
[d]2 cycles.
[e]2nd cycle, (stress at 50% on recovery)/(stress at 100% on extension before hold).
[f]Estimated based on Entry 3, performed with the same catalyst at the same temperature.

Example 46

TABLE 3

Thermal and mechanical properties of elastomeric polypropylenes.

| | Entry | | | | |
|---|---|---|---|---|---|
| | 12 | 15 | 18 | 19 | 24 |
| Thermal Properties | | | | | |
| melt flow rate (g/600 s, 230° C.) | | | | | |
| $T_g$ (° C.) | | | | | |
| $T_m$ (° C.) | 125 | 135 | 148 | 147 | 149 |
| $H_m$ (J/g) | 0.5 | 0.7 | 6.6 | 6.5 | 2.2 |
| $T_c$ (° C.) | 78 | | 87 | 82 | 79 |
| $H_c$ (J/g) | 1.9 | | 7.1 | 7.8 | 3.6 |
| Mechanical Properties | | | | | |
| initial modulus (psi) | | 509 ± 23 | 483 ± 23 | | 1100 ± 33 |
| stress at 100% strain (psi) | | 222 ± 24 | 155 ± 1 | | 260 ± 4 |
| stress at 200% strain (psi) | | 313 ± 7 | 170 ± 1 | | 305 ± 3 |
| stress at 300% strain (psi) | | 415 ± 9 | 174 ± 1 | | 366 ± 3 |
| stress at 400% strain (psi) | | 530 ± 12 | 181 ± 1 | | 459 ± 6 |
| stress at 500% strain (psi) | | 660 ± 14 | 191 ± 1 | | 586 ± 9 |
| stress at 1000% strain (psi) | | NA | 328 ± 8 | | NA |
| stress at break (psi) | | 1219 ± 70 | 642 ± 43 | | 1763 ± 299 |
| strain at break (%) | | 792 ± 32 | 1447 ± 45 | | 910 ± 75 |
| % recovery, trial 1 | | 0.70 | 3.70 | | 3.60 |
| % recovery, trial 2 | | 2.10 | 5.70 | | 3.40 |
| % recovery, trial 3 | | 1.8 | 5.00 | | 4.9 |
| % recovery, average[a] | | 1.53 | 4.80 | | 3.97 |
| tensile stress relaxation (%)[b] | | | | | |
| tensile hysteresis:[c] | | | | | |
| cumulative set (%)[d] | | | | | |
| retained force (%)[e] | | | | | |
| [m] (%) | 58.8 | 57.6 | 43.8 | 50.6 | 63.0 |
| $M_n$ | 330,000 | 417,000 | 224,000 | 168,000 | 242,000 |

[a]Recovery from 200% strain (%) = (final length − initial length)/(initial length) where initial length = 0.5000 inch.
[b]50% elongation stress decay, 5 minutes.
[c]3 cycles, 100% elongation, 30 second hold at extension, 60 second hold at recovery.
[d]2 cycles.
[e]2nd cycle, (stress at 50% on recovery)/(stress at 100% on extension before hold).
[f]Estimated based on Entry 3, performed with the same catalyst at the same temperature.

Example 47

TABLE 4

Thermal and mechanical properties of elastomeric polypropylenes.

| | SM-IV-100 | SM-IV-101 |
|---|---|---|
| melt flow rate, 230° C. g/10 min | 0.1 | 0.41 |
| mmmm, % | 27 | 27 |
| thermal properties | | |
| $T_g$, ° C. | −3 | −2.9 |
| $T_m$, ° C. | 115 | 125 |
| $H_m$, J/g | 9.3 | 6.8 |
| $T_c$, ° C. | 66 | 62 |
| $H_c$, J/g | 4.6 | 2.7 |
| tensile properties | | |
| modulus, MPa | 4.68 | 4.84 |
| elongation to break, % | 756 | 813 |
| strength at break, MPa | 8.38 | 8.48 |
| tensile stress relaxation, 50% elongation stress decay, %, 5 minutes | 27 | 28 |
| tensile hysteresis, 3 cycles, 100% elongation 30 second hold at extension, 60 second hold at recovery: | | |
| cumulative % set, 2 cycles | 6.5 | 7.3 |
| retained force, %, 2nd cycle (stress at 50% on recovery/stress at 100% on extension before hold) | 51 | 49 |

Example 48

$^{13}$C NMR Determination of Polyolefin Tacticity

This example shows that the elastomeric polypropylenes of the invention are predominantly hemiisotactic isotactic stereocopolymers. Hemiisotactic PP generally is missing the mmrm+rrmr and mrmr pentads. In our case, these pentads make up just a small percentage of the polymer, consistent with the general hemiisotactic regime.

TABLE 5

13C NMR derived pentad analysis. (mmrm and rrmr overlap in the NMR spectra and are grouped for anaylsis).

| | Entry | | | | | | | |
|---|---|---|---|---|---|---|---|---|
| | 1 | 2 | 3 | 4 | 5 | 6 | 7 | 8 |
| mmmm | 21.6 | 18.3 | 28.4 | 31.4 | 28.0 | 32.0 | 34.0 | 27.2 |
| mmmr | 10.9 | 11.6 | 15.5 | 14.7 | 14.3 | 15.3 | 15.3 | 13.2 |
| rmmr | 6.0 | 5.5 | 5.3 | 4.5 | 5.7 | 4.6 | 5.1 | 5.5 |
| mmrr | 21.8 | 22.5 | 24.7 | 23.1 | 24.6 | 23.5 | 21.5 | 22.2 |
| mmrm + rrmr | 1.3 | 1.9 | 0.8 | 0.9 | 1.1 | 1.2 | 1.4 | 1.2 |
| mrmr | 0.6 | 0.8 | 0.4 | 0.4 | 0.5 | 0.4 | 0.9 | 0.6 |
| rrrr | 23.1 | 21.3 | 7.9 | 8.2 | 8.1 | 7.5 | 6.6 | 12.5 |
| rrrm | 10.3 | 11.7 | 7.4 | 8.5 | 8.9 | 6.9 | 7.0 | 9.1 |
| mrrm | 4.4 | 6.5 | 9.5 | 8.4 | 9.0 | 8.7 | 8.0 | 8.5 |

| | Entry | | | | | | | |
|---|---|---|---|---|---|---|---|---|
| | 9 | 10 | 11 | 12 | 13 | 14 | 15 | 16 |
| mmmm | 25.3 | 25.9 | 26.6 | 27.7 | 26.6 | 28.1 | 24.0 | 27.5 |
| mmmr | 13.2 | 13.6 | 13.9 | 13.4 | 13.2 | 13.5 | 14.9 | 12.9 |
| rmmr | 5.0 | 5.8 | 5.5 | 5.2 | 6.3 | 5.0 | 6.1 | 5.1 |
| mmrr | 21.5 | 23.4 | 23.5 | 22.6 | 23.1 | 22.3 | 24.0 | 21.3 |
| mmrm + rrmr | 2.3 | 1.2 | 1.3 | 1.4 | 1.3 | 1.6 | 1.0 | 2.0 |
| mrmr | 0.6 | 0.6 | 0.7 | 0.8 | 0.7 | 0.5 | 0.2 | 1.1 |
| rrrr | 11.6 | 12.2 | 11.4 | 12.3 | 12.7 | 11.1 | 11.8 | 13.6 |
| rrrm | 11.1 | 9.4 | 9.4 | 9.0 | 8.9 | 10.2 | 9.4 | 8.8 |
| mrrm | 9.3 | 7.8 | 7.8 | 7.5 | 7.2 | 7.7 | 8.5 | 7.8 |

| | Entry | | | | | | | |
|---|---|---|---|---|---|---|---|---|
| | 17 | 18 | 19 | 20 | 21 | 22 | 23 | 24 |
| mmmm | 28.0 | 14.7 | 18.5 | 49.3 | 47.9 | 26.9 | 30.0 | 31.8 |
| mmmr | 13.3 | 9.8 | 13.4 | 13.2 | 14.3 | 13.4 | 15.1 | 15.3 |
| rmmr | 4.8 | 6.1 | 6.7 | 3.2 | 2.8 | 4.8 | 3.1 | 3.0 |
| mmrr | 21.7 | 22.7 | 21.6 | 15.5 | 16.8 | 20.4 | 19.2 | 19.3 |
| mmrm + rrmr | 2.2 | 2.9 | 1.6 | 2.6 | 2.0 | 4.2 | 5.2 | 5.4 |
| mrmr | 1.0 | 0.6 | 0.8 | 1.0 | 1.2 | 0.2 | 1.2 | 1.4 |
| rrrr | 12.3 | 21.1 | 20.4 | 3.5 | 4.0 | 11.7 | 8.9 | 8.0 |
| rrrm | 9.4 | 13.4 | 10.6 | 4.3 | 4.1 | 10.8 | 8.7 | 7.8 |
| mrrm | 7.3 | 8.6 | 6.5 | 7.3 | 6.9 | 7.6 | 8.6 | 8.1 |

Example 49
Derivation of Isotactic Block Length Distribution for Isotactic-Hemiisotactic Polypropylene This example describes a statistical model of polymer tacticity. One can calculate the isotactic block length distribution for isotactic-hemiisotactic polypropylene. For a hemiisotactic regime, only sequential rr and mm triads are allowed. Therefore, only isotactic blocks containing an odd number of monomers will be allowed and an isotactic block will be defined by (rr)(mm)(s)(rr), where s is the number of repeating mm triads.[16] The probability of creating an isotactic block of length n will be given by $P_n = (1-\alpha)(\alpha)^{((n-1)/2)}(1-\alpha)$, and the number of blocks with length n in a given polymer chain is $N_n = P_n(P_d)$, where $P_d$ is the degree of polymerization.[17]

For a polymer with a=0.62 and $M_n$=100,000, this analysis predicts that the longest isotactic segment present ($N_n$=1) will contain 25 monomer units and there will be a total of 7 blocks of 21 monomer units or longer. Doubling the molecular weight ($M_n$=200,000) results in a polymer for which the longest isotactic segment is 27 monomer units long, but for which there are 15 blocks of 21 monomer units or longer.

For a polymer with a=0.50, the longest isotactic segments present will contain only 19 or 21 monomer units, for $M_n$=100,000 or $M_n$=200,000, respectively. Such a polymer does not contain isotactic blocks in great enough number or length to form the crystalline regions necessary for elastomeric polypropylene.

Finally, for a polymer with a=0.75, the longest isotactic segments present will contain 35 or 39 monomer units and there will be 33 or 67 blocks of length 21 or greater, for $M_n$=100,000 or $M_n$=200,000, respectively. Clearly these will be present at the expense of the requisite amorphous hemiisotactic segments and a rigid polymer will result.

Example 50

Derivation of the Isotactic Block Length Distribution for Isotactic-Hemiisotactic Polypropylene This example shows the derivation for g=0 of block length in elastomeric polypropylene polymers. For a hemiisotactic regime, every other stereocenter is of the same stereochemistry and the intervening stereocenters are of variable stereochemistry. Therefore, as in the hemiisotactic polymer shown below, a given polymer can be represented by a string of mm and rr triads. This disallows the pentads containing isolated m and r dyads: mmrm, rrmr and mrmr. For a given triad, if the probability of obtaining an mm triad is defined as a, then the probability of obtaining an rr triad is 1−α.

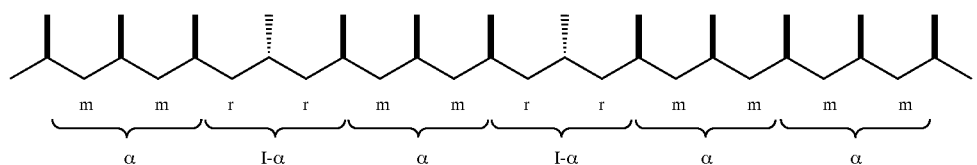

An isotactic block is defined as a collection of m dyads terminated on either end by an r dyad. Since only (mm) and (rr) triads are allowed for hemisotactic polypropylene, an isotactic block must be a collection of (mm) triads terminated on either end by (rr) triads: $(rr)(mm)^{(s)}(rr)$, where s is the number of repeating (mm) triads. The probability of such a sequence will be the product of the individual probabilities.

For example, the isotactic block drawn below containing 13 monomer units is described by $(rr)(mm)^{(6)}(rr)$ and the probability of forming it will be $P_{13} = (1-\alpha)(\alpha)^{(6)}(1-a)$, where s=6. Since the variables s and n are related as s=((n−1)/2), we can generalize for the probability of obtaining an isotactic block containing n repeating monomer units: $P_n = (1-\alpha)(\alpha)^{((n-1)/2)}(1-\alpha)$, for n=odd.

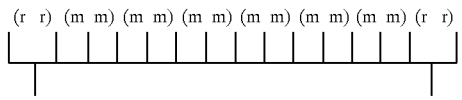

For a given polymer chain, the number of blocks of length n present will be given by $N_n = P_n(P_d)$, where $P_d$ is the degree of polymerization-the number of monomers in that chain given by the number average molecular weight/monomer molecular weight=$M_n/42$ for polypropylene.[1] In the table below, the calculated values for $N_n$ is given as a function of $M_n$ and $\alpha$. For example, a polymer chain of $M_n$=100,000 and a=0.50 is expected to have 4.65 isotactic blocks containing 15 monomer units. This is a statistical average and the actual number of isotactic blocks containing 15 monomer units will be an integral value near 4.65.

Similarly, this polymer chain is expected to have 0.0045 isotactic blocks containing 35 monomer units. While most chains will not contain an isotactic block of this length, statistically, one out of every 222 (=1/0.0045) chains will.

Although the probability of finding an isotactic block of exactly 21 monomer units in a given chain is less than unity, the probability of finding one greater than or equal to 21 monomer units is 1.16, the sum of the $N_n$ values for n=21 through n=99. (An exhaustive calculation would compute up to n=$P_d$.) This suggests that there will be, statistically, at least one isotactic block having 21 or more monomer units in a chain for which $M_n$=100,000 and $\alpha$=0.50.

| | $M_n =$ | | | | | |
|---|---|---|---|---|---|---|
| | 100,000 | 200,000 | 100,000 | 200,000 | 100,000 | 200,000 |
| | | | a = | | | |
| | 0.50 | 0.50 | 0.62 | 0.62 | 0.75 | 0.75 |
| n | $N_n$ | $N_n$ | $N_n$ | $N_n$ | $N_n$ | $N_n$ |
| 1 | 595.2381 | 1190.4762 | 343.8095 | 687.6190 | 148.8095 | 297.6190 |
| 3 | 297.6190 | 595.2381 | 213.1619 | 426.3238 | 111.6071 | 223.2143 |
| 5 | 148.8095 | 297.6190 | 132.1604 | 264.3208 | 83.7054 | 167.4107 |
| 7 | 74.4048 | 148.8095 | 81.9394 | 163.8789 | 62.7790 | 125.5580 |
| 9 | 37.2024 | 74.4048 | 50.8025 | 101.6049 | 47.0843 | 94.1685 |
| 11 | 18.6012 | 37.2024 | 31.4975 | 62.9950 | 35.3132 | 70.6264 |
| 13 | 9.3006 | 18.6012 | 19.5285 | 39.0569 | 26.4849 | 52.9698 |
| 15 | 4.6503 | 9.3006 | 12.1076 | 24.2153 | 19.8637 | 39.7273 |
| 17 | 2.3251 | 4.6503 | 7.5067 | 15.0135 | 14.8978 | 29.7955 |
| 19 | 1.1626 | 2.3251 | 4.6542 | 9.3084 | 11.1733 | 22.3466 |
| 21 | 0.5813 | 1.1626 | 2.8856 | 5.7712 | 8.3800 | 16.7600 |
| 23 | 0.2906 | 0.5813 | 1.7891 | 3.5781 | 6.2850 | 12.5700 |
| 25 | 0.1453 | 0.2906 | 1.1092 | 2.2184 | 4.7137 | 9.4275 |
| 27 | 0.0727 | 0.1453 | 0.6877 | 1.3754 | 3.5353 | 7.0706 |
| 29 | 0.0363 | 0.0727 | 0.4264 | 0.8528 | 2.6515 | 5.3030 |
| 31 | 0.0182 | 0.0363 | 0.2644 | 0.5287 | 1.9886 | 3.9772 |
| 33 | 0.0091 | 0.0182 | 0.1639 | 0.3278 | 1.4915 | 2.9829 |
| 35 | 0.0045 | 0.0091 | 0.1016 | 0.2032 | 1.1186 | 2.2372 |
| 37 | 0.0023 | 0.0045 | 0.0630 | 0.1260 | 0.8389 | 1.6779 |
| 39 | 0.0011 | 0.0023 | 0.0391 | 0.0781 | 0.6292 | 1.2584 |
| 41 | 0.0006 | 0.0011 | 0.0242 | 0.0484 | 0.4719 | 0.9438 |
| 43 | 0.0003 | 0.0006 | 0.0150 | 0.0300 | 0.3539 | 0.7079 |
| 45 | 0.0001 | 0.0003 | 0.0093 | 0.0186 | 0.2654 | 0.5309 |
| 47 | 0.0001 | 0.0001 | 0.0058 | 0.0115 | 0.1991 | 0.3982 |
| 49 | 0.0000 | 0.0001 | 0.0036 | 0.0072 | 0.1493 | 0.2986 |
| 51 | 0.0000 | 0.0000 | 0.0022 | 0.0044 | 0.1120 | 0.2240 |
| 53 | 0.0000 | 0.0000 | 0.0014 | 0.0028 | 0.0840 | 0.1680 |
| 55 | 0.0000 | 0.0000 | 0.0009 | 0.0017 | 0.0630 | 0.1260 |
| 57 | 0.0000 | 0.0000 | 0.0005 | 0.0011 | 0.0472 | 0.0945 |
| 59 | 0.0000 | 0.0000 | 0.0003 | 0.0007 | 0.0354 | 0.0709 |
| 61 | 0.0000 | 0.0000 | 0.0002 | 0.0004 | 0.0266 | 0.0531 |
| 63 | 0.0000 | 0.0000 | 0.0001 | 0.0003 | 0.0199 | 0.0399 |
| 65 | 0.0000 | 0.0000 | 0.0001 | 0.0002 | 0.0149 | 0.0299 |
| 67 | 0.0000 | 0.0000 | 0.0000 | 0.0001 | 0.0112 | 0.0224 |
| 69 | 0.0000 | 0.0000 | 0.0000 | 0.0001 | 0.0084 | 0.0168 |
| 71 | 0.0000 | 0.0000 | 0.0000 | 0.0000 | 0.0063 | 0.0126 |
| 73 | 0.0000 | 0.0000 | 0.0000 | 0.0000 | 0.0047 | 0.0095 |
| 75 | 0.0000 | 0.0000 | 0.0000 | 0.0000 | 0.0035 | 0.0071 |
| 77 | 0.0000 | 0.0000 | 0.0000 | 0.0000 | 0.0027 | 0.0053 |
| 79 | 0.0000 | 0.0000 | 0.0000 | 0.0000 | 0.0020 | 0.0040 |
| 81 | 0.0000 | 0.0000 | 0.0000 | 0.0000 | 0.0015 | 0.0030 |
| 83 | 0.0000 | 0.0000 | 0.0000 | 0.0000 | 0.0011 | 0.0022 |
| 85 | 0.0000 | 0.0000 | 0.0000 | 0.0000 | 0.0008 | 0.0017 |
| 87 | 0.0000 | 0.0000 | 0.0000 | 0.0000 | 0.0006 | 0.0013 |
| 89 | 0.0000 | 0.0000 | 0.0000 | 0.0000 | 0.0005 | 0.0009 |
| 91 | 0.0000 | 0.0000 | 0.0000 | 0.0000 | 0.0004 | 0.0007 |
| 93 | 0.0000 | 0.0000 | 0.0000 | 0.0000 | 0.0003 | 0.0005 |
| 95 | 0.0000 | 0.0000 | 0.0000 | 0.0000 | 0.0002 | 0.0004 |

-continued

|   | $M_n =$ | | | | | |
|---|---|---|---|---|---|---|
|   | 100,000 | 200,000 | 100,000 | 200,000 | 100,000 | 200,000 |
|   | | | $a =$ | | | |
|   | 0.50 | 0.50 | 0.62 | 0.62 | 0.75 | 0.75 |
| n | $N_n$ | $N_n$ | $N_n$ | $N_n$ | $N_n$ | $N_n$ |
| 97 | 0.0000 | 0.0000 | 0.0000 | 0.0000 | 0.0001 | 0.0003 |
| 99 | 0.0000 | 0.0000 | 0.0000 | 0.0000 | 0.0001 | 0.0002 |
| Sum $N_n$ for n = 21 | 1.16 | 2.33 | 7.59 | 15.19 | 33.52 | 67.04 |

$N_n = [(1 - \alpha)(\alpha)^{((n-1)/2)}(1 - a)] \cdot [M_n/42]$

Example 51
Extimated Block Length of Elastomeric Polymers

A "block index range" for our polymers might be considered as follows: For a polymer with m dyad content (alpha) of 0.62, and a molecular weight (Mn) of 100,000 statistics would predict the presence of at least: one isotactic block of length 25, one block of length 23, two blocks of length 21, four blocks of length 19, seven blocks of length 17, and so forth. The total numer of blocks having length 21 or greater (a reasonable cutoff for participation in crystallites) is 7.59, on a statistical basis. The most probable scenario for this polymer is that it contains seven blocks of sufficient length to participate in a crystalline region.

For the methyl substituted catalyst (m dyad near 50%), one would expect only 1 block of length 21 or greater for the same molecular weight (not enough: amorphous). For the 3,3,5,5-tetramethylcyclohexyl substituted catalyst (m dyad near 75%), one would expect 33 blocks of length 21 or greater for the same molecular weight (too many: a single, crystalline phase)

Note that our polymers, based on a hemiisotactic regime, are notpredicted to have isotactic blocks of even length. This is in stark contrast to the Waymouth elastomers for which a smooth continuum of odd and even length blocks are predicted.

Example 52
Catalysts for Syndiotactic Polymerization

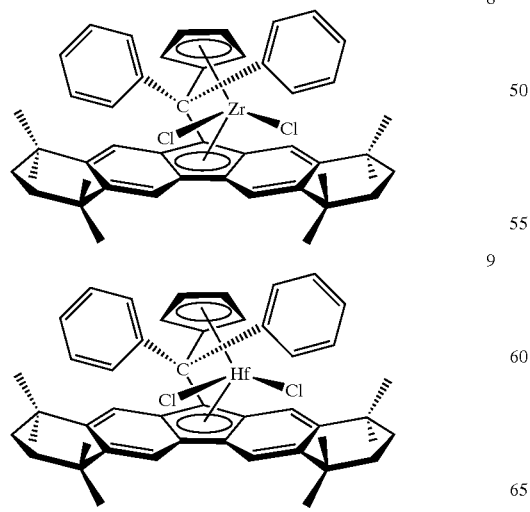

-continued

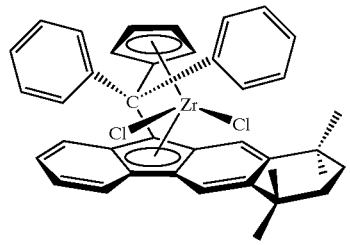

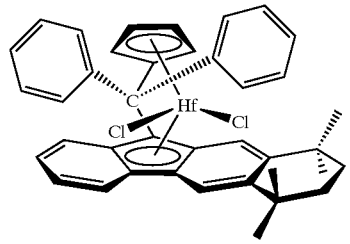

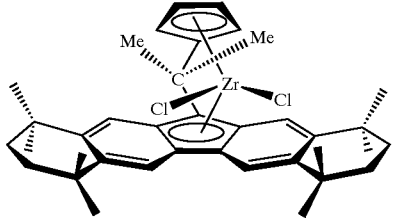

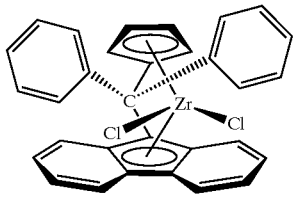

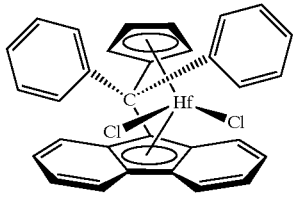

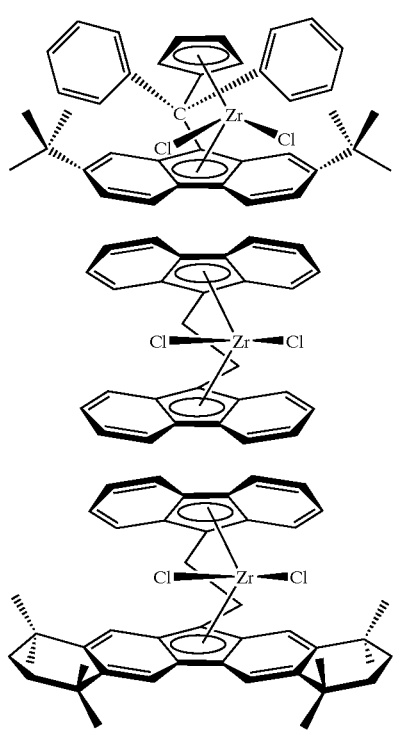
Example 53
Syndiotactic Polymerizations
Example 54
Catalysts for Isotactic Polymerization
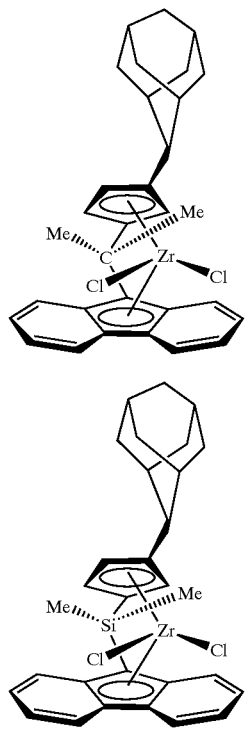
TABLE 5
MAO-cocatalyzed polymerization results with 8, 9, 10, 11, 12, 13, 14, 15, 16, and 17.
| Entry | Metallocene (mg) | MAO (equiv) | $T_p$ (° C.) | Tol. (mL) | $C_3H_6$ (mL) | Time (min.) | Yield (g) | Activity gP/(gmet h) | $T_m{}^a$ (° C.) | [r] (%) | $M_w$ | $M_w/M_n$ |
|---|---|---|---|---|---|---|---|---|---|---|---|---|
| 1 | 8 (0.5) | 2000 | 0 | 1.0 | 30 | 10 | 0.48 | 5700 | 153 | >99 | 961,000 | 2.12 |
| 2 | 8 (0.5) | 2000 | 20 | 1.0 | 30 | 10 | 1.16 | 14000 | 148 | >98 | 843,000 | 1.75 |
| 3 | 8 (2.0) | 1000 | 0 | 2.0 | 30 | 10 | 0.82 | 2500 | 149 | | | |
| 4 | 8 (2.0) | 1000 | 20 | 2.0 | 30 | 10 | 1.44 | 4300 | 146 | | | |
| 5 | 8 (2.0) | 1000 | 0 | 30.0 | 3 | 20 | 1.44 | 2200 | 146 | >98 | | |
| 6 | 8 (2.0) | 1000 | 20 | 30.0 | 3 | 5 | 1.68 | 10000 | 140 | | | |
| 7 | 9 (3.0) | 1000 | 0 | 2.0 | 30 | 15 | 0.25 | 330 | 111 | 88.6 | | |
| 8 | 9 (3.0) | 1000 | 20 | 2.0 | 30 | 10 | 0.98 | 2000 | 88 | 89.8 | | |
| 9 | 10 (2.0) | 1000 | 0 | 2.0 | 30 | 10 | 0.27 | 800 | 140 | >98 | | |
| 10 | 10 (2.0) | 1000 | 20 | 2.0 | 30 | 5 | 1.60 | 9600 | 137 | | | |
| 11 | 11 (3.0) | 1000 | 0 | 2.0 | 30 | 60 | 0.27 | 90 | 141 | 92.2 | | |
| 12 | 11 (3.0) | 1000 | 20 | 2.0 | 30 | 20 | 1.27 | 1300 | 120 | 89.7 | | |
| 13 | 12 (0.5) | 2000 | 0 | 1.0 | 30 | 10 | 0.26 | 3100 | 151 | >98 | | |
| 14 | 12 (0.5) | 2000 | 20 | 1.0 | 30 | 10 | 0.26 | 3100 | 147 | | | |
| 15[b] | 12 (2.0) | 1000 | 0 | 2.0 | 30 | 10 | 1.16 | 3500 | 154 | 97.5 | 535,000 | 2.00 |
| 16 | 12 (2.0) | 1000 | 20 | 2.0 | 30 | 10 | 4.79 | 14000 | 153 | | 310,000 | 2.03 |
| 17 | 13 (1.0) | 1000 | 0 | 2.0 | 30 | 10 | 0.31 | 1900 | 142 | | | |
| 18 | 13 (1.0) | 1000 | 20 | 2.0 | 30 | 10 | 1.13 | 6800 | 136 | | | |
| 19 | 14 (3.0) | 1000 | 0 | 2.0 | 30 | 30 | 0.16 | 110 | 124 | | | |
| 20 | 14 (3.0) | 1000 | 20 | 2.0 | 30 | 15 | 0.70 | 940 | 119 | | | |
| 21 | 15 (2.0) | 1000 | 0 | 2.0 | 30 | 5 | 1.12 | 6700 | 144 | | | |
| 22 | 15 (2.0) | 1000 | 20 | 2.0 | 30 | 3 | 2.24 | 22000 | 139 | | | |
| 23 | 16 (0.5) | 2000 | 0 | 1.0 | 30 | 5 | 3.00 | 72000 | n.o. | 50.2 | | |
| 24 | 16 (0.5) | 2000 | 20 | 1.0 | 30 | 5 | 5.09 | 120000 | n.o. | 50.5 | | |
| 25 | 17 (0.5) | 2000 | 0 | 1.0 | 30 | 5 | 1.09 | 26000 | n.o. | 81.3 | | |
| 26 | 17 (0.5) | 2000 | 20 | 1.0 | 30 | 5 | 2.85 | 68000 | n.o. | 74.1 | | |
[a] n.o. = not observed.
[b] See Reference 19.

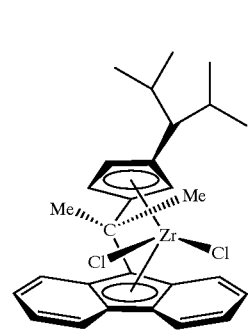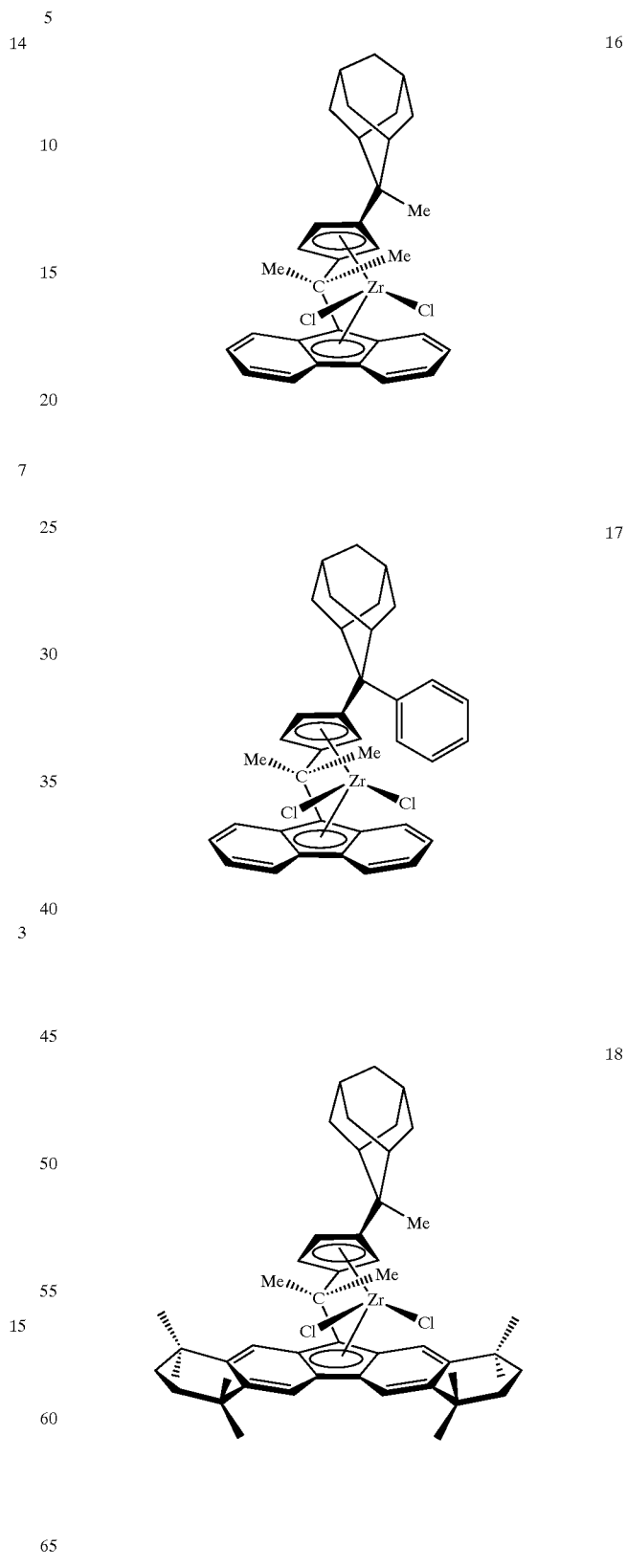

Example 55
Isotactic Polymerizations

TABLE 6

MAO-cocatalyzed polymerization results with 3, 7, 12, 13, 14, 15, 16, 17, and 18.

| Entry | Metallocene (mg) | MAO (eq.) | $T_p$ (° C.) | Tol. (mL) | $C_3H_6$ (mL) | Time (min.) | Yield (g) | Activity $\frac{gP}{(gmeth)}$ | $T_m^a$ (° C.) | $m^4$ (%) | $M_w$ | $M_w/M_n$ |
|---|---|---|---|---|---|---|---|---|---|---|---|---|
| 1 | 12 (0.5) | 2000 | 0 | 1.0 | 30 | 30 | 1.50 | 6000 | n.o. | 28.4 | 134,000 | 3.15 |
| 2 | 12 (0.5) | 2000 | 20 | 1.0 | 30 | 10 | 1.08 | 13000 | n.o. | 31.4 | 81,900 | 4.38 |
| 3 | 13 (1.0) | 1000 | 0 | 2.0 | 30 | 15 | 0.18 | 730 | 109 | 60.2 | 360,000 | 1.75 |
| 4 | 13 (1.0) | 1000 | 20 | 2.0 | 30 | 15 | 1.62 | 6500 | 110 | 57.5 | 322,000 | 1.70 |
| 5 | 14 (2.0) | 1000 | 0 | 2.0 | 30 | 5 | 0.16 | 970 | 129 | 78.6 | 76,700 | 1.81 |
| 6 | 14 (2.0) | 1000 | 20 | 2.0 | 30 | 30 | 0.36 | 360 | 131 | 80.0 | 80,900 | 2.63 |
| 7 | 7 (2.0) | 1000 | 0 | 2.0 | 30 | 20 | 0.32 | 480 | 137 | 86.1 | | |
| 8 | 7 (2.0) | 1000 | 20 | 2.0 | 30 | 20 | 0.47 | 710 | 138 | 81.2 | | |
| 9 | 3 (2.0) | 1000 | 0 | 2.0 | 30 | 20 | 0.93 | 1400 | 126 | 79.5 | | |
| 10 | 3 (2.0) | 1000 | 20 | 2.0 | 30 | 3 | 1.01 | 10000 | 125 | 81.5 | | |
| 11 | 15 (1.0) | 1000 | 0 | 1.0 | 30 | 15 | 0.28 | 1100 | 144 | | | |
| 12 | 15 (1.0) | 1000 | 20 | 1.0 | 30 | 3 | 0.66 | 13000 | 139 | | | |
| 13 | 16 (1.0) | 1000 | 0 | 2.0 | 30 | 10 | 0.41 | 158 | 158 | >98 | 171,00 | 1.93 |
| 14 | 16 (1.0) | 1000 | 20 | 2.0 | 30 | 10 | 0.83 | 5000 | 154 | >98 | 113,000 | 1.93 |
| 15 | 16 (2.0) | 1000 | 0 | 2.0 | 55 | 60 | 3.88 | 1900 | 160 | >98 | 157,000 | 2.48 |
| 16 | 16 (2.0) | 1000 | 20 | 2.0 | 55 | 10 | 2.13 | 6400 | 156 | | 124,000 | 1.90 |
| 17 | 16 (2.0) | 1000 | 0 | 2.0 | 55 | 10 | 1.38 | 4100 | 159 | | 160,000 | 1.91 |
| 18 | 16 (2.0) | 1000 | 0 | 30.0 | 3 | 180 | 0.87 | 140 | 158 | | 102,000 | 1.82 |
| 19 | 16 (2.0) | 1000 | 20 | 30.0 | 3 | 90 | 0.50 | 170 | 148 | | 54,400 | 2.08 |
| 20 | 17 (3.0) | 1000 | 0 | 2.0 | 30 | 120 | 0.03 | 4 | n.o. | | | |
| 21 | 17 (3.0) | 1000 | 20 | 2.0 | 30 | 120 | 0.02 | 3 | n.o. | | | |
| 22 | 18 (2.0) | 1000 | 0 | 2.0 | 30 | 20 | 0.29 | 440 | 167 | >99 | 370,000 | 1.39 |
| 23 | 18 (2.0) | 1000 | 20 | 2.0 | 30 | 20 | 0.70 | 1100 | 163 | >99 | 425,000 | 1.77 |

$^a$n.o. = melting temperature not observed.

REFERENCES

[1] a) Brintzinger, H. H.; Fischer, D.; Mülhaupt, R.; Rieger, B.; Waymouth, R. M. *Angew. Chem., Intl. Ed. Engl.* 1995 34, 1143.
 b) *Ziegler Catalysts, Recent Scientific Innovations and Technological Improvements;* Fink, G.; Mülhaupt, R.; Brintzinger, H. H., Eds.; Springer: Berlin, 1995.
 c) Kaminsky, W.; Arndt, M. *Adv. Polym. Sci.* 1997 127, 143–187.
[2] a) Banzi, V.; Angiolini, L.; Caretti, D.; Carlini, C. *Angew. Makromol. Chem.* 1995 229, 113–122.
 b) Resconi, L.; Piemontesi, F.; Galimberti, M. U.S. Pat. No. 5,886,123, 1996.
 c) Hoel, E. L.; U.S. Pat. No. 4,871,705, 1989, U.S. Pat. No. 5,001,205, 1991 and U.S. Pat. No. 5,491,207, 1996.
 d) Schiffino, R. S; Zamora, J. M. U.S. Pat. No. 5,696,213, 1997.
[3] (a) Resconi, L.; Jones, R. L.; Rheingold, A. L.; Yap, G. P. A. *Organometallics* 1996 15, 998–1005.
 (b) Ewart, S. W.; Sarsfield, M. J.; Jeremic, D.; Tremblay, T. L.; Williams, E. F.; Baird, M. C. *Organometallics* 1998 17, 1502–1510.
 (c) Averbuj, C.; Tish, E.; Eisen, M. S. *J. Am. Chem. Soc.* 1998 120, 8640–8646.
 (d) Kimura, K.; Takaishi, K.; Matsukawa, T.; Yoshimura, T.; Yamazaki, H. *Chem. Lett.* 1998 7, 571–572.
 (e) Xie, B. H.; Wu, Q.; Lin, S. G. *Acta Polymerica Sinica* 1999 1, 15–19.
 (f) Xie, B. H.; Wu, Q.; Lin, S. G. *Macromolecular Rapid Communications* 1999 20, 167–169.
[4] Chien, J. C. W.; Iwamoto, Y.; Rausch, M. D.; Wedler, W.; Winter, H. H. *Macromolecules* 1997 30, 3447–3458.
[5] a) Bravakis, A. M.; Bailey, L. E.; Pigeon, M.; Collins, S. *Macromolecules* 1998 31, 1000–1009.
 b) Gauthier, W. J.; Collins, S. *Maromol. Symp.* 1995 98, 223–231.
 c) Gauthier, W. J.; Collins, S. *Macromolecules* 1995 28, 3779–3786.
 d) Chien, J. C. W.; Llinas, G. H.; Rausch, M. D.; Lin, Y. G.; Winter, H. H.; Atwood, J. L.; Bott, S. G. *J. Poly. Sci. A Poly. Chem.* 1992 30, 2601–2617.
 e) Llinas, G. H.; Dong, S. H.; Mallin, D. T.; Rausch, M. D.; Lin, Y. G.; Winter, H. H.; Chien, J. C. W. *Macromolecules* 1992 25, 1242–1253.
 f) Chien, J. C. W.; Rausch, M. D. U.S. Pat. No. 5,756,614, 1998.
[6] a) Coates, G. W.; Waymouth, R. M. *Science* 1995 267, 217–219.
 b) Waymouth, R. M.; Coates, G. W.; Hauptman. E. M. U.S. Pat. Nos. 5,594,080 and 5,969,070.
 c) Bruce, M. D.; Coates, G. W.; Hauptman, E.; Waymouth, R. M.; Ziller, J. W. *J. Am. Chem. Soc.* 1997 119, 11174–11182.
 d) Carlson, E. D.; Krejchi, M. T.; Shah, C. D.; Terakawa, T.; Waymouth, R. M.; Fuller, G. G. *Macromolecules* 1998 31, 5343–5351.
 e) Kravchenko, R.; Masood, A.; Waymouth, R. M.; Myers, C. L. *J. Am. Chem. Soc.* 1998 120, 2039–2046.
[7] a) Dietrich, U.; Hackmann, M.; Rieger, B.; Klinga, M.; Leskelä, M. *J. Am. Chem. Soc.* 1999 121, 4348–4355.
 b) Dietrich, U.; Hackmann, M.; Rieger, B. *Rubber Chem. Technol.* 1998.
[8] a) Petoff, J. L. M.; Agoston, T., Lal, T. K.; Waymouth, R. M. *J. Am. Chem. Soc.* 1998 120, 11316–11322.
 b) Hu, Y. R.; Krejchi, M. T.; Shah, C. D.; Myers, C. L.; Waymouth, R. M. *Macromolecules* 1998 31, 6908–6916.

c) Bruce, M. D.; Waymouth, R. M. *Macromolecules* 1998 31, 2707–2715.

d) Madkour, T. M.; Mark, J. E. *Macromol. Theory and Sim.* 1998 7, 69–77.

[9] a) Ewen, J. A.; Elder, M. J.; Jones, R. L.; Haspeslagh, L.; Atwood, J. L.; Bott, S. G.; Robinson, K. *Makromol. Chem., Macromol. Symp.* 1991 48/49, 253–295.

b) Ewen, J. A. U.S. Pat. No. 5,036,034, 1991.

c) Razavi, A.; Atwood, J. L. *J Organomet. Chem.* 1995 497, 105–111.

d) Herfert, N.; Fink, G. *Makromol. Chem., Macromol. Symp.* 1993 66, 157–178.

[10] Razavi, A.; Atwood, J. L. *J. Organomet. Chem.* 1995 497, 105–111.

[11] Abrams, M. B.; Yoder, J. C.; Loeber, C.; Day, M. W.; Bercaw, J. E. *Organometallics* 1999 18, 1389–1401.

What is claimed is:

1. A method for producing a polyolefin comprising contacting at least one olefin monomer with a metallocene catalyst in the presence of an activator thereof under suitable reaction conditions for a time sufficient to catalytically polymerize said at least one olefin monomer to form a polymer, wherein said metallocene catalyst has the formula

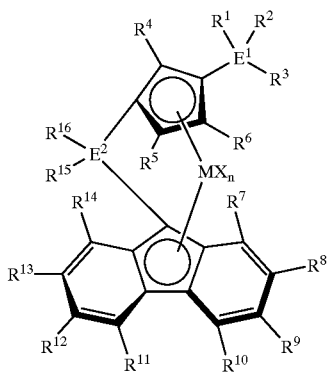

wherein:

a) M is selected from the group consisting of a group III Transition metal, a group IV Transition metal, a group V Transition metal, a Lanthamide and an Actinide;

b) X is selected from the group consisting of fluorine, chlorine, bromine, iodine, hydrogen, $C_1$ to $C_{10}$ alkyl, $C_6$ to $C_{20}$ aryl, alkylaryl, arylalkyl, $C_1$ to $C_{10}$ fluoroalkyl, $C_6$ to $C_{20}$ fluoroaryl, and —$OR^{17}$ where $R^{17}$ is a $C_1$ to $C_{10}$ alkyl or $C_6$ to $C_{20}$ aryl; and n is the formal oxidation state of M minus 2;

c) $E^1$ is selected from hydrogen, carbon, silicon, and germanium, wherein $R^1$, $R^2$, and $R^3$ are not present when $E^1$ is hydrogen;

d) $E^2$ is selected from carbon, silicon, and germanium;

e) $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{15}$, and $R^{16}$ are independently selected from the group consisting of hydrogen, $C_1$ to $C_{10}$ alkyl, 3 to 10 membered optionally substituted cycloalkyl, $C_6$ to $C_{16}$ aryl, $C_6$ to $C_{16}$ arylalkyl, and $Si(R^{18})_3$ where $R^{18}$ is selected from $C_1$ to $C_{10}$ alkyl, $C_6$ to $C_{16}$ aryl and $C_3$ to $C_{10}$ cycloalkyl, and wherein two or three of $R^1$, $R^2$ and $R^3$ taken together with $E^1$ can form an optionally substituted 4 to 16 member cyclic group; and f) $R^9$ and $R^{12}$ are independently selected from the group consisting of $C_1$ to $C_{10}$ alkyl, 3 to 10 membered optionally substituted cycloalkyl, $C_6$ to $C_{16}$ aryl, $C_6$ to $C_{16}$ arylalkyl, and $Si(R^{18})_3$ where $R^{18}$ is selected from a $C_1$ to $C_{10}$ alkyl, $C_6$ to $C_{16}$ aryl and $C_3$ to $C_{10}$ cycloalkyl, and wherein any two adjacent members of $R^8$, $R^9$, $R^{12}$ and $R^{13}$, taken together with the atoms to which they are attached, can form an optionally substituted 4 to 16 member cyclic group.

2. A method for producing a polyolefin comprising contacting at least one olefin monomer with a metallocene catalyst in the presence of an activator thereof under suitable reaction conditions for a time sufficient to catalytically polymerize said at least one olefin monomer to form a polymer, wherein said metallocene catalyst has the formula

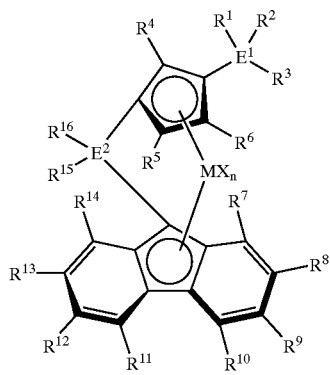

wherein:

a) M is selected from the group consisting of a group III Transition metal, a group IV Transition metal, a group V Transition metal, a Lanthamide and an Actinide;

b) X is selected from the group consisting of fluorine, chlorine, bromine, iodine, hydrogen, $C_1$ to $C_{10}$ alkyl, $C_6$ to $C_{20}$ aryl, alkylaryl, arylalkyl, $C_1$ to $C_{10}$ fluoroalkyl, $C_6$ to $C_{20}$ fluoroaryl, and —$OR^{17}$ where $R^{17}$ is a $C_1$ to $C_{10}$ alkyl or $C_6$ to $C_{20}$ aryl; and n is the formal oxidation state of M minus 2;

c) $E^1$ is selected from carbon, silicon, and germanium;

d) $E^2$ is selected from carbon, silicon, and germanium;

e) $R^1$, $R^2$, $R^3$ are independently selected from the group consisting of hydrogen, $C_1$ to $C_{10}$ alkyl, 3 to 10 membered cycloalkyl optionally substituted with from 1 to 10 $C_1$ to $C_{10}$ alkyls, $C_6$ to $C_{16}$ aryl, $C_6$ to $C_{16}$ arylalkyl, and $Si(R^{18})_3$ where $R^{18}$ is selected from a $C_1$ to $C_{10}$ alkyl, $C_6$ to $C_{16}$ aryl and $C_3$ to $C_{10}$ cycloalkyl, and wherein two or three of $R^1$, $R^2$ and $R^3$ taken together with $E^1$ form an optionally substituted 4 to 16 member cyclic group; and f) $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are independently selected from the group consisting of hydrogen, $C_1$ to $C_{10}$ alkyl, 3 to 10 membered optionally substituted cycloalkyl, $C_6$ to $C_{16}$ aryl, $C_6$ to $C_{16}$ arylalkyl, and $Si(R^{18})_3$ where $R^{18}$ is selected from $C_1$ to $C_{10}$ alkyl, $C_6$ to $C_{16}$ aryl and $C_3$ to $C_{10}$ cycloalkyl, and wherein any two adjacent members of, $R^5$, $R^6$, $R^7$, $R^8$, $R^9$, $R^{10}$, $R^{11}$, $R^{12}$, $R^{13}$, and $R^{14}$, taken together with the atoms to which they are attached, can form an optionally substituted 4 to 16 member cyclic group, and wherein $R^{15}$ and $R^{16}$ taken together with $E^2$ can form an optionally substituted 4 to 16 member cyclic group.

3. The method of claim 2, wherein said reaction conditions comprise polymerizing the at least one olefin monomer homogeneously in solution.

4. The method of claim 3, further comprising a solvent in the solution.

5. The method of claim 2, wherein said reaction conditions comprise polymerizing the at least one olefin monomer with the catalyst supported in a solution.

6. The method of claim 2, wherein said reaction conditions comprise polymerizing the at least one olefin monomer in the gas phase.

7. The method of claim 2, wherein said reaction conditions comprise polymerizing the at least one olefin monomer at high pressure.

8. The method of claim 2, wherein said reaction conditions comprise polymerizing the at least one olefin monomer in bulk monomer.

9. The method of claim 2, wherein said reaction conditions comprise polymerizing the at least one olefin monomer in a condensed phase of a lower molecular weight alk-1-ene.

10. The method of claim 2, wherein the activator is selected from an alkylaluminum, a haloalkylaluminum, an alkylaluminoxane, aluminoxane, methylaluminoxane, modified methylaluminoxane, a Lewis acid,-or a protic acid containing a non-coordinating counter ion.

11. The method of claim 2, wherein the activator is $B(C_6 F_5)_3$ or $[PhNMe_2H]^+B(C_6 F_5)^-_4$.

12. The method of claim 10, wherein said activator is a Lewis acid or a protic acid and said contacting further takes place in the presence of an alkylaluminum compound.

13. The method of claim 2, wherein a mixture of olefin monomers are contacted with the metallocene catalyst to form a copolymer or terpolymer.

14. The method of claim 2, wherein the monomer is selected from ethylene, propylene, 1-butene, 1-pentene, 4-methyl-1-pentene, 1-hexene, and combinations thereof.

15. The method of claim 2, wherein a combination of at least two metallocene catalysts is used to contact the monomer.

16. The method of claim 2 wherein said compound has $C_1$ symmetry.

17. The method of claim 2 wherein $R^1$, $R^2$ and $R^3$ are not hydrogen.

18. The method of claim 2 wherein two or three of $R^1$, $R^2$ and $R^3$ form part of a $C_6$ cyclic group or a substituted $C_6$ cyclic group.

19. The method of claim 18 wherein said $C_6$ cyclic group or substituted $C_6$ cyclic group is optionally substituted cyclohexyl, optionally substituted norbornyl, optionally substituted adamantyl, or optionally substituted 2-methyl-adamantyl.

20. The method of claim 19 wherein $R^{15}$ and R16 are each independently methyl or phenyl.

21. The method of claim 2, wherein:

M is Ti, Hf or Zr;

X is hydride, halogen, alkoxide or $C_1$–$C_7$ hydrocarbyl;

two or three of $R^1$, $R^2$ and $R^3$ form part of a $C_6$ cyclic group or a substituted $C_6$ cyclic group $C_6$ selected from optionally substituted cyclohexyl, optionally substituted norbornyl, optionally substituted adamantyl, or optionally substituted 2-methyl-adamantyl;

$R^{15}$ and $R^{16}$ are each independently methyl or phenyl;

the activator is chosen from an alkylaluminum, a haloalkylaluminum, an alkylaluminoxane, aluminoxane, methylaluminoxane, modified methylaluminoxane, a Lewis acid, or a protic acid containing a non-coordinating counter ion; and the monomer is chosen from ethylene, propylene, 1-butene, 1-pentene, 4-methyl-1-pentene, 1-hexene, and combinations thereof.

22. A method for producing a polyolefin comprising contacting at least one olefin monomer with a metallocene catalyst in the presence of an activator thereof under suitable reaction conditions for a time sufficient to catalytically polymerize said at least one olefin monomer to form a polymer, wherein said metallocene catalyst has the formula

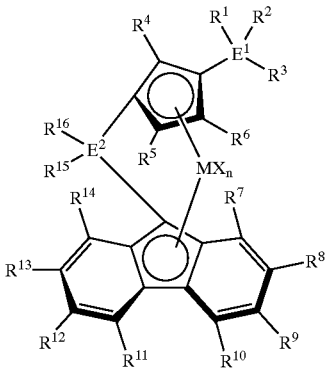

wherein:

a) M is selected from the group consisting of a group III Transition metal, a group IV Transition metal, a group V Transition metal, a Lanthamide and an Actinide;

b) X is selected from the group consisting of fluorine, chlorine, bromine, iodine, hydrogen, $C_1$ to $C_{10}$ alkyl, $C_6$ to $C_{20}$ aryl, alkylaryl, arylalkyl, $C_1$ to $C_{10}$ fluoroalkyl, $C_6$ to $C_{20}$ fluoroaryl, and —$OR^{17}$ where $R^{17}$ is a $C_1$ to $C_{10}$ alkyl or $C_6$ to $C_{20}$ aryl; and n is the formal oxidation state of M minus 2;

c) $E^1$ is selected from carbon, silicon, and germanium;

d) $E^2$ is selected from carbon, silicon, and germanium;

e) $R^1$, $R^2$, $R^3$ are independently selected from the group consisting of hydrogen, $C_1$ to $C_{10}$ alkyl, 3 to 10 membered cycloalkyl optionally substituted with from 1 to 10 $C_1$ to $C_{10}$ alkyls, $C_6$ to $C_{16}$ aryl, $C_6$ to $C_{16}$ arylalkyl, and $Si(R^{18})_3$ where $R^{18}$ is selected from a $C_1$ to $C_{10}$ alkyl, $C_6$ to $C_{16}$ aryl and $C_3$ to $C_{10}$ cycloalkyl, and wherein two or three of $R^1$, $R^2$ and $R^3$ taken together with $E^1$ can form an optionally substituted 4 to 16 member cyclic group; and f) $R^4$, $R^5$, $R^6$, $R^7$, $R^{10}$, $R^{11}$, $R^{14}$, $R^{15}$, and $R^{16}$ are independently selected from the group consisting of hydrogen, $C_1$ to $C_{10}$ alkyl, 3 to 10 membered optionally substituted cycloalkyl, $C_6$ to $C_{16}$ aryl, $C_6$ to $C_{16}$ arylalkyl, and $Si(R^{18})_3$ where $R^{18}$ is selected from $C_1$ to $C_{10}$ alkyl, $C_6$ to $C_{16}$ aryl and $C_3$ to $C_{10}$ cycloalkyl; and g) $R^8$, $R^9$, $R^{12}$ and $R^{13}$ are independently selected from the group consisting of $C_1$ to $C_{10}$ alkyl, 3 to 10 membered optionally substituted cycloalkyl, $C_6$ to $C_{16}$ aryl, $C_6$ to $C_{16}$ arylalkyl, and $Si(R^{18})_3$ where $R^{18}$ is selected from $C_1$ to $C_{10}$ alkyl, $C_6$ to $C_{16}$ aryl and $C_3$ to $C_{10}$ cycloalkyl;

h) wherein any two adjacent members of $R^5$, $R^6$, $R^7$, $R^8$, $R^9$, $R^{10}$, $R^{11}$, $R^{12}$, $R^{13}$, and $R^{14}$, taken together with the atoms to which they are attached, can form an optionally substituted 4 to 16 member cyclic group, and wherein $R^{15}$ and $R^{16}$ taken together with $E^2$ can form an optionally substituted 4 to 16 member cyclic group.

23. The method of claim 22, wherein said reaction conditions comprise polymerizing the at least one olefin monomer homogeneously in solution.

24. The method of claim 23, further comprising a solvent in the solution.

25. The method of claim 22, wherein said reaction conditions comprise polymerizing the at least one olefin monomer with the catalyst supported in a solution.

26. The method of claim 22, wherein said reaction conditions comprise polymerizing the at least one olefin monomer in the gas phase.

27. The method of claim 22, wherein said reaction conditions comprise polymerizing the at least one olefin monomer at high pressure.

28. The method of claim 22, wherein said reaction conditions comprise polymerizing the at least one olefin monomer in bulk monomer.

29. The method of claim 22, wherein said reaction conditions comprise polymerizing the at least one olefin monomer in a condensed phase of a lower molecular weight alk-1-ene.

30. The method of claim 22, wherein the activator is selected from an alkylaluminum, a haloalkylaluminum, an alkylaluminoxane, aluminoxane, methylaluminoxane, modified methylaluminoxane, a Lewis acid, or a protic acid containing a non-coordinating counter ion.

31. The method of claim 22, wherein the activator is $B(C_6F_5)_3$ or $[PhNMe_2H]^+B(C_6F_5)^-_4$.

32. The method of claim 30, wherein said activator is a Lewis acid or a protic acid and said contacting further takes place in the presence of an alkylaluminum compound.

33. The method of claim 22, wherein a mixture of olefin monomers are contacted with the metallocene catalyst to form a copolymer or terpolymer.

34. The method of claim 22, wherein the monomer is selected from ethylene, propylene, 1-butene, 1-pentene, 4-methyl-1-pentene, 1-hexene, and combinations thereof.

35. The method of claim 22, wherein a combination of at least two metallocene catalysts is used to contact the monomer.

36. The method of claim 22, wherein $R^8$ and $R^9$ taken together with the atoms to which they are attached form an optionally substituted 4 to 16 member cyclic group, and wherein $R^{12}$ and $R^{13}$ taken together with the atoms to which they are attached form an optionally substituted 4 to 16 member cyclic group.

37. The method of claim 36 wherein the metallocene catalyst has the formula

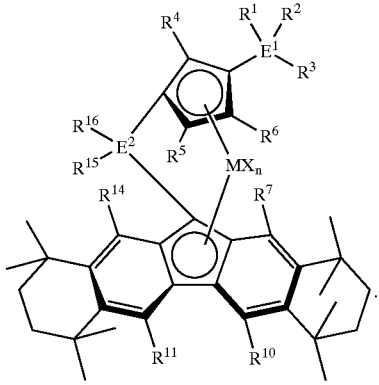

38. The method of claim 22, wherein:
M is Ti, Hf or Zr;
X is hydride, halogen, alkoxide or $C_1-C_7$ hydrocarbyl;
$R^8$ and $R^9$ taken together with the atoms to which they are attached form an optionally substituted 4 to 16 member cyclic group, and wherein $R^{12}$ and $R^{13}$ taken together with the atoms to which they are attached form an optionally substituted 4 to 16 member cyclic group the activator is chosen from an alkylaluminum, a haloalkylaluminum, an alkylaluminoxane, aluminoxane, methylaluminoxane, modified methylaluminoxane, a Lewis acid, or a protic acid containing a non-coordinating counter ion; and the monomer is chosen from ethylene, propylene, 1-butene, 1-pentene, 4-methyl-1-pentene, 1-hexene, and combinations thereof.

39. A method for producing a polyolefin comprising contacting at least one olefin monomer with a metallocene catalyst in the presence of an activator thereof under suitable reaction conditions for a time sufficient to catalytically polymerize said at least one olefin monomer to form a polymer, wherein said metallocene catalyst has the formula

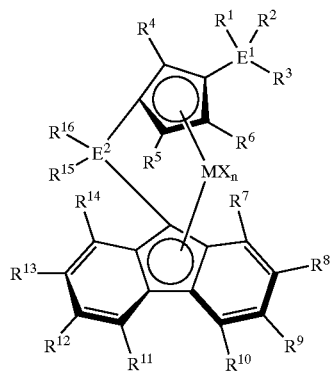

wherein:
a) M is selected from the group consisting of a group III Transition metal, a group IV Transition metal, a group V Transition metal, a Lanthamide and an Actinide;

b) X is selected from the group consisting of fluorine, chlorine, bromine, iodine, hydrogen, $C_1$ to $C_{10}$ alkyl, $C_6$ to $C_{20}$ aryl, alkylaryl, arylalkyl, $C_1$ to $C_{10}$ fluoroalkyl, $C_6$ to $C_{20}$ fluoroaryl, and $-OR^{17}$ where $R^{17}$ is a $C_1$ to $C_{10}$ alkyl or $C_6$ to $C_{20}$ aryl; and n is the formal oxidation state of M minus 2;

c) $E^1$ is selected from hydrogen, carbon, silicon, and germanium, wherein $R^1$, $R^2$, and $R^3$ are not present when $E^1$ is hydrogen;

d) $E^2$ is selected from carbon, silicon, and germanium;

e) $R^1$, $R^2$, $R^3$, $R^4$, $R^5$, $R^7$, $R^8$, $R^9$, $R^{10}$, $R^{11}$, $R^{12}$, $R^{13}$, $R^{14}$, $R^{15}$, and $R^{16}$ are independently selected from the group consisting of hydrogen, $C_1$ to $C_{10}$ alkyl, 3 to 10 membered optionally substituted cycloalkyl, $C_6$ to $C_{16}$ aryl, $C_6$ to $C_{16}$ arylalkyl, and $Si(R^{18})_3$ where $R^{18}$ is selected from $C_1$ to $C_{10}$ alkyl, $C_6$ to $C_{16}$ aryl and $C_3$ to $C_{10}$ cycloalkyl, wherein two or three of $R^1$, $R^2$ and $R^3$ taken together with $E^1$ can form an optionally substituted 4 to 16 member cyclic group, and wherein any two adjacent members of $R^7$, $R^8$, $R^9$, $R^{10}$, $R^{11}$, $R^{12}$, $R^{13}$, and $R^{14}$, or $R^{15}$ and $R^{16}$, taken together with the atoms to which they are attached can form an optionally substituted 4 to 16 member cyclic group; and f) $R^6$ is selected from the group consisting of $C_1$ to $C_{10}$ alkyl, 3 to 10 membered optionally substituted cycloalkyl, $C_6$ to $C_{16}$ aryl, $C_6$ to $C_{16}$ arylalkyl, and $Si(R^{18})_3$ where $R^{18}$ is selected from C to $C_{10}$alkyl, $C_6$ to $C_{16}$ aryl and $C_3$ to $C_{10}$ cycloalkyl.

40. The method of claim 39, wherein said reaction conditions comprise polymerizing the at least one monomer homogeneously in solution.

41. The method of claim 39, wherein said reaction conditions comprise polymerizing the at least one olefin monomer with the catalyst supported in a solution.

42. The method of claim 39, wherein said reaction conditions comprise polymerizing the at least one olefin monomer in the gas phase.

43. The method of claim 39, wherein said reaction conditions comprise polymerizing the at least one olefin monomer at high pressure.

44. The method of claim 39, wherein said reaction conditions comprise polymerizing the at least one olefin monomer in bulk monomer.

45. The method of claim 39, wherein said reaction conditions comprise polymerizing the at least one olefin monomer in a condensed phase of a lower molecular weight alk-1-ene.

46. The method of claim 39, wherein the activator is selected from an alkylaluminum, a haloalkylaluminum, an alkylaluminoxane, aluminoxane, methylaluminoxane, modified methylaluminoxane, a Lewis acid, or a protic acid containing a non-coordinating counter ion.

47. The method of claim 39, wherein the activator is $B(C_6F_5)_3$ or $[PhNMe_2H]^+B(C_6F_5)^-_4$.

48. The method of claim 46, wherein said contacting further takes place in the presence of an alkylaluminum compound.

49. The method of claim 39, wherein a mixture of olefin monomers are contacted with the metallocene catalyst to form a copolymer or terpolymer.

50. The method of claim 39, wherein the monomer is selected from ethylene, propylene, 1-butene, 1-pentene, 4-methyl-1-pentene, 1-hexene, and combinations thereof.

51. The method of claim 39, wherein a combination of at least two metallocene catalysts is used to contact the monomer.

52. The method of claim 39, wherein $R_6$ is selected from $C^1$ to $C^{10}$ alkyl and 3 to 10 membered optionally substituted cycloalkyl.

53. The method of claim 39, wherein $R^6$ is $C_1$ to $C_{10}$ alkyl.

54. The method of claim 39, wherein $R^6$ is methyl.

55. The method of claim 39, further comprising a solvent in the solution.

56. The method of claim 39, wherein:

M is Ti, Hf or Zr;

X is hydride, halogen, alkoxide or $C_1$–$C_7$ hydrocarbyl;

$R^6$ is $C_1$ to $C_{10}$ alkyl;

the activator is chosen from an alkylaluminum, a haloalkylaluminum, an alkylaluminoxane, aluminoxane, methylaluminoxane, modified methylaluminoxane, a Lewis acid, or a protic acid containing a non-coordinating counter ion; and the monomer is chosen from ethylene, propylene, 1-butene, 1-pentene, 4-methyl-1-pentene, 1-hexene, and combinations thereof.

* * * * *